(12) United States Patent
Liao et al.

(10) Patent No.: US 11,851,398 B2
(45) Date of Patent: Dec. 26, 2023

(54) CATALYTIC FUNNELING OF PHENOLICS

(71) Applicant: Katholieke Universiteit Leuven, K.U.Leuven R&D, Leuven (BE)

(72) Inventors: Yuhe Liao, Leuven (BE); Sander Van den Bosch, Wilsele (BE); Joost Van Aelst, Hasselt (BE); Bert Frans Sels, Westerlo (BE)

(73) Assignee: Katholieke Universiteit Leuven, K.U.Leuven R&D, Leuven (BE)

( * ) Notice: Subject to any disclaimer, the term of this patent is extended or adjusted under 35 U.S.C. 154(b) by 403 days.

(21) Appl. No.: 17/083,154

(22) Filed: Oct. 28, 2020

(65) Prior Publication Data

US 2021/0122691 A1 Apr. 29, 2021

Related U.S. Application Data

(60) Provisional application No. 62/926,936, filed on Oct. 28, 2019.

(51) Int. Cl.
| | | |
|---|---|---|
| *C07C 37/50* | (2006.01) | |
| *B01J 21/08* | (2006.01) | |
| *B01J 23/40* | (2006.01) | |
| *B01J 23/755* | (2006.01) | |
| *B01J 21/06* | (2006.01) | |
| *B01J 23/42* | (2006.01) | |
| *B01J 23/44* | (2006.01) | |
| *B01J 29/40* | (2006.01) | |

(52) U.S. Cl.
CPC ............ *C07C 37/50* (2013.01); *B01J 21/063* (2013.01); *B01J 21/08* (2013.01); *B01J 23/42* (2013.01); *B01J 23/44* (2013.01); *B01J 23/755* (2013.01); *B01J 29/40* (2013.01)

(58) Field of Classification Search
CPC ............ C07C 37/50; B01J 21/08; B01J 23/40
See application file for complete search history.

(56) References Cited

U.S. PATENT DOCUMENTS

| | | |
|---|---|---|
| 3,105,095 A | 9/1963 | Oshima et al. |
| 3,223,698 A | 12/1965 | Oshima et al. |
| 4,409,416 A | 10/1983 | Snell et al. |
| 4,420,664 A | 12/1983 | Huibers et al. |
| 4,927,979 A | 5/1990 | Yamagishi et al. |
| 2017/0152200 A1 | 6/2017 | Ma et al. |

*Primary Examiner* — Sikarl A Witherspoon
(74) *Attorney, Agent, or Firm* — TraskBritt

(57) ABSTRACT

In general, present invention concerns an integrated wood-to-xylochemicals biorefinery, enabling production of renewable phenol, phenolic oligomers, propylene, and carbohydrate pulp from lignocellulosic biomass.

20 Claims, 26 Drawing Sheets

CATALYTIC FUNNELING OF PHENOLICS

CROSS-REFERENCE TO RELATED APPLICATION

This application claims the benefit under 35 U.S.C. § 119(e) of U.S. Provisional Patent Application Ser. No. 62/926,936, filed Oct. 28, 2019, the disclosure of which is hereby incorporated herein in its entirety by this reference.

TECHNICAL FIELD

In general, this present disclosure concerns an integrated lignocellulose biorefinery, enabling production of renewable phenol, phenolic oligomers, propylene, and carbohydrate pulp from lignocellulosic biomass.

BACKGROUND

Production of chemicals is rapidly becoming the single largest driver of global oil consumption in the future[1, 2] To reduce the oil consumption and the resulting greenhouse gas emission, a shift from non-renewable fossil to renewable carbon resources is required. Lignocellulose, as an abundant feedstock of renewable carbon, can be used for production of bio-fuels, bio-chemicals and bio-materials.[3, 4] However, most of the proposed lignocellulose biorefineries cannot economically compete with oil refineries due, in part, to incomplete utilization of feedstock. Therefore, it is imperative to maximize feedstock utilization to be not only cost but also environmentally competitive with fossil oil-based processes.[5] There is thus a need for new integrated biorefinery concepts that offer biomass refining with low energy requirements and high feedstock utilization (carbon and mass) efficiency, providing multiple products stream into markets. The inherent heterogeneity of lignocellulose, comprising entangled sugar-based (i.e., (hemi-cellulose) and aromatic (i.e., lignin) biopolymers, complicates its valorization into high value products. In particular, production of high value chemicals from lignin—a methoxylated phenyl-propanoid biopolymer—is challenging due to its inherent recalcitrance and heterogeneity.[6-9] In contrast to relatively oxygen-free fossil oil, oxygen-containing functional groups are plentiful in lignocellulose. Therefore, functionalized aromatics, such as phenol are among the most suggested chemicals from lignin, but product yields on lignin weight basis are currently low.

Phenol is a bulk chemical today, with a global annual production projected at 14.5 million tonnes in 2025.[10] Its main downstream use comprises the production of bisphenol A (46%), phenolic resins (28%), caprolactam (13%), aniline (3%), and alkylphenols (3%). Industrial phenol production currently proceeds through the Hock process, involving exothermic autoxidation of cumene, obtained from benzene alkylation with propylene, followed by acid-catalyzed decomposition of cumene hydroperoxide into equimolar amounts of phenol and acetone.[11, 12] Besides the fossil, non-renewable nature of the feedstock, and the use of dangerous intermediates/catalysts, such as hydroperoxide (explosive) and sulfuric acid (corrosive), the overall phenol yield (on benzene per single-pass basis) in the current process is only 5%,[13] while the overproduction of acetone is a potential market burden.[12]

Lignin, a natural alkyl-phenolic bio-polymer and second largest constituent in lignocellulose,[4, 6, 14] could produce vast amounts of renewable phenol, providing selective and industrially feasible lignin conversion strategies are available. Literature reports many (catalytic) routes to convert lignin into chemicals and fuels,[14] but the on-purpose lignin-to-phenol route is studied less intensively.[15] The main challenge lies in finding a strategy that combines (i) a high degree of lignocellulose delignification, with (ii) selective cleavage of CAr—O and CAr—Cα bonds (iii) without destructing the phenolic entity, while iv) keeping the carbohydrates unchanged.

The few available lignin-to-phenol reports include thermal and catalytic hydrotreatment, but none of them are in commercial use due to low phenol yields. For instance, direct catalytic hydrogenolysis of technical lignin (cf Noguchi process) gives 3 wt. % phenol yield.[15] Phenol from Kraft lignin is reported in the Lignol™ process by combining catalytic hydrocracking and non-catalytic thermal hydrodealkylation (FIG. 1).[16] Here, formation of large amounts of heavy oil, light distillate, benzene, and light alkanes, likely caused by high temperature (350 to 450° C.) and pressure (up to 170 bar), restricts the yield of phenol.[15, 16]

There are many different methods such as oxidation, hydroprocessing, and pyrolysis to depolymerize lignin into phenolics (FIG. 2). However, the monomeric phenol products of lignin from these approaches are usually (methoxylated) alkylphenols rather than the herein targeted bio-phenol. Therefore, the yield of simple, unsubstituted phenol from these one-step strategies is very low. For example, the yield of phenol from pyrolysis is usually lower than 3 wt. % on the lignin intake basis (Table 1, entries 1-5). Huibers et al. filed a patent regarding steam thermal cracking of lignin at very high temperature (535 to 875° C.) over a fluidized bed rector (Table 1, entry 6). The yield of phenol is 11.3 wt. % on the organic lignin intake basis, which is the highest one, to the best of our knowledge, from thermal and non-catalytic conversion of lignin. In addition to phenol, there are some other alkylphenols such as 19.8 wt. % of p-cresol, 9.0 wt. % of m-cresol, 5.0 wt. % of catechol, 4.5 wt. % of methylcatechol. However, this process also produce 11.7 wt. % of tar and 37.0 wt. % of gases (such as 10.4 wt. % of CO and 10.9 wt. % of $CO_2$).

Due to the high oxygen content of lignin, reductive conversion of lignin is a promising approach to manufacture phenol. However, the yield of phenol from reductive conversion of lignin is also low (<4 wt. %, Table 1, entries 10-24) as the result of the presence of an alkyl chain (usually located at para position of the phenolic hydroxyl group). For instance, hydrocracking of Kraft lignin according to the Noguchi process produces 3.0 wt. % of phenol, 10.0 wt. % of cresols, 4.3 wt. % of ethylphenols, 2.0 wt. % of propylphenols, and 1.2 wt. % of xylenols. Hydrocracking according to Lignol™ process produces 2.5 wt. % of phenol, 9.5 wt. % of cresols, 12.5 wt. % of ethylphenols, 10.5 wt. % of propylphenols, and 2.6 wt. % of xylenols. Therefore, the main products are alkylphenols rather than phenol, even under hydrogen atmosphere. Other products include 25.2 wt. % of gases, 17.9 wt. % of $H_2O$, 14 wt. % of neutrals (i.e., hydrocarbons) and 11.1 wt. % of heavy products.

Feng et al. reported a one-step conversion of both orangosolv and in planta lignin into phenol through an oxidation-hydrogenation strategy over $CuCl_2$ and $Ru/CeO_2$ under hydrogen atmosphere to remove both methoxyl and alkyl groups simultaneously. The yield of phenol (around 14 wt. %) is the highest from the one-step process (on poplar lignin basis, ca. 23 wt. % of lignin in poplar wood, Table 1, entries 26-27). The yield of phenol surprisingly only reaches 0.5 wt. % on birch wood lignin basis (ca. 20 wt. % of lignin in birch wood, Table 1, entry 28) though both poplar and birch are hardwood. This difference is ascribed to the fact that poplar lignin is rich in p-hydroxybenzoate units (17.1%) such as p-hydroxybenzoic acid, p-methoxylbenzoic acid, and p-hydroxybenzoate, while birch wood only contains 2.1%.[47] The p-hydroxybenzoate units are similar top-hydroxyl phenol (H) units, which are the source of phenol formation. However, the main units in most of lignin are guaiacyl (G) and syringyl (S) units. The side chains are removed as $CO_2$ rather than bulk chemicals (in this work, it is propylene or ethylene), which reduces the carbon atom economy.

The above results show that one-step conversion of lignin cannot fully defunctionalize the monomers. Therefore, some multiple-steps approaches were proposed (Table 2). For instance, Schuth et al. investigated pyrolysis of oak wood, followed by hydrode-oxygenation and separation to yield phenol. Although this process avoids the fractionation of wood into different components (lignin, cellulose, and hemicellulose), the yield of phenol is limited to 3 wt. % on the lignin intake basis, Table 2, entry 2). Huibers et al. filed a patent regarding hydrocracking of Kraft lignin, followed by non-catalytic thermal hydrode-alkylation to phenol. Although the yield of alkylphenols (rich in cresols, ethylphenol and propylphenols) is 37.5 wt. % on organic lignin intake basis, the results of non-catalytic thermal hydrodealkylation were not demonstrated (Table 2, entry 4). Nevertheless, the non-catalytic thermal dealkylation of alkylphenol is usually a non-selective process. Recently, isolation of phenol from waste water of pyrolysis was also demonstrated.[48] This valorization approach can add value to the pyrolysis process and reduce the burden of waste water treatment. Since phenol content in the waste water is low and most products of pyrolysis are not present in the waste water, the yield of phenol is very low on biomass intake basis.

Recently, more practical lignin-first lignocellulosic biorefinery concepts were elaborated, based on the active stabilization of in planta lignin (intermediates) to avoid irreversible condensation of reactive intermediates. Unlike previous attempts, which used recalcitrant technical lignin, this in planta lignin depolymerization strategy produces a select number of methoxylated and alkylated phenolic monomers in close-to-theoretical yields, viz. 20 and 50 wt. % for soft- and hardwoods, respectively. Since the monomeric fraction only contains few and structural alike methoxy(alkyl)phenols, their isolation and conversion into phenol are practical to handle. Therefore, a distinct catalytic strategy is herein invented that converts the crude mixture of methoxylated and alkylated phenolic monomers, obtained from RCF of wood, into phenol and propylene (FIG. 1). n-Propylbenzene is utilized as an organic solvent in industries such as printing and the dyeing of textiles and in the manufacture of methylstyrene. However, Friedel-Crafts alkylation benzene usually gives isopropylbenzene as the product due to higher thermodynamic stability of the secondary propyl carbocation as compared to the primary one. Therefore, its selective production in a traditional petro-refinery via alkylation of benzene is challenging. Since lignin contains propyl chain, n-propylbenzene can be yielded from lignin viademethoxylation and/or cascade demethylation-dehydroxylation of methoxylated and alkylated phenolic monomers, obtained from RCF of wood, provided that complete removal of oxygen is reached without hydrogenation of aromatic ring. Conversion of phenolic monomers, obtained from RCF of wood, to n-propylbenzene is seldom reported. It was reported that bifunctional molybdenum polyoxometalate can transform 4-propylguaiacol to n-propylbenzene with highest yield of 42%.[72] Other products includes methylated products such as propyltoluene, propylcresols due to C-alkylation and alkylphenols. A bimetallic platinum and molybdenum catalyst supported on multi-walled carbon nanotubes can selectively convert 4-propylguaiacol to n-propylbenzene (93.2% yield) at 1 bar $H_2$.[73] However, conversion of 4-propylsyringol (one major lignin monomer) to n-propylbenzene was not investigated in both studies. More importantly, the catalysts developed in both studies are not catalytic stable.[72, 74] The instability of catalysts may reduce the profitability of the biorefinery. Thus, it is essential to develop both selective and stable heterogeneous catalysts for conversion of RCF lignin monomers into n-propylbenzene.

In this patent application, the in planta lignin was first converted into monomers (rich in guaiacols and syringols, about 50 wt. % for birch wood lignin), followed by hydroprocessing of these monomers into alkylphenols. These alkylphenols are catalytically dealkylated into phenol and olefins (20 wt. % and 9 wt. % based on lignin intake, respectively). Compared to the reported work, this work produces not only phenol in high yield, but also biopropylene started from inplanta lignin. Importantly, the most recalcitrant and abundant syringyl unit, containing two methoxy substituents, can also be converted into phenol, which has not been investigated in the literature. Alternatively, the alkylphenols undergo further hydroprocessing towards n-propylbenzene (6-30 wt. % based on lignin intake). Compared to the reported work, this work produces not only n-propylbenzene in high yield, but also with stable catalysis. Besides, the more recalcitrant propylsyringol can be converted into n-propylbenzene, which has not yet been reported in the literature.

Though conversion of guaiacol and anisole has been extensively studied,[54] only a few reports investigated hydroprocessing of 4-PG (4-propylguaiacol) and 4-PS (4-propylsyringol). Most of the prior art studies have aimed at (alkyl)cyclohexane and (alkyl)benzene production—as fuel and BTX (xylene) substitutes. However, production of alkylphenols was much less pursued.[54, 55] Moreover, these reports focus on model compounds, while conversion of real lignocellulose-derived phenols is sporadically reported. For example, active carbon supported molybdenum oxide catalysts can convert 4-PG to 4 n propylphenol at 320° C. under 30 bar H2.56 However, unsatisfied results were obtained for hydroprocessing of 4-PS, which is the most abundant monomer in the lignin-oil of the present work. Recently, magnetic Co—Fe@N-doped carbon catalysts were investigated for hydroprocessing of eugenol, achieving 88% selectivity to 4-n-propylphenol. Although this catalyst was applied to lignin-first bio-oil, the mass yield of 4-n-propylphenol is less than 70% of theoretical yield.57 This is also likely due to the large amount (>65 wt. %) of recalcitrant 4-PS (containing two methoxyl groups). Moreover, the reaction was conducted for a very long time (>8 h) at 250° C. with a low concentration of monomers (<1%). $Au/Nb_2O_5$ is capable of converting 4-PG to n propylphenols with ca. 80% yield in water at 300° C. (>8 h) under 65 bar H2.58 However, the main product from 4-PS is n-propylresorcinol over $Au/Nb_2O_5$ rather than n-propylphenols. In addition, all above mentioned reactions were conducted in batch reactors with long reaction times. From an engineering viewpoint, hydroprocessing in a fixed-bed reactor is more desirable.

Hydrodesulfurization catalysts like sulfided $NiMo/Al_2O_3$ are able to transform PG into n-propylphenol isomers in continuous liquid-phase,[15, 59, 60] but product contamination by sulfur—from co-fed CS2 or $H_2S$ to maintain high activity—remains a major disadvantage. Also, for economic reasons, it would be more desirable to hydroprocess without solvent to avoid the separation issues. Pt/C is demonstrated for hydroprocessing of 4-PG towards 4-n-propylphenol in gas phase. However, hydroprocessing of PS to 4-n-propylphenol was not achieved over Pt/C.[61] Therefore, although selective transformation of 4-PG to 4-n-propylphenol has been achieved in these few studies, selective hydroprocessing of 4-PS to 4-n-propylphenol is still a challenge and not reported yet. The unfulfilled 4-PS to 4-n-propylphenol will disable the catalytic funnel approach proposed here.

Hence, a solvent- and sulfur-free, continuous catalytic gas-phase hydroprocessing step was pursued, which is able to selectively funnel real lignocellulose-derived methoxyalkylphenols (including 4-PG, 4-PS, and crude lignin monomers) into alkylphenols in a scalable fixed-bed setup. Besides, further hydroprocessing of the alkylphenols intermediates, thus enabling the selective conversion of lignin monomers into n-propylbenzene is not yet reported with both selective and stable catalysis. Considering the thermodynamic equilibrium between n-propylbenzene and n-propylcyclohexane, it is favored to conduct it at low pressure and high temperature, which suggests gas phase reaction.

Previous reports have demonstrated stable continuous gas-phase dealkylation of pure 4-n-propyl- and 4-ethylphenol to phenol and olefins over a commercial microporous ZSM-5 zeolite.[62] however, gas-phase dealkylation of 3-ethylphenol cannot be realized by microporous ZSM-5.[63] Given the complexity (e.g., impurity and presence of bulky molecules) of the crude alkylphenol stream (Table 4), it can be foreseen that similar use of commercial ZSM-5 will be inadequate.

BRIEF SUMMARY

This disclosure solves the problems of the related art that the practical benefits of yielding high-value chemicals from lignin (an alkylphenolic biopolymer) are challenging due to its inherent recalcitrance and heterogeneity and that high value functionalized aromatics, such as phenol are among the most-suggested chemicals from lignin, but that product yields on lignin weight basis are very low. In addition, next to phenol, also low MW highly functionalized phenolic oligomers, propylene and a processable carbohydrate pulp are produced by this process. Besides, production of n-alkyl chain substituted aromatic hydrocarbon is a challenge for traditional oil refinery. Moreover, conversion of lignin to n-propylbenzene with selective and stable catalysis is a challenge due to the recalcitrant properties of lignin (monomers).

In accordance with the purpose of this disclosure, as embodied and broadly described herein, this disclosure is broadly drawn to a lignocellulose biorefinery process that produces a carbohydrate pulp and convert lignin into small molecules and oligomers, whereby the process involves 1) reductive catalytic fractionation (biomass fractionation with lignin depolymerization) of lignocellulose, 2) forming a lignin oil comprising a monomer and oligomer fraction, 3) separating the monomer and oligomer fraction through liquid-extraction, 4) further converting of the monomer fraction by gas-phase hydroprocessing over metal catalysts into a monomer fraction rich in alkylphenols, which can be either 5) dealkylated over an acidic zeolite, or 6) further hydroprocessed to deoxygenated aromatics.

In one aspect of, disclosed is a lignocellulose biorefinery process that produces a carbohydrate pulp and converts lignin into small molecules and oligomers, whereby the process comprising the following steps: a) subjecting a lignocellulose mass in contact with a metal catalyst, $H_2$ and an organic solvent to reductive catalytic fractionation to produce a carbohydrate pulp and a liquid, b) solvent evaporation from the liquid to obtain lignin oil, hereby recycling the solvent for reuse in step a, and recycling $H_2$ and formed methane for reuse in step d. c) contacting the lignin oil to a two-step liquid extraction with first $H_2O$ and $CH_2Cl_2$ or ethylacetate to isolated 1) a sugar water stream, and subsequently an extraction of the sugar-free lignin oil with an alkane solvent, such as hexane, heptane or octane, whereby are separated 2) lignin oligomers and 3) lignin monomers, d) hydroprocessing the lignin monomers by bringing the lignin monomers in contact with the gas stream from step b, comprising $H_2$ and methane, in a process to generate a stream comprising alkylphenols methane, $H_2O$, $H_2$, e) subjecting the stream from step d rich in alkylphenols to a dealkylation process to generate a stream comprising phenols, alkenes in $CH_4$, $H_2O$ and $H_2$ and f) separating and purifying the stream from step e to obtain a phenol fraction and a propylene fraction and an organics water fraction. Alternatively, the alkylphenols produced in step d are further hydroprocessed into n-propylbenzene.

Another aspect of this disclosure is a lignocellulose biorefinery process that produces a carbohydrate pulp and converts lignin into small molecules, whereby the process involves the following steps 1) first, crude lignin-oil and pulp are produced by reductive catalytic fractionation (RCF) in either batch or (semi-)continuous modus, followed by liquid/solid separation and solvent evaporation, 2) solubilized sugars in the lignin oil are isolated in a liquid-liquid extraction unit 3) lignin monomers are isolated from the refined lignin oil (step 2) through extraction with an alkane solvent. 4) the extract is subjected to flash distillation to remove the extraction solvent from the lignin monomers; 5) the crude monomer extract (monomers fraction), together with a $H_2$-gas stream, such as the gas stream from reductive catalytic fractionation, containing amongst others methane impurities (from methane formation during RCF) are fed into the gas-phase fixed-bed setup, containing Ni catalyst to form alkylphenols (i.e., hydroprocessing) 6) this alkylphenolics crude, containing water hydrogen and methane impurities is fed without intermediate purification to the second fixed-bed reactor for conversion to phenol and olefins over an acidic zeolite, preferably belonging to the pentasil family of zeolites, and preferably a hierarchical zeolite, preferably a hierarchical ZSM-5 zeolite, whereof preferably the hierarchical version of a parent ZSM-5 zeolite with high Si/Al ratio such as 140 7) product separation is carried out in a gas-liquid separator, producing a liquor of phenol, and a gaseous mixture of water, olefins, $H_2$ and $CH_4$. Alternatively the crude monomer extract from step 5) is fed into the gas-phase fixed-bed setup, containing Platinum catalyst to form alkylphenols and subsequently n-propylbenzene.

Further scope of applicability of this present disclosure will become apparent from the detailed description given hereinafter. However, it should be understood that the detailed description and specific examples, while indicating preferred embodiments of this disclosure, are given by way of illustration only, since various changes and modifications within the spirit and scope of this disclosure will become apparent to those skilled in the art from this detailed description. It is to be understood that both the foregoing general description and the following detailed description are exemplary and explanatory only and are not restrictive of this disclosure, as claimed.

BRIEF DESCRIPTION OF THE DRAWINGS

This disclosure will become more fully understood from the detailed description given herein below and the accompanying drawings, which are given by way of illustration only, and thus are not limitative of this disclosure, and wherein:

FIG. 3A: Influence of different metal catalysts (285° C. and 4.5 $h^{-1}$ WHSV, unless indicated otherwise). FIG. 3B: Influence of different nickel catalysts (285° C., unless indicated otherwise). FIG. 3C: Gas chromatograms of conversion of 4-n-propylguaiacol over 17 wt. % $Ni/Al_2O_3$ and 64 wt. % $Ni/SiO_2$ (at similar conversion, ca. 62%). Reaction conditions: 1 bar of total pressure (0.4 bar $H_2$ partial pressure). The data are taken at time-on-stream of 5 h.

FIG. 4A: Activity of nickel catalyst (PG at 285° C. with low conversion<20%, time-on-stream of 3 h). FIG. 4B: Selectivity to PPs versus PG conversion (285° C. at different WHSV). FIG. 4C: Evolution of conversion and products selectivity with time-on-stream over 64 wt. % $Ni/SoO_2$ (PG at 285° C. and 6.0 $h^{-1}$ WHSV). FIG. 4D: Different lignin-derived phenolics (over 64 wt. % $Ni/SiO_2$: EG, PG, isoeugenol and pine-derived monomers at 285° C. and 8.2, 6.0, 4.4 and 6.0 $h^{-1}$ WHSV, respectively; PS(I), PS(II) and birch-derived monomers at 305° C. and 7.1, 5.3 and 5.3 $h^{-1}$ WHSV, respectively). Constant reaction conditions: 1 bar of total pressure (0.4 bar $H_2$ partial pressure). The data in FIGS. 4B and 4D are taken at time-on-stream of 5 h.

FIG. 6A: Conversion rate of n-propylbenzene and selectivity to benzene and propylene as a function of temperature (ramping rate=1° C. $min^{-1}$, no water); FIG. 6B: The products distribution as a function of temperature (ramping rate=1° C. $min^{-1}$, no water); FIG. 6C: Gas chromatogram at low and high temperature (conversion); Conversion of n-propylbenzene as a function of time-on-stream (TOS) over (FIG. 6D) Z140-H (410° C.) and (FIG. 6E) Z12-P (350° C.) without water. WHSV=3.2 $h^{-1}$. In FIG. 6B others include toluene, ethylene, and some unidentified products, 1 bar.

FIG. 7A: Conversion of cresols and selectivity to phenol in the conversion of cresols over Z140-H; FIG. 7B: The catalytic stability of Z140-H in the conversion of cresols. Isomerization was used as the criterion for measuring the stability; FIG. 7C: The conversion of cresols and selectivity to phenol in the conversion of cresols over Z40-P (Si/Al=40); FIG. 7D: Gas chromatogram of cresols conversion over Z40-P; FIG. 7E: The conversion of cresols and selectivity to phenol in the conversion of cresols over USY-40 (Si/A=40); FIG. 7F: Gas chromatogram of cresols conversion over USY-40. Selectivity (%)=yield of products/theoretical yield×100%. Ramping rate=1° C. $min^{-1}$ in FIGS. 7A, 7C, and 7E. Temperature in FIG. 7B is 410° C., temperature in FIGS. 7D and 7F is 470° C. 2.9 g $h^{-1}$ WHSV, molar ratio of $H_2O$ to 4-methylphenol=6, 1 bar.

FIG. 9A: Mass balance of this integrated biorefinery (assuming the conversion of 1 ton birch wood); FIG. 9B: Mass balance of monomers conversion (1 ton birch wood basis). The amount of hydrogen and methanol in the scheme is the consumed amount and not the loaded ones.

In FIG. 12A, others include cresols, alkylbenzenes, and some unidentified products. Reaction conditions: WHSV=3.7 $h^{-1}$, molar ratio of $H_2O$ to 4-n-propylphenol is 6, 1 bar. Since 4-n-propylphenol undergoes not only dealkylation but also isomerization (FIG. 12A), and all isomers can be dealkylated, the reported conversion rate and conversion in FIGS. 12C and 12D are based on the conversion of all isomers.

FIG. 13A: The products distribution as a function of temperature, ramping rate=1° C. $min^{-1}$; FIG. 13B: Gas chromatogram at low and high temperature (conversion); FIG. 13C: Conversion of ethylphenols and selectivity to phenol and ethylene as a function of time-on-stream (TOS) at 420° C.; In FIG. 13A others include cresols, alkylbenzenes, and some unidentified products. Reaction conditions: 3.3 $h^{-1}$ WHSV, molar ratio of $H_2O$ to 4-ethylphenol is 6, 1 bar. Since 4-ethylphenol undergoes not only dealkylation but also isomerization (FIG. 13A), and all isomers can be dealkylated, the reported conversion in FIG. 13C is the conversion of all isomers.

DETAILED DESCRIPTION

Figure 1:
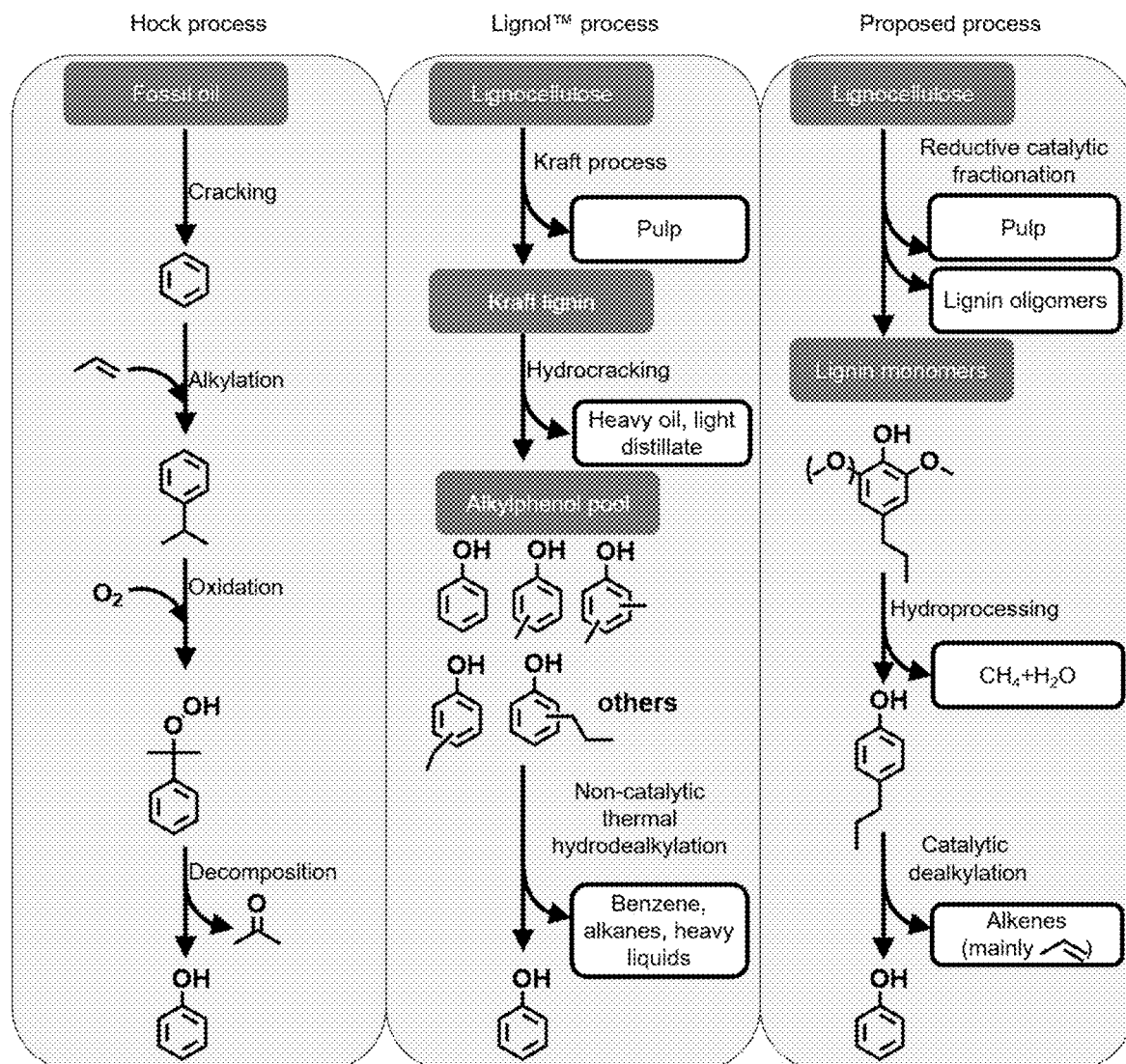
FIG. 1. Routes to phenol from (i) fossil oil by the current industrial Hock process, (ii) technical (isolated) lignin by the Lignol™ process, and (iii) in planta lignin by the proposed process.
Figure 2:
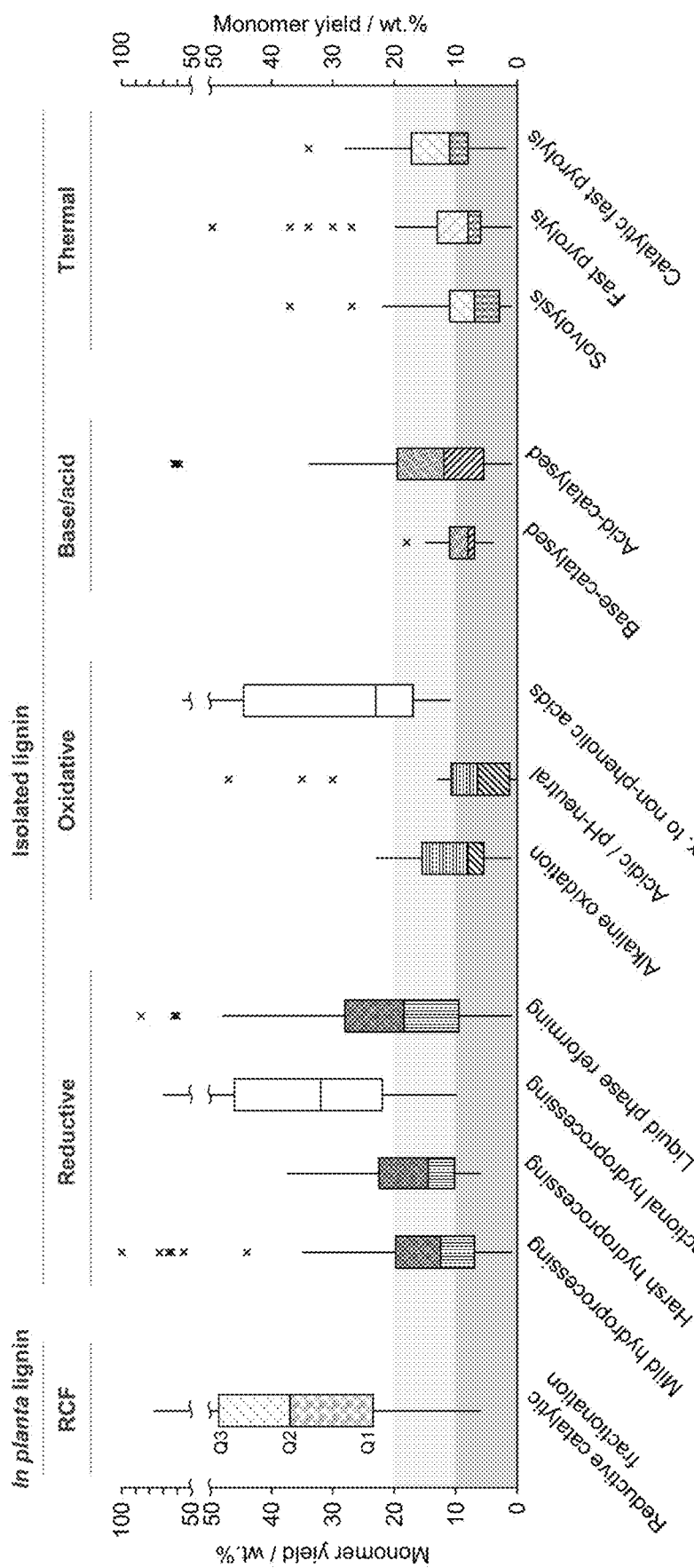
FIG. 2. Box plots showing the distribution of monomer yields for different lignin depolymerization methods. Methods that do not yield phenolic compounds are indicated in white. These include bifunctional hydroprocessing, which targets alkanes, and oxidation to non-phenolic acids, which yields small carboxylic acids (e.g., formic acid, acetic acid) and dicarboxylic acids (e.g., succinic acid).

The following detailed description of this disclosure refers to the accompanying drawings. The same reference numbers in different drawings identify the same or similar elements. Also, the following detailed description does not limit this disclosure. Instead, the scope of this disclosure is defined by the appended claims and equivalents thereof.

The following detailed description of this disclosure refers to the accompanying drawings. The same reference numbers in different drawings identify the same or similar elements. Also, the following detailed description does not limit this disclosure. Instead, the scope of this disclosure is defined by the appended claims and equivalents thereof.

Several documents are cited throughout the text of this specification. Each of the documents herein (including any manufacturer's specifications, instructions etc.) are hereby incorporated by reference; however, there is no admission that any document cited is indeed prior art of the present invention.

The present invention will be described with respect to particular embodiments and with reference to certain drawings but this disclosure is not limited thereto but only by the claims.

The drawings described are only schematic and are non-limiting. In the drawings, the size of some of the elements may be exaggerated and not drawn to scale for illustrative purposes. The dimensions and the relative dimensions do not correspond to actual reductions to practice of this disclosure.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of this disclosure described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of this disclosure described herein are capable of operation in other orientations than described or illustrated herein.

It is to be noticed that the term "comprising," used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to the devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of this disclosure, various features of this disclosure are sometimes grouped together in a single embodiment, figure, or description thereof for the purpose of streamlining the disclosure and aiding the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment.

Thus, the claims following the detailed description are hereby expressly incorporated into this detailed description, with each claim standing on its own as a separate embodiment.

Furthermore, while some embodiments described herein include some but not other features included in other embodiments, combinations of features of different embodiments are meant to be within the scope of this disclosure, and form different embodiments, as would be understood by those in the art. For example, in the following claims, any of the claimed embodiments can be used in any combination.

In the description provided herein, numerous specific details are set forth. However, it is understood that embodiments of this disclosure may be practiced without these specific details. In other instances, well-known methods, structures and techniques have not been shown in detail in order not to obscure an understanding of this description.

Other embodiments of this disclosure will be apparent to those skilled in the art from consideration of the specification and practice of this disclosure disclosed herein.

It is intended that the specification and examples be considered as exemplary only.

Each and every claim is incorporated into the specification as an embodiment of the present invention. Thus, the claims are part of the description and are a further description and are in addition to the preferred embodiments of the present invention.

Each of the claims set out a particular embodiment of this disclosure.

The following terms are provided solely to aid in the understanding of this disclosure.

Definitions

A "small molecule" is broadly used herein to refer to an organic compound typically having a molecular weight of less than about 250

"Oligomers" are broadly used herein to refer to organic compounds, obtained after lignin depolymerization, typically having a molecular weight between 250-5000 g/mol.

DESCRIPTION

Production of chemicals is rapidly becoming the single largest driver of global oil consumption in the future.[1, 2] To reduce the oil consumption and the resulting greenhouse gas emission, a shift from non-renewable fossil to renewable carbon resources is required.

Lignocellulose, as an abundant feedstock of renewable carbon, can be used for production of bio-fuels, bio-chemicals and bio-materials.[3, 4] However, most of the proposed lignocellulose biorefineries cannot economically compete with oil refineries due, in part, to incomplete utilization of feedstock. Therefore, it is imperative to maximize feedstock utilization to be not only cost but also environmentally competitive with fossil oil-based processes.[5] There is thus a need for new integrated biorefinery concepts that offer biomass refining with low energy requirements and high feedstock utilization (carbon and mass) efficiency, providing multiple products stream into markets. The inherent heterogeneity of lignocellulose, comprising entangled sugar-based (i.e., (hemi-cellulose) and aromatic (i.e., lignin) biopolymers, complicates its valorization into high value products. In particular, production of high value chemicals from lignin—a methoxylated phenylpropanoid biopolymer—is challenging due to its inherent recalcitrance and heterogeneity.[6-9] In contrast to relatively oxygen-free fossil oil, oxygen-containing functional groups are plentiful in lignocellulose. Therefore, functionalized aromatics, such as phenol are among the most suggested chemicals from lignin, but product yields on lignin weight basis are currently low. Hence, an integrated lignocellulose biorefinery was invented that simultaneously produces phenol, propylene, and phenolic oligomers from in planta wood lignin, and a carbohydrate pulp, with an overall carbon efficiency of up to 76% and mass efficiency of up to 78%.

The first step of our approach rests on a specific type of lignin-first biorefining, termed reductive catalytic fractionation (RCF).[14, 45, 64-66] RCF of lignocellulose yields a solid carbohydrate pulp and a lignin-oil by cleavage of ester and ether bonds as a result of tandem high-temperature solvolysis, hydrogenation and hydrogenolysis either in batch or in (semi-)continuous mode over a metal catalyst in the presence of a reducing agent, such as hydrogen. The general consensus is that stabilization of the reactive intermediates formed by depolymerization of in planta lignin prevents the formation of unreactive condensed lignin derivatives.[14] Near-complete delignification of hardwoods, such as birch and poplar, can be achieved without significant carbohydrate degradation.[45] Besides low molecular weight oligomers, the lignin-oil contains few phenolic monomers in close-to-theoretical yields, viz. 50 wt. % for hardwoods.[45] However, maximal valorization of this lignin-oil into high value products, such as phenol or other aromatics, by technology that is not only profitable but, most importantly sustainable, has not yet been demonstrated, and is key in demonstrating the potential of biorefineries.

The high degree of delignification for hardwoods toward phenolic monomers enables us to propose an integrated process for transformation of wood lignin to phenol and propylene. Typical phenolic monomers composition (50.5 wt. % on lignin basis, Table 3) of RCF, from birch wood in MeOH over commercial Ru/C, shows 4-n-propylguaiacol (PG; 19 wt. %) and -syringol (PS; 67 wt. %), besides few others like 4-ethylguaiacol (EG) and -syringol as major products. While alkyl is the main substituent of the guaiacol/syringol monomers, considerably more polar groups containing primary alcohols remain in the oligomers structure. This polarity difference facilitates their practical separation; a simple extraction in n-hexane under reflux allows the isolation of the phenolic monomers. This work demonstrates that a less than six-fold mass of n-hexane to lignin-oil cost-efficiently extracts more than 90 wt. % of the phenolic monomers, and is therefore selected as the optimum trade-off between extraction efficiency, solvent usage, and oligomer co-extraction. Further (costly) separation of the individual phenolic monomers is not necessary as the crude will be completely funneled to phenol and propylene, or to n-propylbenzene.

Figure 3A:
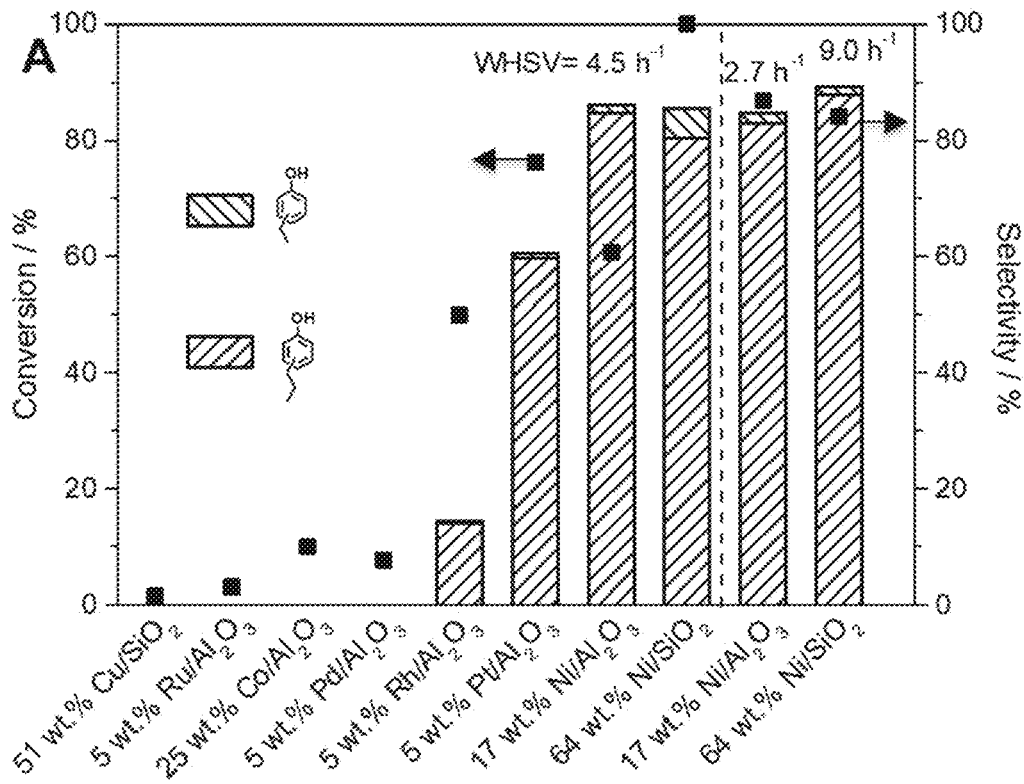
FIGS. 3A-3C. Hydroprocessing of 4-n-propylguaiacol to n-propylphenols and ethylphenols.
Figure 3B:
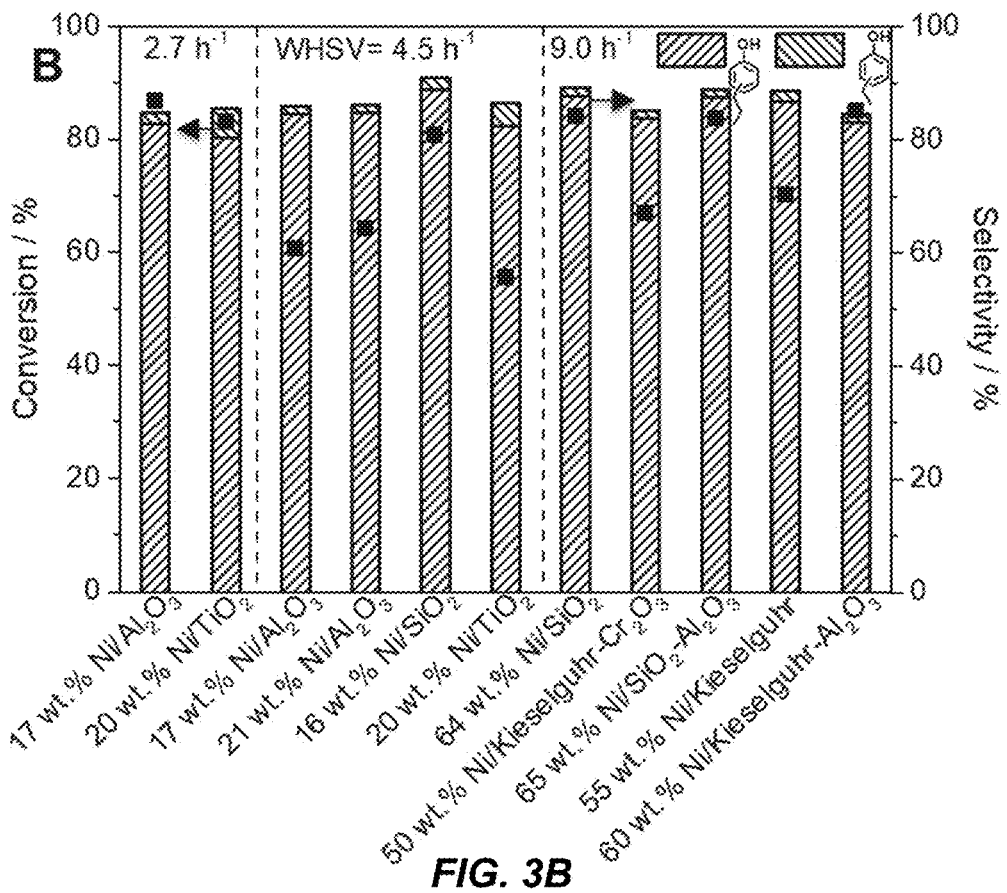
Figure 3C:
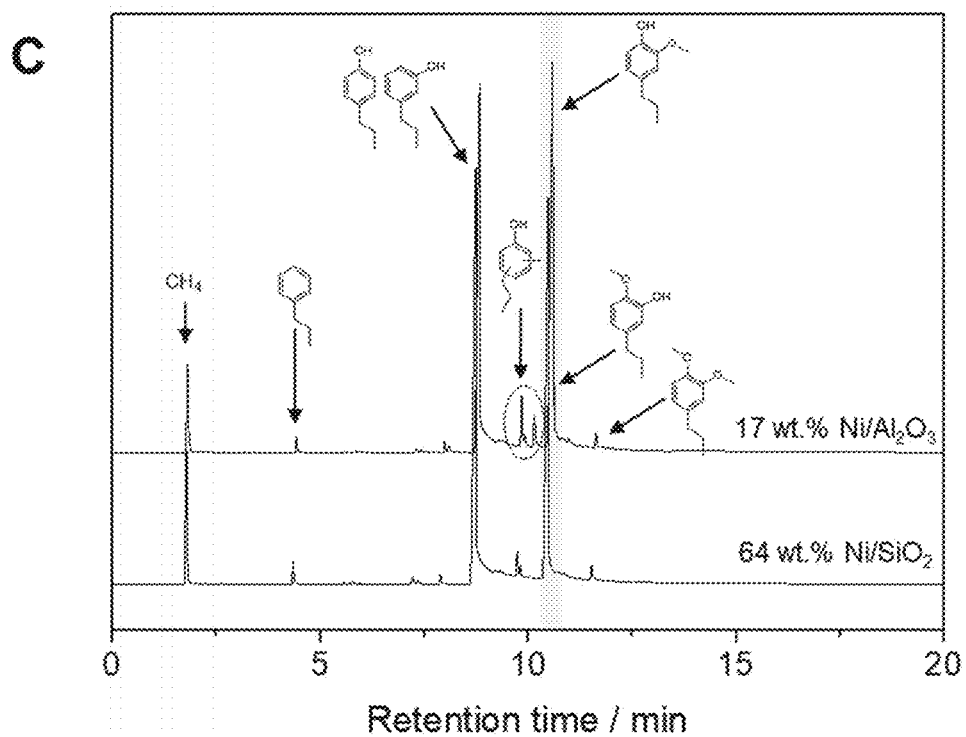
Figure 4A:
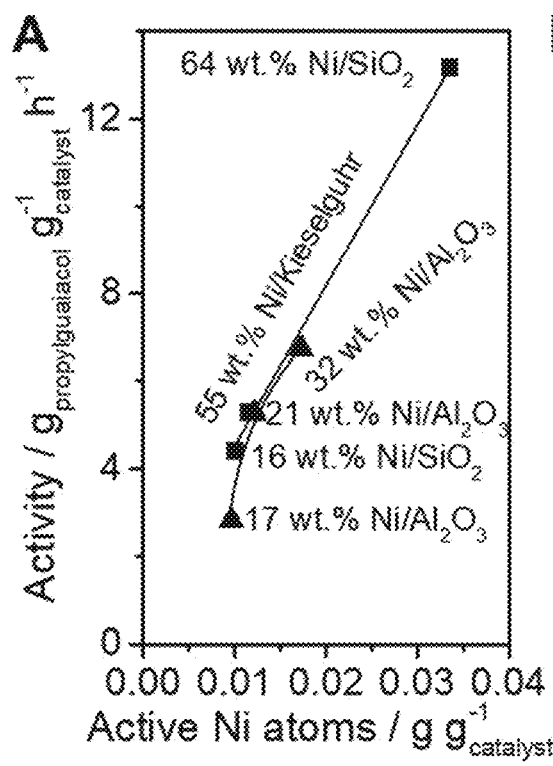
FIGS. 4A-4D. Catalytic evaluation of the hydroprocessing step to funnel lignin-derived monomers toward few alkylphenols.
Figure 4B:
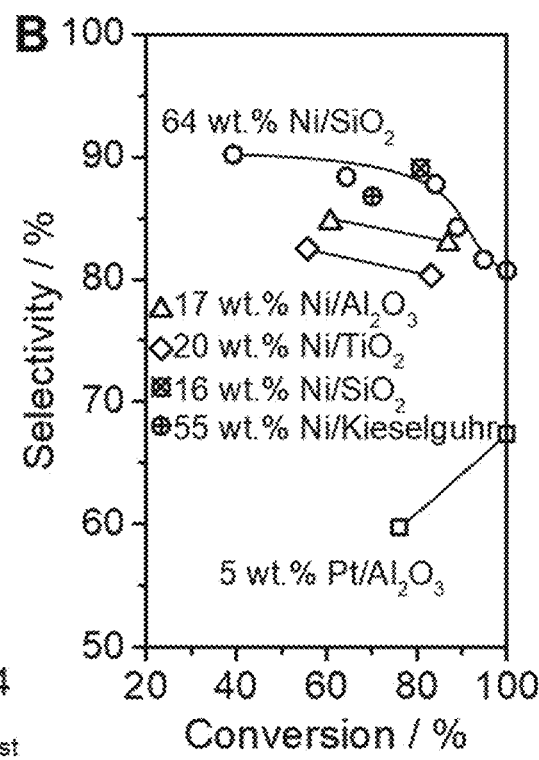

The next step in our integrated refinery is hydrotreating of the monomers stream into n-propylphenols and ethylphenols, and optionally further hydrotreating of these alkylphenols to n-propylbenzene. In contrast to reported (batch) liquid phase approaches or using sulfide catalysts,[15, 59, 60] continuous gas-phase hydroprocessing was conducted without solvent- and sulfur, to avoid product contamination and additional cost due to solvent loss and recovery from the engineering point of view. Hydroprocessing of 4-propylguaiacol—one of the dominant monomers in the lignin-oil—was tested initially to achieve high selectivity to n-propylphenols and ethylphenols. Several commercial catalysts including supported Pt, Pd, Ru, Rh, Cu, Co, Ni catalysts were evaluated under atmospheric pressure with 0.4 bar $H_2$ partial pressure (FIG. 3). Nickel catalyst shows the highest PPs selectivity compared to other metals. The selectivity was not significantly influenced by nickel content (FIG. 3), Ni catalysts that contain high surface nickel are preferred as a result of high activity (FIG. 4A). Catalysts including supported Pt, Pt, Ru, Ni catalysts were evaluated for n-propylbenzene production from propylguaiacol and 4-propylsyringol via n-propylphenol under atmospheric pressure with 0.98 bar $H_2$ partial pressure.

Figure 4C:
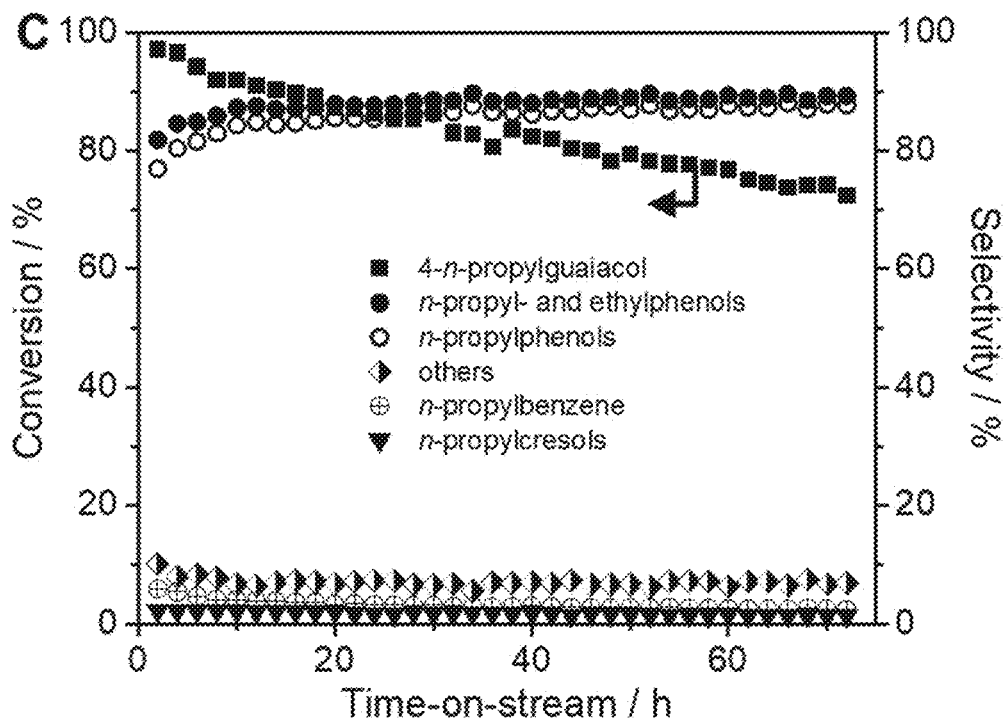

Since acidic supports such as silica/alumina led to more (propyl)cresols—stable compounds (and thus undesired) in the dealkylation step to phenol (FIG. 3)—and redox-active supports like anatase $TiO_2$ form fully deoxygenated products such as n-propylbenzene and n-propylcyclohexane, Ni is preferably supported on inert materials such as silica or carbon. 64 wt. % $Ni/SiO_2$ is thus selected for the rest of this disclosure when targeting selective production of n-alkylphenols. It can achieve 86% yields to n-propylphenols and ethylphenols at 4.5 kg per kg catalyst per hour at optimized conditions. Note that other Ni catalysts can also be used for the hydroprocessing step, but with somewhat lower selectivity. By-products include n-propylbenzene, propylcresols, besides some others such as cresols and propylanisole. The Ni catalyst only shows slight deactivation without loss of the selectivity (FIG. 4C). Alternatively, when targeting the production of n-propylbenzene, through hydrotreating of lignin monomers via n-alkylphenols, $Pt/TiO_2$ is preferred as it shows both high selectivity and stability.

In an alternative embodiment, promoter-modified Ni catalysis or support modification is used to further enhance the catalytic performance in terms of both selectivity and stability. Promoter species such as V, Ce, La, and Mn, could have similar roles in the enhancement of catalytic performance for the Ni-based catalyst supported on silica.

Figure 4D:
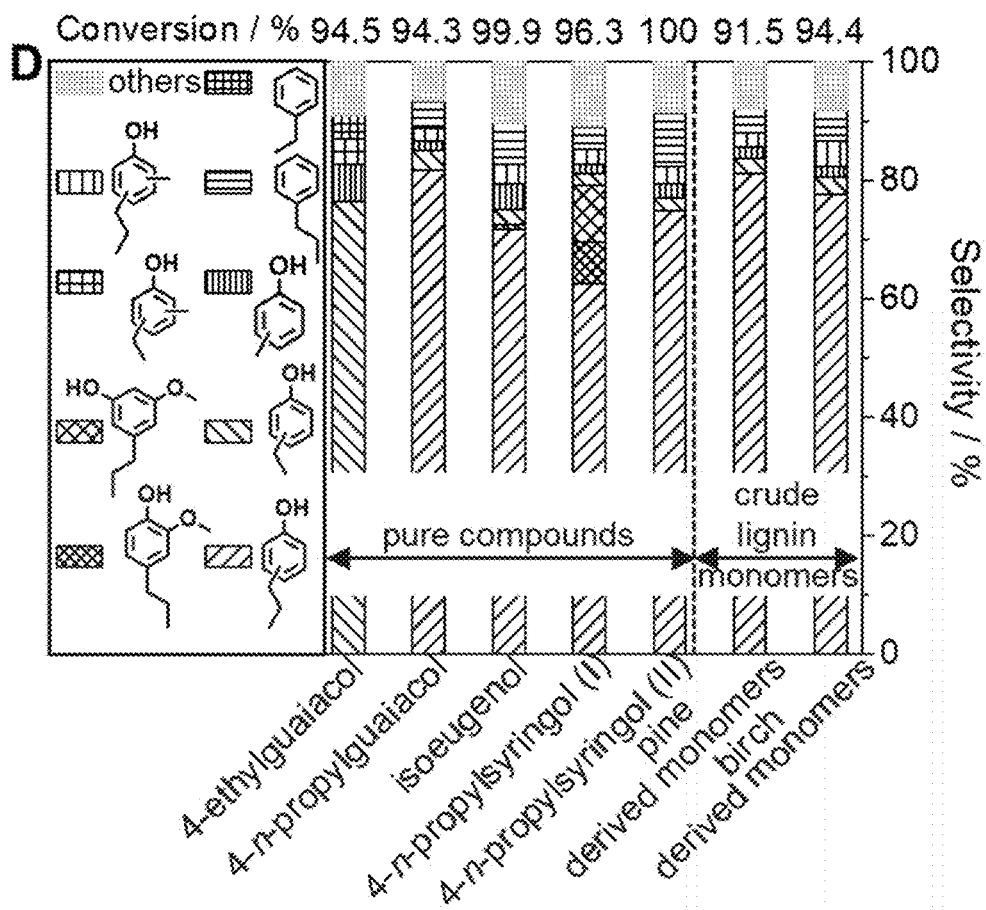

Hydroprocessing of other pure monomers such 4-ethylguaiacol, isoeugenol, 4-propylsyringol were tested next. All compounds can be selectively converted to n-propylphenols and ethylphenol (ca. 80%) at (near) complete conversion (FIG. 4D). Hydroprocessing of 4-propylsyringol to n-propylphenols and ethylphenols needs higher temperature and contact time, showing 77% selectivity at full conversion. Propylguaiacol and 3-methoxyl-5-n-propylphenol are the key intermediates (FIG. 4D). The n-propylphenols were formed by both direct demethoxylation and cascade demethylation/dehydroxylation).

Based on the preceding results of hydroprocessing of pure compounds, hydroprocessing of crude monomers stream (obtained from the extraction) was investigated. The selectivity to n-propylphenols and ethylphenols remain similarly high (ca. 80%) at the same conditions for both softwood and hardwood derived crude monomers stream (FIG. 4D). This demonstrates robustness of the Ni based catalysts for conversion of real biomass feedstock. The hydroprocessing products were condensed at 0-5° C. The liquid product stream contains mainly n-propylphenols and ethylphenols, with minor side products such as (propyl)cresols and n-propylbenzene in addition to water, and this stream is used entirely in the dealkylation step without separation and purification steps.

Figure 5A:
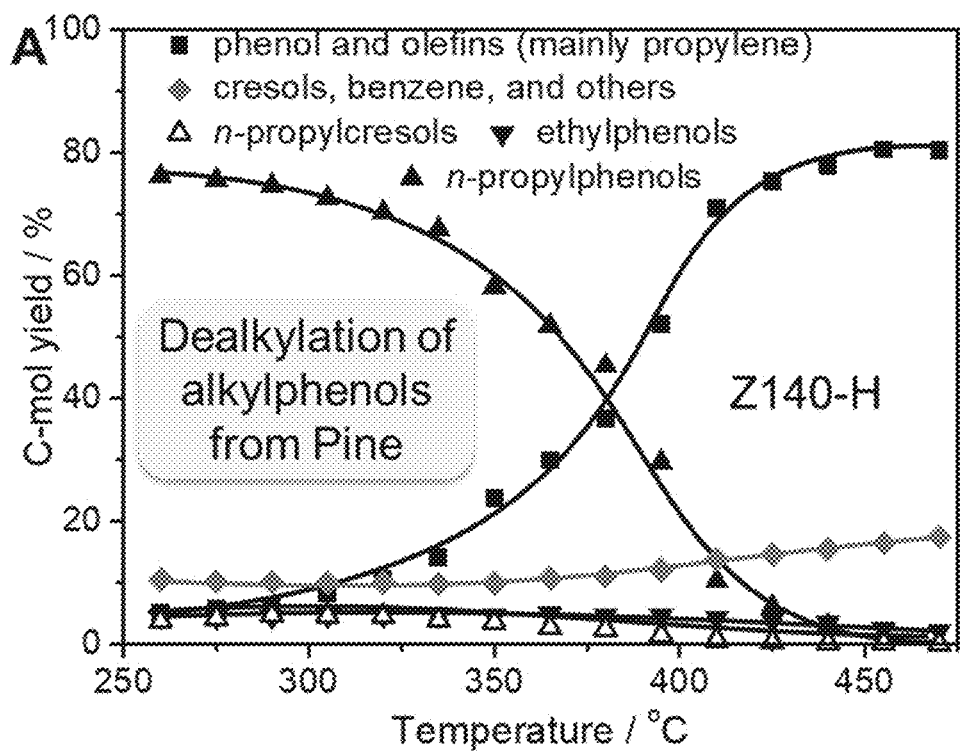
FIGS. 5A-5H. Catalytic evaluation of the dealkylation step to funnel alkylphenols toward phenol and olefins. Dealkylation of the hydroprocessing products from the extracted monomers of pine wood lignin oil over Z140-H (FIG. 5A) at different temperature. Dealkylation of the hydroprocessing products from (FIG. 5B) PG, the extracted monomers of (FIG. 5C) pine and (FIG. 5D) birch wood lignin oils at 410° C. over Z140-H with TOS. Conversion (rate) and selectivity versus (FIG. 5E) temperature and (FIG. 5F) TOS (305° C. and 395° C., respectively) over Z140-H and Z140-P for conversion of isopropylcresols with 4.1 $h^{-1}$ WHSV. Conversion (rate) and selectivity versus (FIG. 5G) temperature and (FIG. 5H) TOS (395° C.) for conversion of n-propylphenols over Z140-H. C-mol yield represents the carbon molar yield in the product stream. Ramping rate is 1° C. $min^{-1}$ in FIGS. 5A, 5E, and 5G. 2.8 and 3.7 $h^{-1}$ WHSV for FIGS. 5D and 5A-5C, 5G-5H, respectively. The theoretical yield (84.5%) in FIG. 5D is the maximum combined yield of phenol and olefins based on the substrate composition.
Figure 5B:
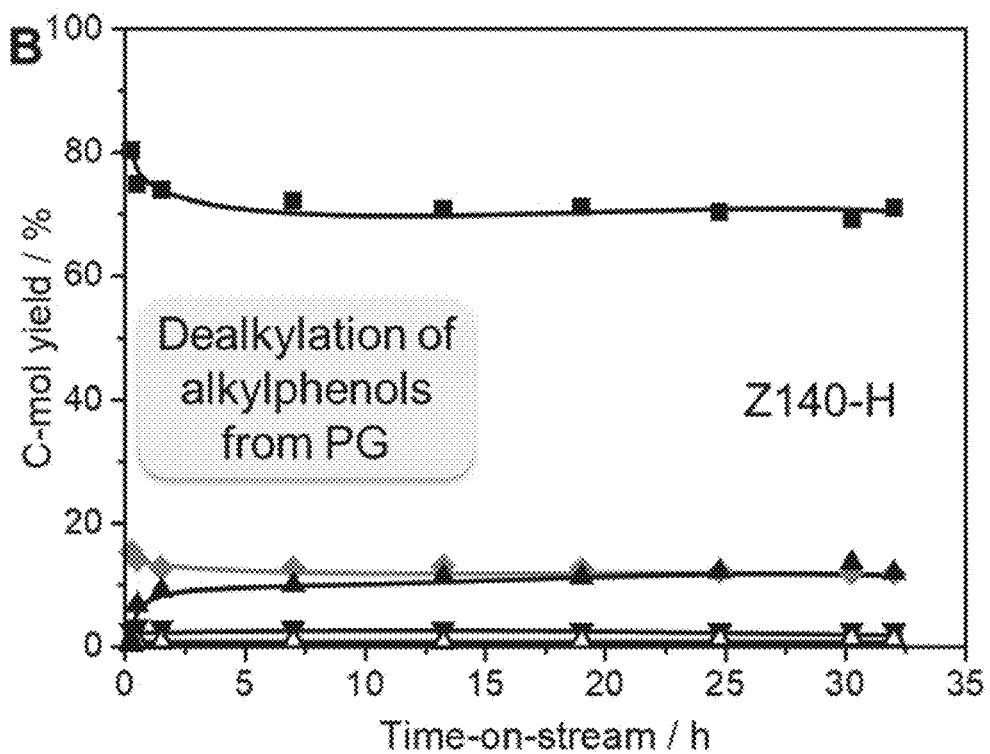
Figure 5C:
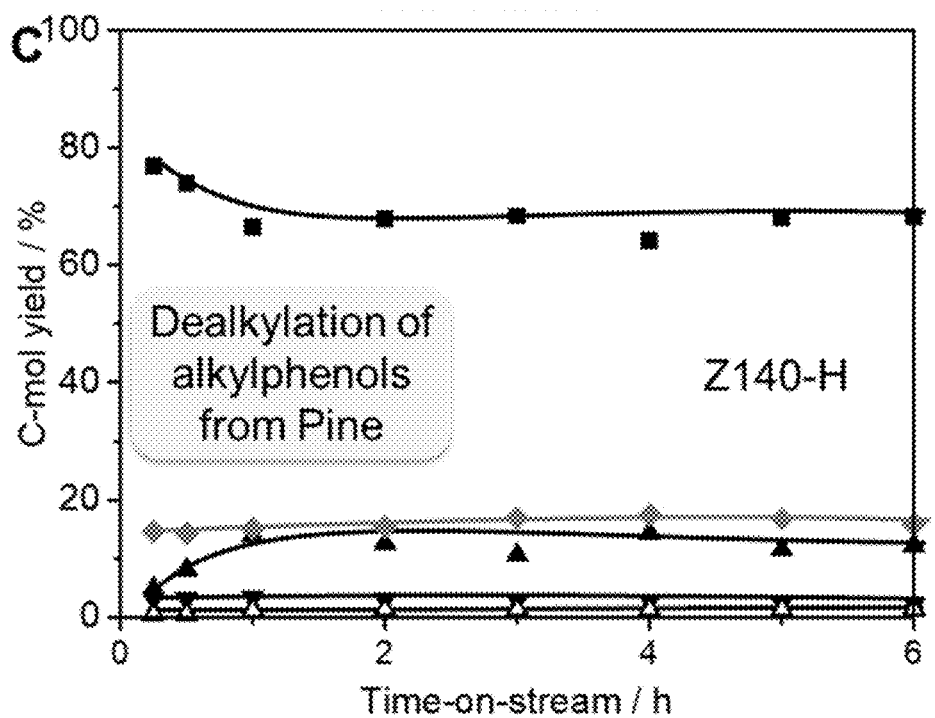
Figure 5D:
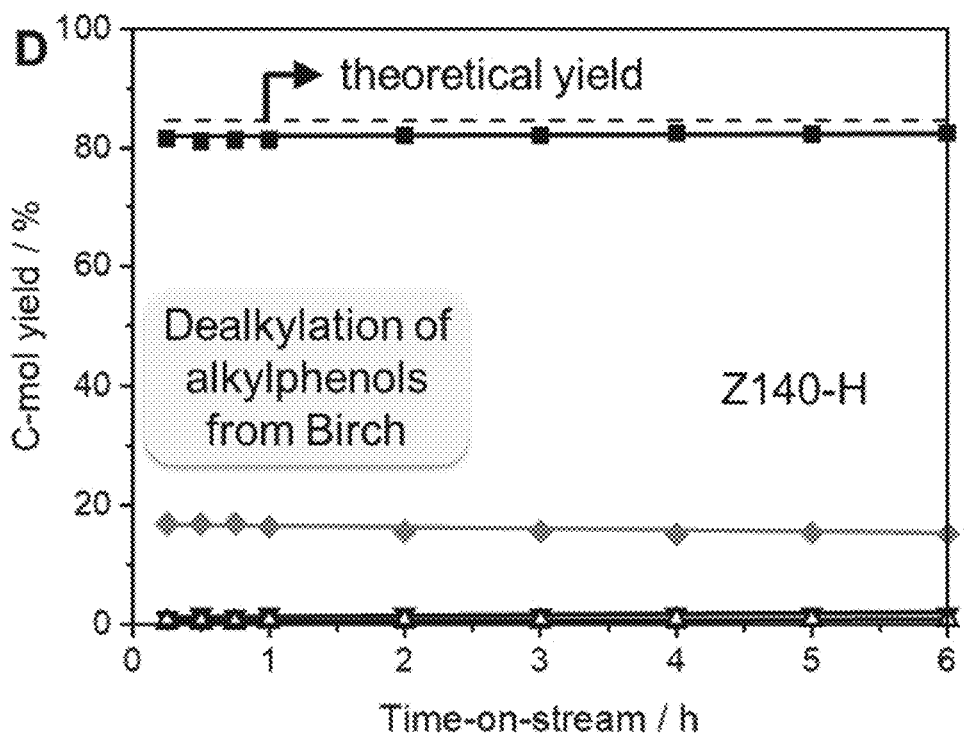

Previous reports proved stable continuous gas-phase dealkylation of pure 4-n-propyl and 4-ethylphenol to phenol and olefins over a commercial microporous ZSM-5 zeolite.[62] Since co-feeding of water was crucial to maintain robust catalytic activity, the presence of water in the crude alkylphenol stream is beneficial for the dealkylation. Given the complexity of the crude alkylphenols stream (Table 4), similar use of commercial ZSM-5 is not preferred. It was reported that microporous ZSM-5 cannot selectively dealkylate 3-ethylphenol into phenol.[63] Sterically demanding alkylphenols, here demonstrated with conversion of 4-isopropyl-3-methylphenol (4-iPMP, model compound of bulky molecules—propylcresols—in the crude alkylphenols), are indeed harder to convert due to pore restriction. Besides, it was reported that presence of n-propylbenzene leads to microporous ZSM-5 deactivation due to coking.[67] To address the site-access restriction and cokes formation, hierarchical ZSM-5 catalysts (such as Z140-H) with balanced network of micro- and mesopores are preferred. High phenol and propylene (ethylene) yields from the crude alkylphenols streams were achieved under stable continuous catalytic operation (FIG. 5). FIGS. 5A-5D display the near-quantitative and selective conversion of the crude alkylphenols to produce 82% phenol and propylene (ethylene) stream. Stability of Z140-H is demonstrated, deliberately performed at incomplete conversion, not only for model compounds, but also for biomass-derived crude stream (FIGS. 5A-5D). Side-products are cresols, benzene, and trace amount of some others (FIG. 5D).

Figure 5E:
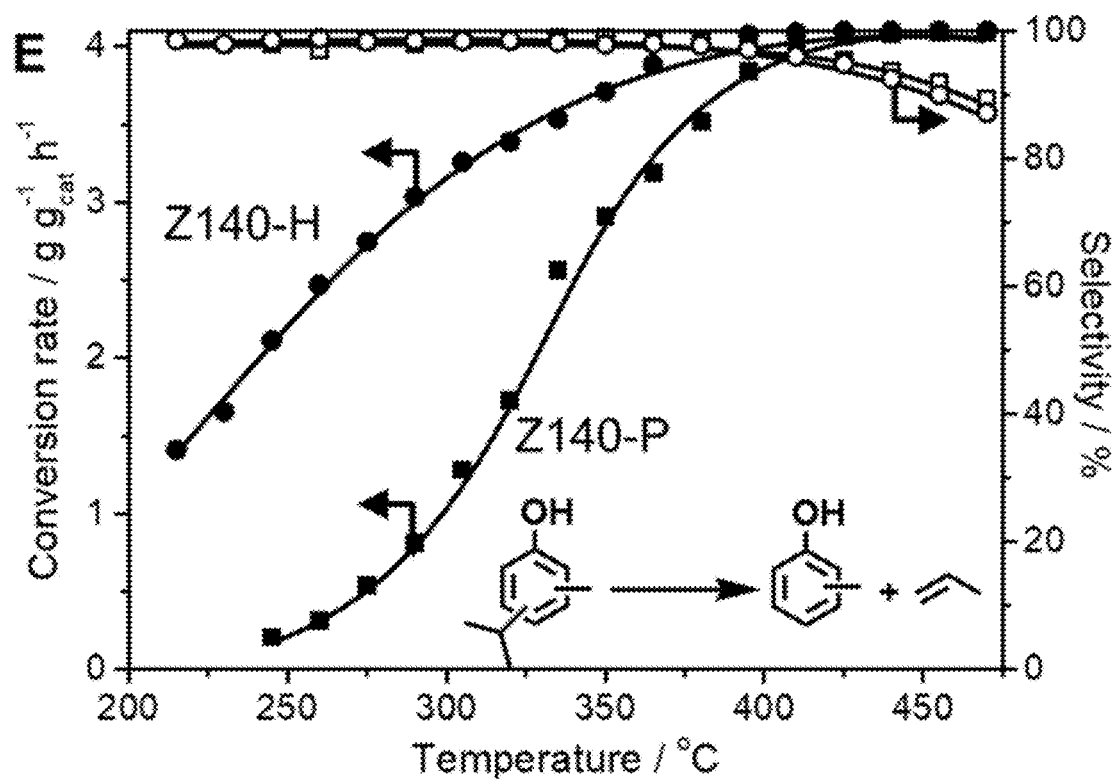
Figure 5F:
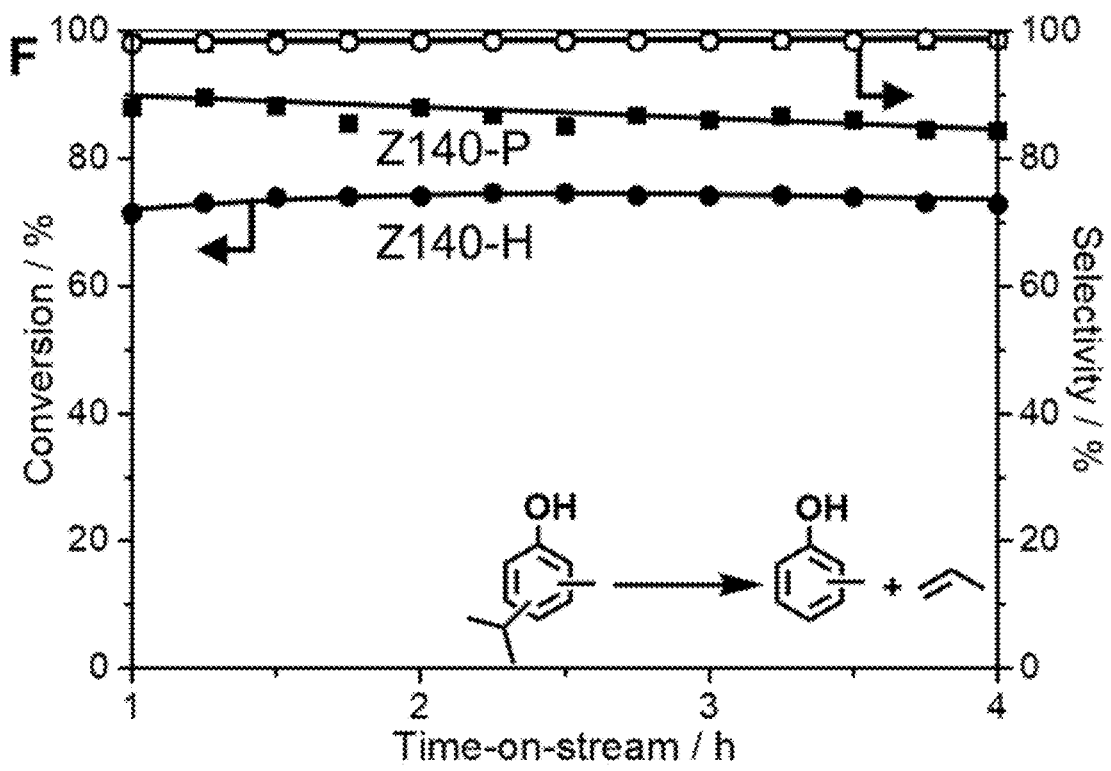

Detailed kinetic studies (using model substrates) demonstrated that tuning of pore structure is indeed highly preferred to maximize the products yield and catalysts life time. This is illustrated for conversion of sterically hindered 4-iPMP; Z140-H clearly outperforms commercial ZSM-5 catalyst (ZSM-5-P) regarding conversion rate (4.1 kg per kg catalyst per h, 380° C.), selectivity to the corresponding phenol and propylene (≥97%), and stability (FIGS. 5E-5F).

Figure 5G:
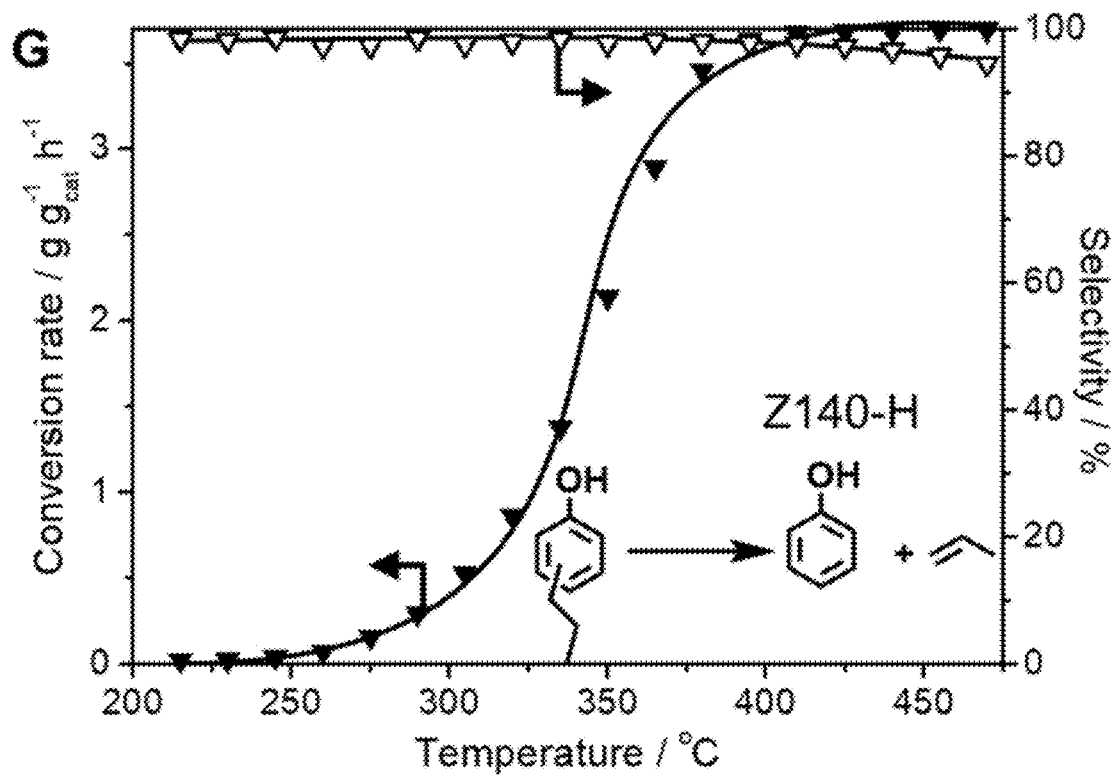
Figure 5H:
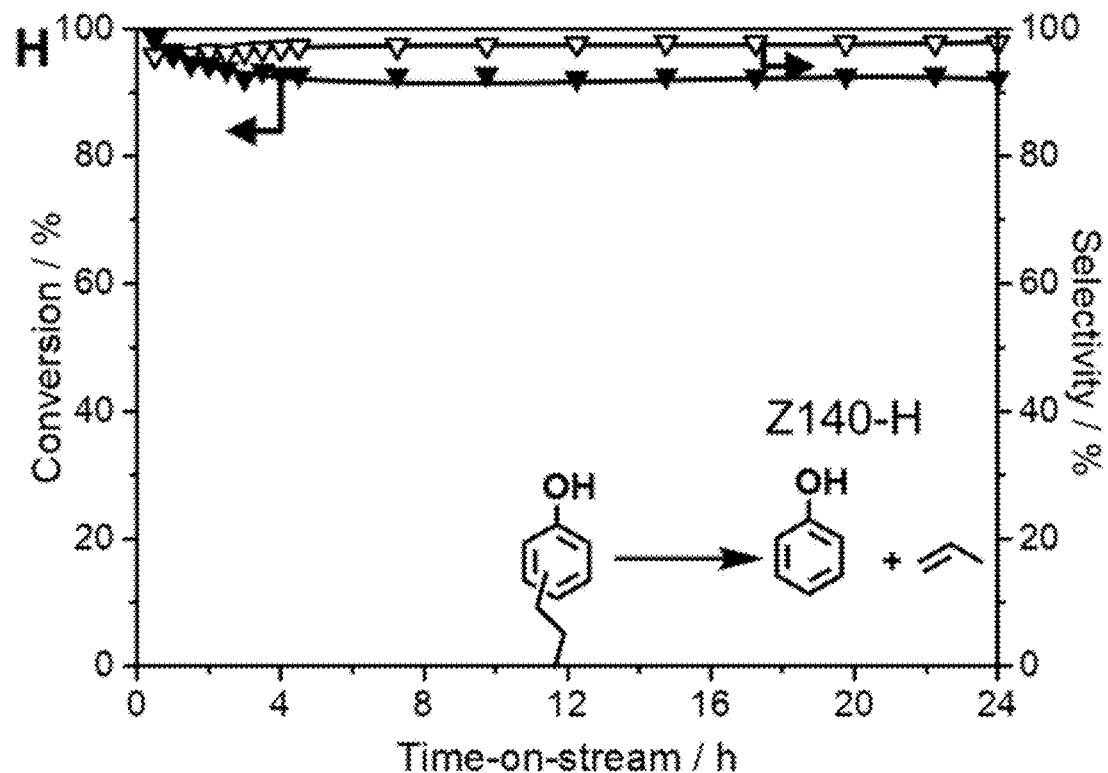
Figure 6A:
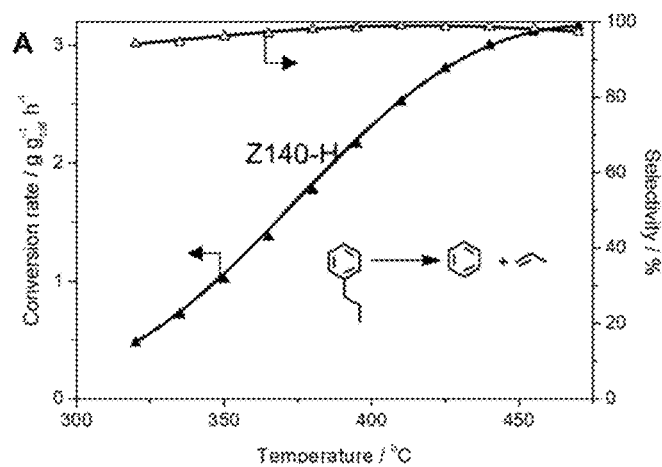
FIGS. 6A-6E. Dealkylation of n-propylbenzene over Z140-H.
Figure 6B:
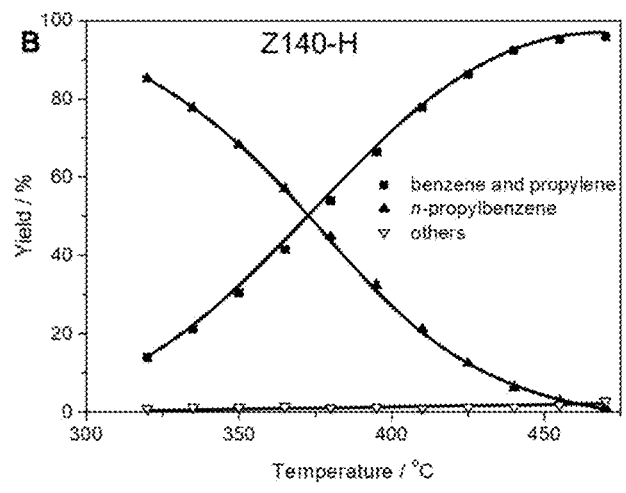
Figure 6C:
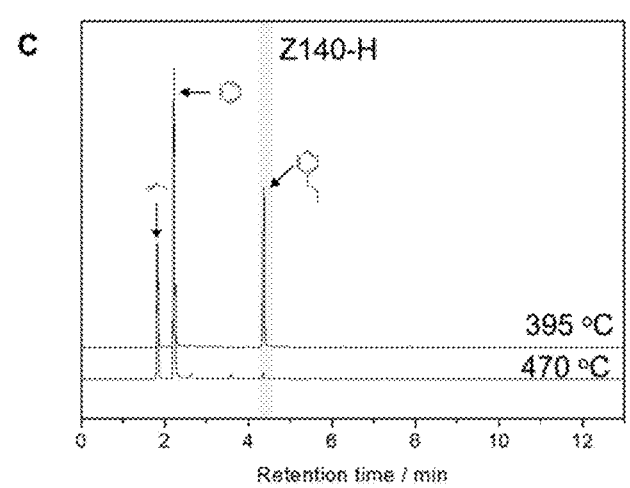
Figure 6D:
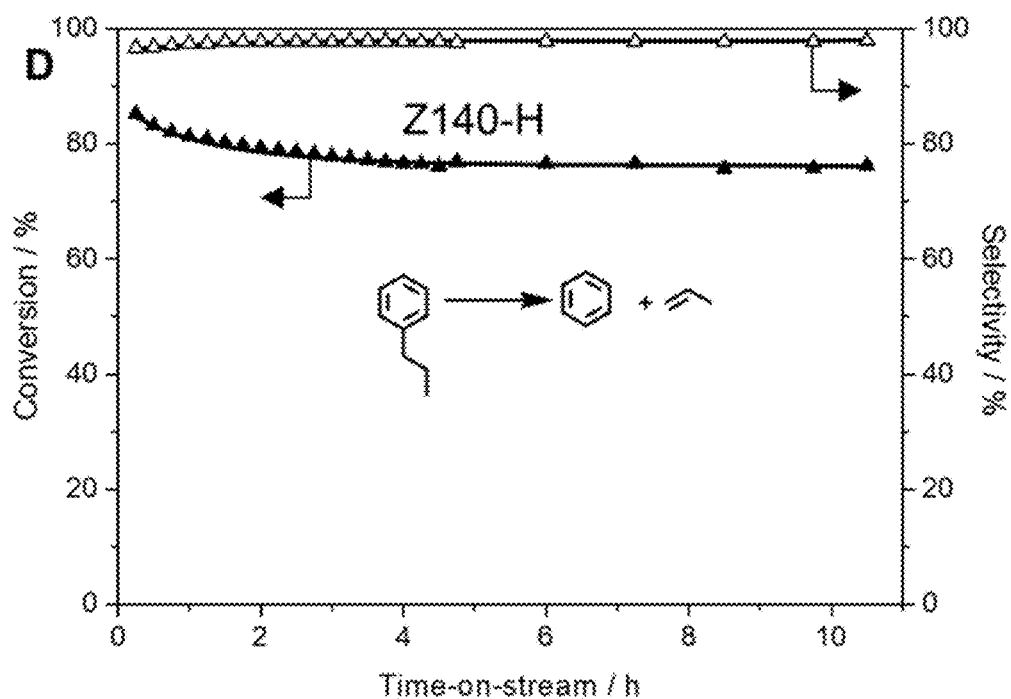
Figure 6E:
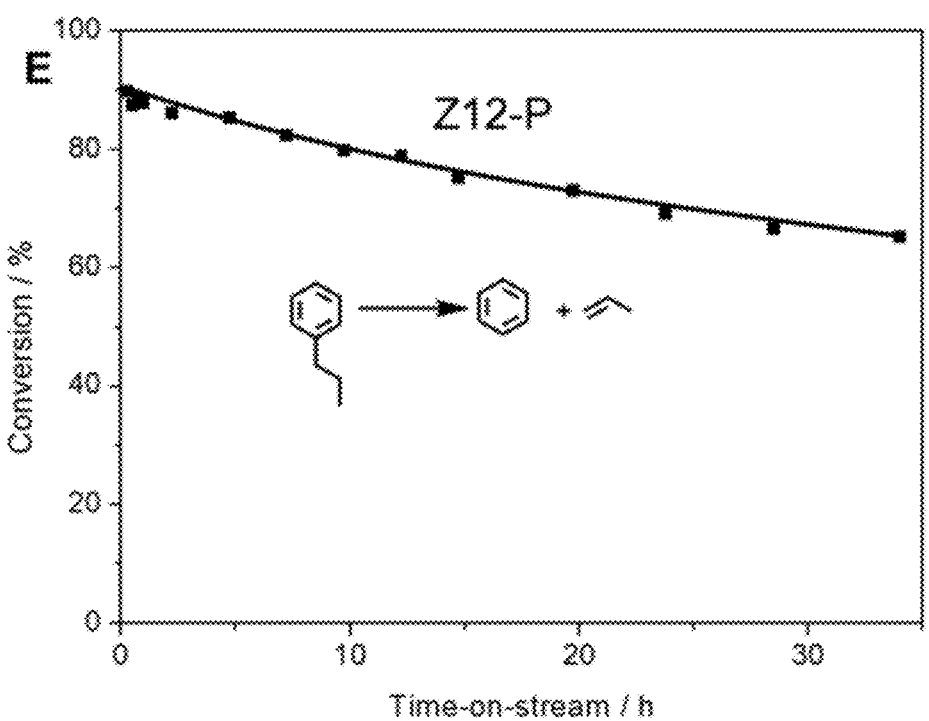
Figure 7A:
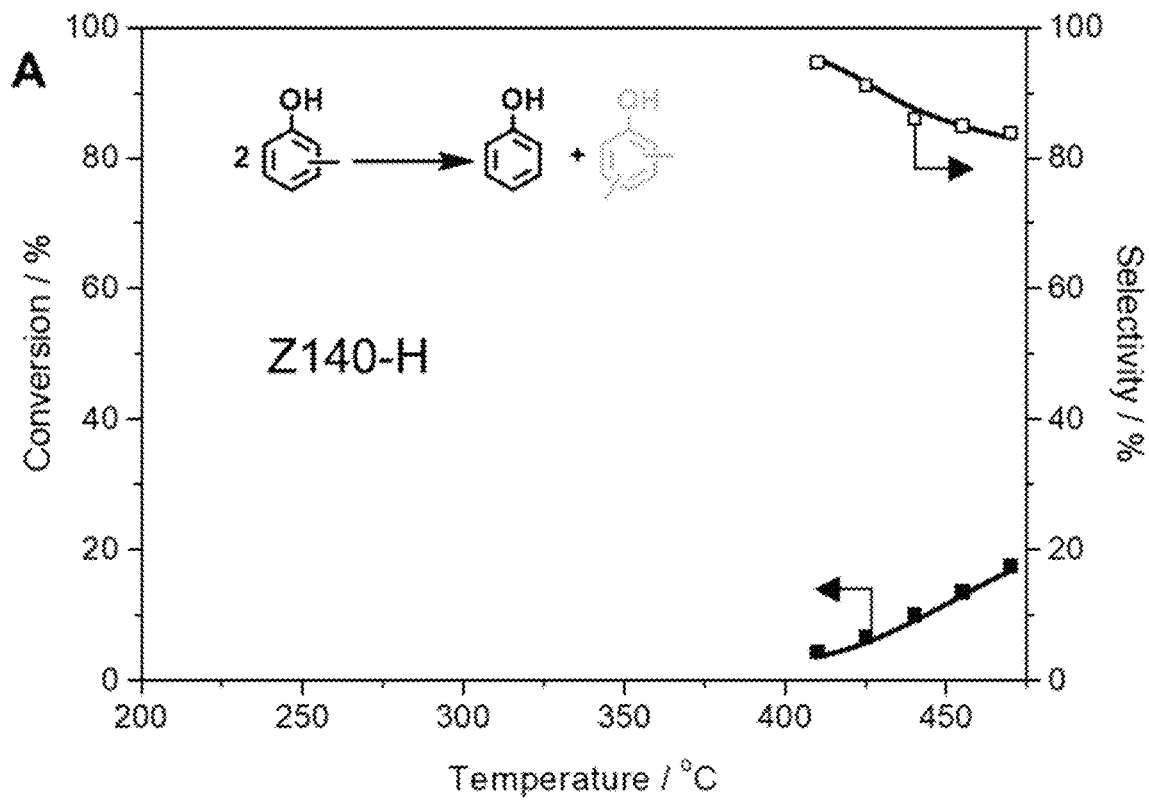
FIGS. 7A-7F. Catalytic conversion of cresols over zeolites.
Figure 7B:
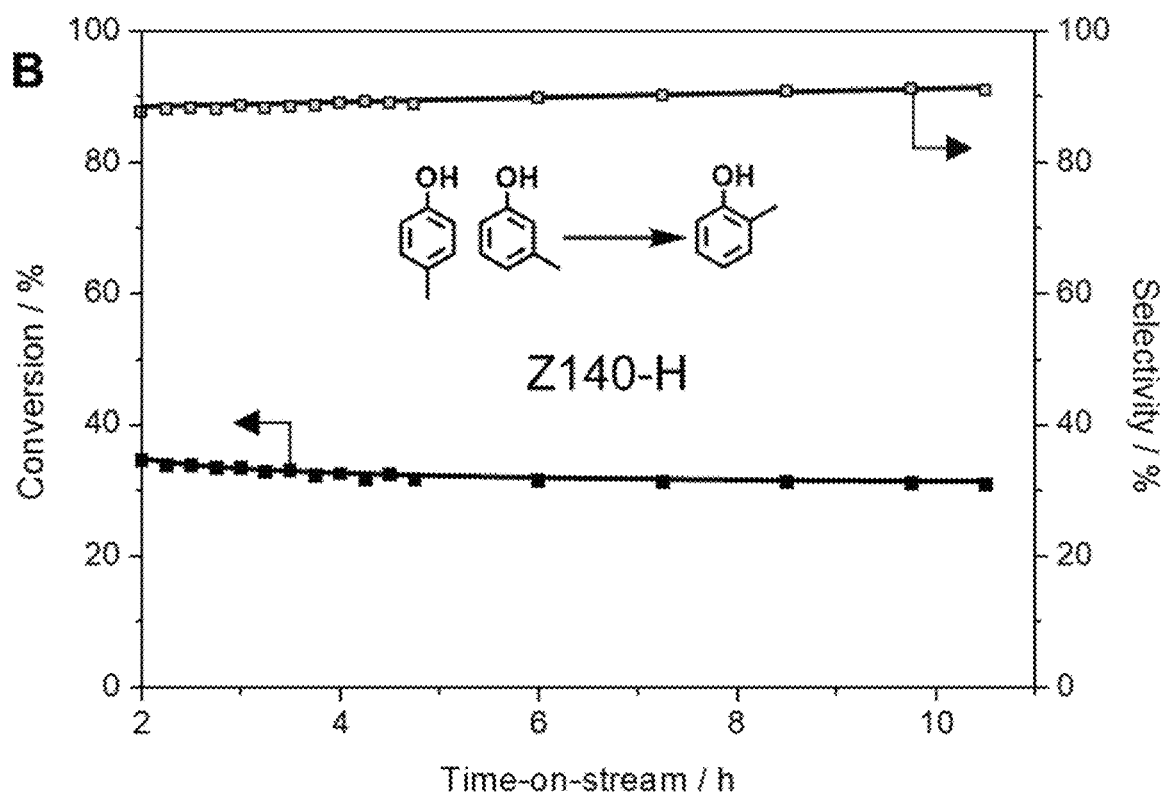
Figure 7C:
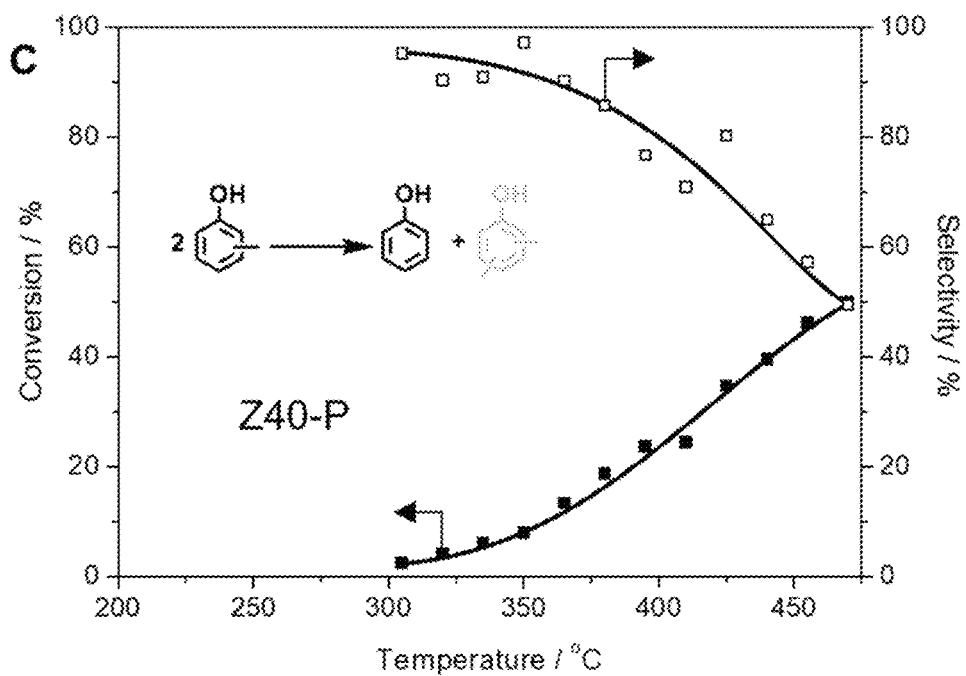
Figure 7D:
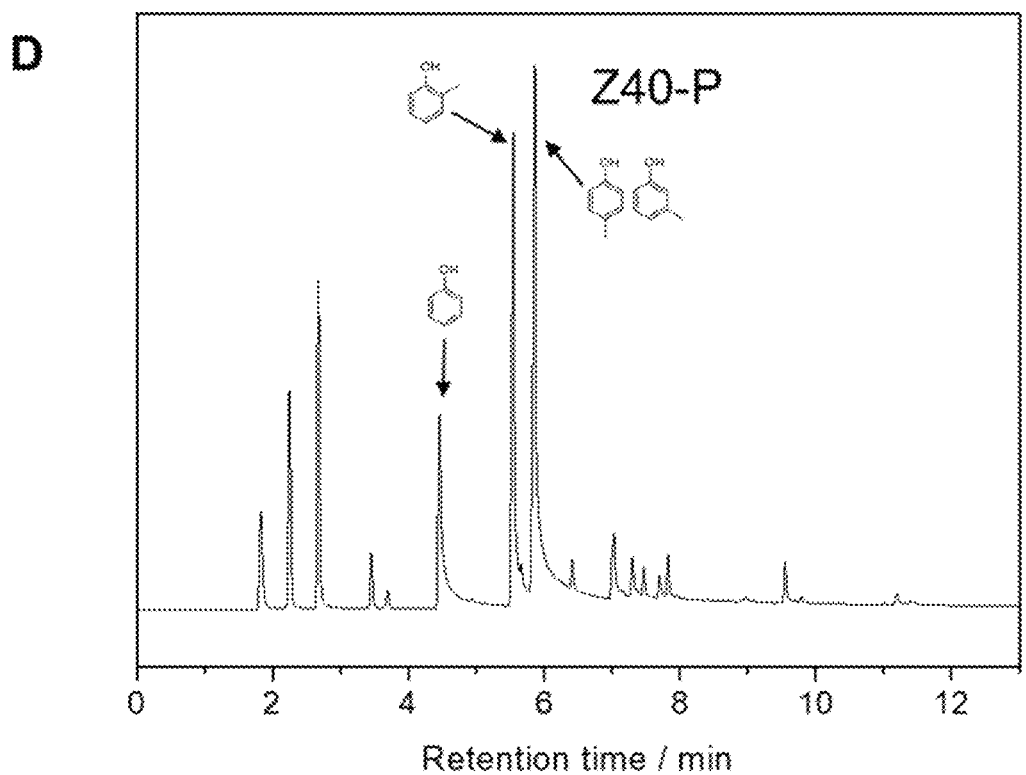
Figure 7E:
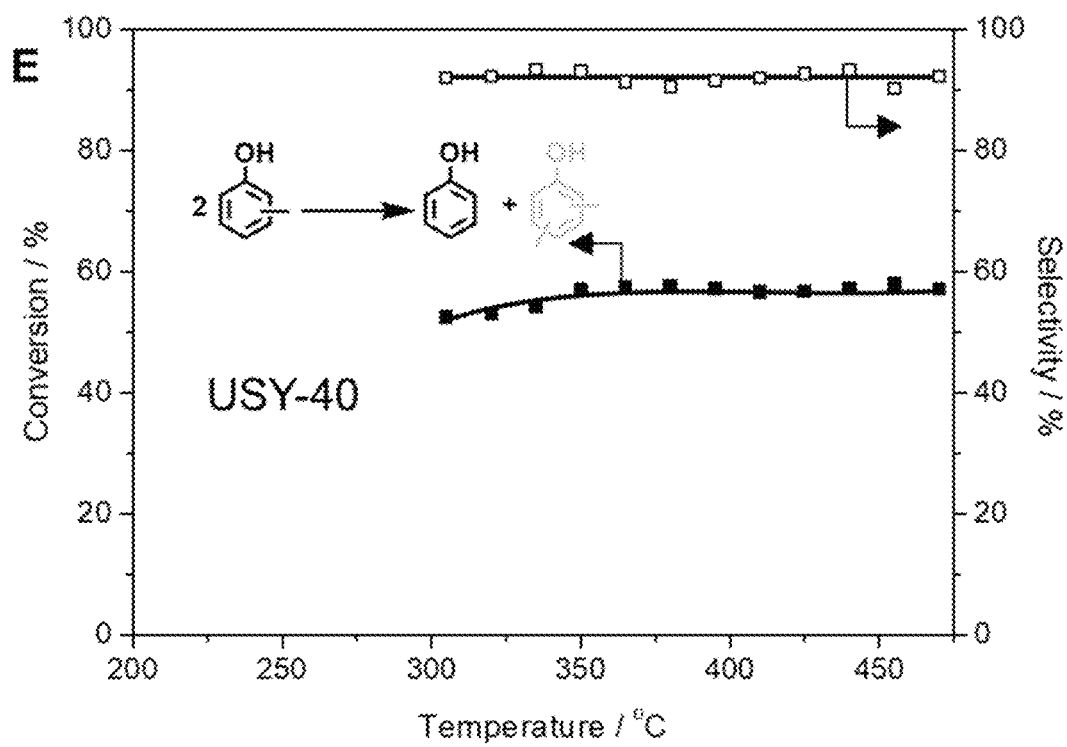
Figure 7F:
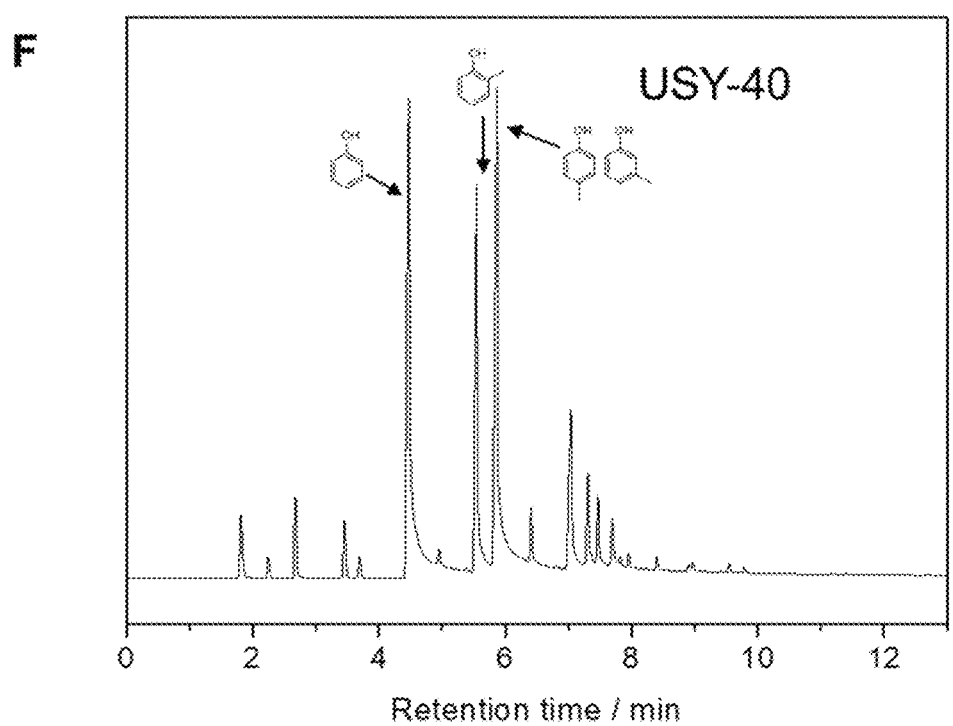

Similarly, (bulky) isomers of n-PP and n-EP present in the crude stream undergo selective dealkylation to phenol and corresponding olefin over Z140-H at full conversion (FIG. 5G).

The importance of pore structure and acidity modification is verified by the stable catalytic performance of hierarchical zeolites for conversion of n-propylbenzene—a major impurity in the alkylphenols (FIG. 6).

Cresols are another group of by-products in the crude alkylphenols stream. It was shown with pure cresols that their conversion in the dealkylation step is suboptimal (FIG. 7). Dealkylation of cresols is much more difficult than cleaving propyl/ethyl off. Cresols are thus best separated via existing technology such as batch distillation as applied in coal tar processing.[11] Optionally, the separated cresols stream can be converted in an additional step through bimolecular pathways such as disproportionation/transalkylation by using a large pore acidic zeolite such as USY, to produce phenol and xylenols.[68] For instance, use of commercial USY zeolite (USY-40, Si/Al=40) shows up to 90% of the theoretical selectivity with a (thermodynamic limited) conversion of about 57% (FIG. 7). Integration of this cresols conversion step can improve the phenol yield for 5%, while the obtained xylenols can be separated and used as antioxidants.[69]

The extracted crude phenolic monomers can thus be transformed into phenol and propylene with 20 and 9 wt. % yields, respectively. The markets of phenol and propylene are established, and this invention may supply them with bio-derived alternatives. Anticipating a future post-bisphenol A era, phenol may be considered for production of aniline and caprolactam in existing facilities,[48,70] while propylene without further purification may be suitable to produce chemicals like isopropanol, given the uncertainty today of its purity for material production. Reductive catalytic fractionation also produces a carbohydrate pulp and phenolic oligomers stream. Carbohydrate pulp is amenable for bioethanol production, while other applications such as newspaper and cardboard are possible.[71] A titer of 40.2 g L$^{-1}$ ethanol was reached via a semi-simultaneous saccharification-fermentation process using CTEC 2 saccharification enzyme and engineered yeast MDS130 (to ferment both glucose and xylose). Presence of catalyst impurity (from the reductive catalytic fraction) was endurable for this biological conversion.

Phenolic oligomers contain high functionality (3.46 mmol phenolic OH per gram, 2.48 mmol aliphatic OH per gram) and almost no original phenolic interlinkages. Next to the high functionality, other potential advantage are a low MW, compared to technical lignins (e.g., Kraft, Organosolv), and good solubility in various solvents at room temperature (e.g., acetone, ethanol, ethylacetate, DCM, DMSO, acetonitrile)

Figure 8:
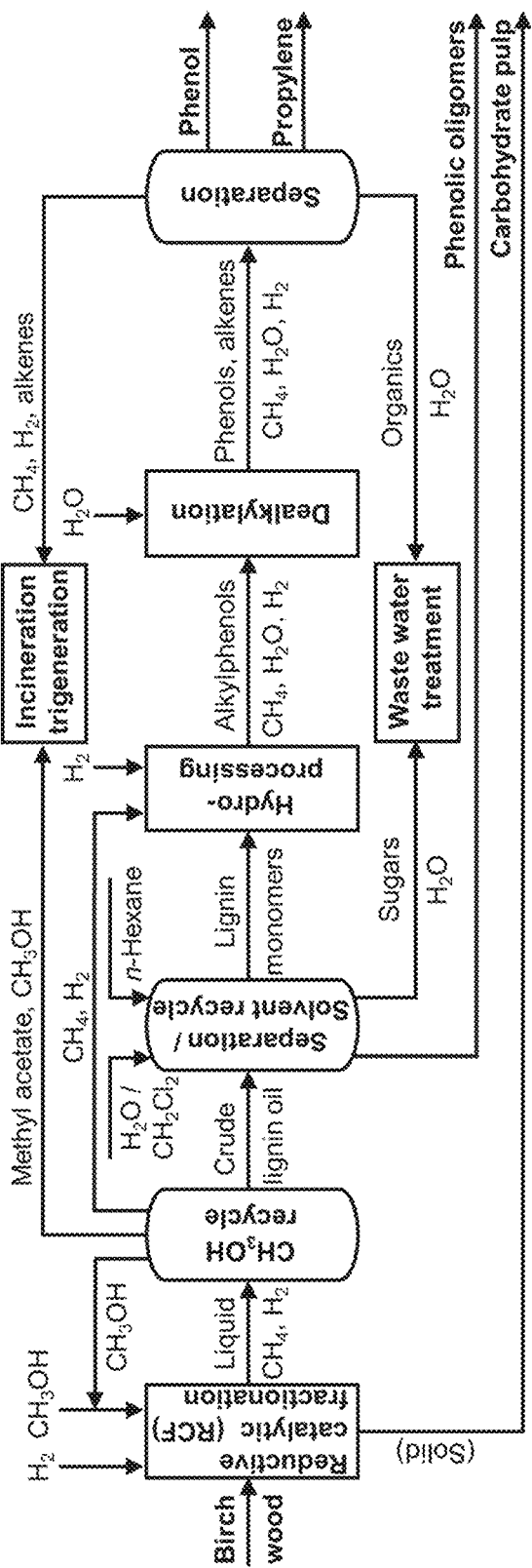
FIG. 8. Proposed integrated biorefinery process flow diagram. Overview of the process to produce carbohydrate pulp, phenol, propylene, phenolic oligomers from lignocellulose.
Figure 9A:
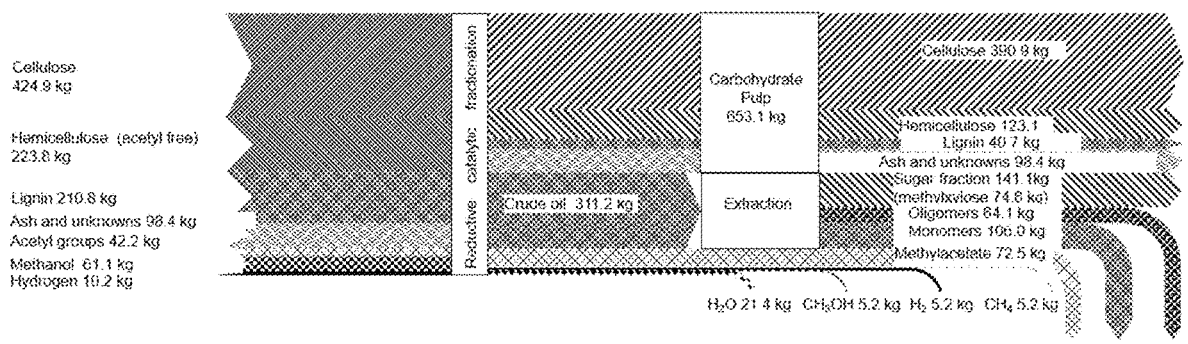
FIGS. 9A-9B.
Figure 9B:
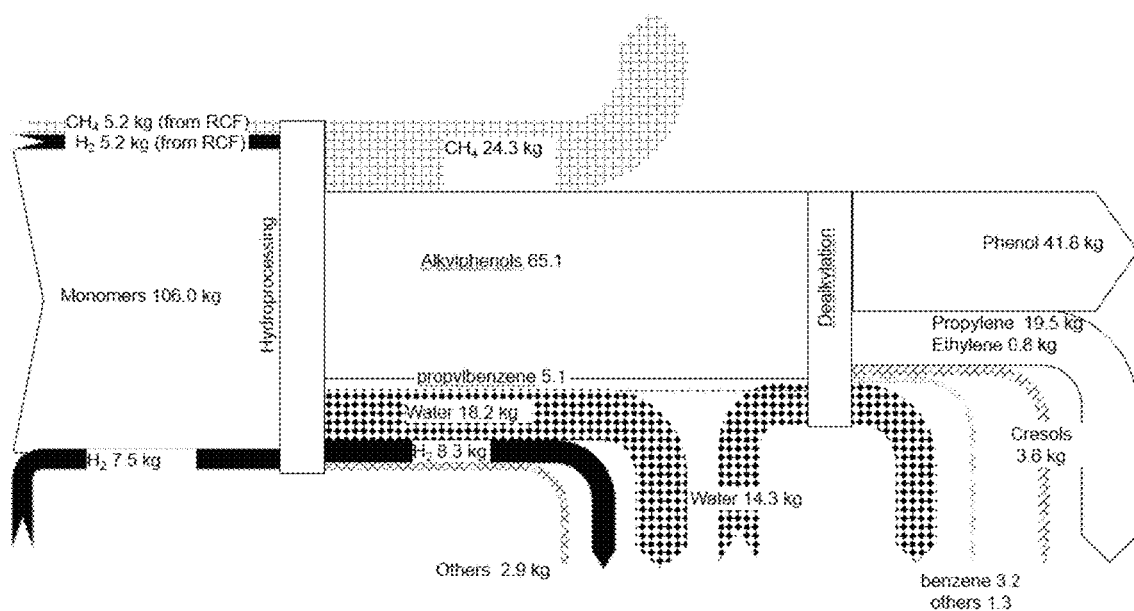

On the basis of the experimental data, an integrated process was designed (FIG. 8) and performed a techno-economic analysis. The process integrates the three catalytic steps. First, lignin-oil and pulp are produced by reductive catalytic fraction wood processing in either batch or (semi-)continuous reactor. After the liquid/solid separation, monomers isolation from lignin-oil is readily achieved in a liquid extraction unit, followed by flash distillation to remove n-hexane. Thereafter, the crude extract (monomers fraction), together with RCF off gas containing $H_2$ and some methane impurities (from MeOH in RCF) are fed into the gas-phase fixed-bed setup, containing Ni catalyst to form alkylphenols (i.e., hydroprocessing). Since the presence of hydrogen has no impact on the olefins formation, this alkylphenolics crude, containing water (supporting stable catalysis), hydrogen and methane impurities (inert components) is fed without intermediate purification to the second fixed-bed reactor for conversion to phenol and olefins over preferred (hierarchical) ZSM-5. Next, product separation is foreseen in a gas-liquid separator, producing a liquor of phenol, and a gaseous mixture of water, olefins, $H_2$ and $CH_4$. Finally, to obtain highly pure phenol and propylene, impurities like cresol and benzene in the phenol fraction and $H_2/CH_4$ in gas fraction can be removed by distillation. The degraded sugars (from RCF) and side products like benzene and cresols are treated in the waste water. Methyl acetate from the acetyl group of birch wood, which is largely separated in the methanol recovery distillation, excess $H_2$, $CH_4$, $C_2H_4$, and small amounts of methanol (from distillation) are sent to the incineration/trigeneration to foresee heating, cooling and electricity. The whole process can convert 1 MT of biomass into 653 kg of raw pulp for bioethanol, 64 kg of lignin oligomers, 42 kg of phenol and 20 kg of propylene (>99%), corresponding to 78 wt. % of biomass converted into isolated products (FIG. 9). Addition of external energy is not required to operate the integrated biorefinery. Loss of solvent was studied critically, showing a total loss of 1.4% due to distillation, consumption in RCF and incorporation in chemicals.

The techno-economic analysis of the proposed biorefinery is studied with an annual production of 100 ktonnes of bio-phenol (i.e., average scale for fossil-based phenol production). Among the different process units, RCF and incineration/trigeneration are the highest contributors toward CAPEX due to the high cost of pressure reactors and energy integration, respectively. Investing in an incineration/trigeneration unit however is justified by its positive impact on the manufacture cost because of the strongly reduced energy costs. The highest contribution to the manufacture cost is the feedstock (birch wood, 158€·tonne$^{-1}$). Given the current pricing of phenol (1300€·tonne$^{-1}$), propylene (830 €·tonne$^1$) and crude pulp (400 €·tonne$^{-1}$), and using an estimate for the oligomers (1750€·tonne$^{-1}$, approaching that of nonylphenol), this resulted in an internal rate of return (RR) of 23.33% and a payout time of approximately four years for a plant with a 20 year lifetime). A sensitivity study indicated that feedstock and product prices have the largest economic impact while the influence of catalyst cost is negligible as long as the catalyst is sufficiently recyclable/reusable. In terms of RCF process parameters, shorter contact times and higher biomass concentrations are crucial factors to improve the profitability of this biorefinery, although development of a dedicated reactor will be necessary.

Figure 10A:
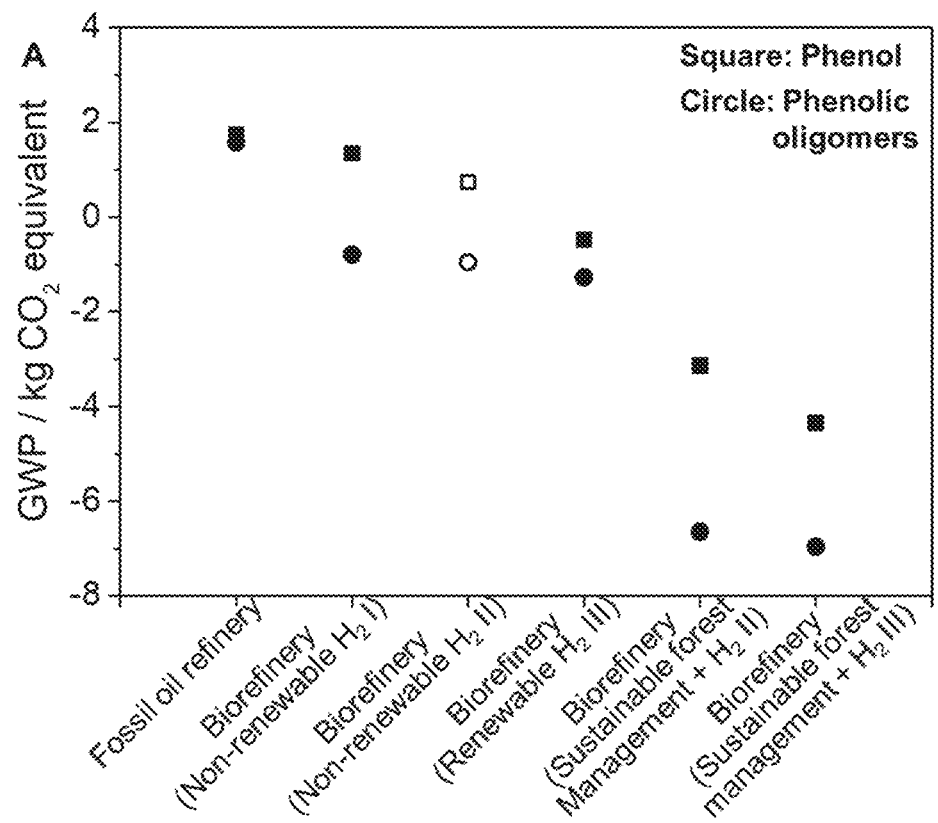
FIGS. 10A-10B. GWP of (FIG. 10A) phenol, phenolic oligomers, (FIG. 10B) propylene, and carbohydrate pulp in this biorefinery with different scenarios (i.e., several hydrogen sources and/or forest management strategies). The GWP of $H_2$ is, respectively, 11.89 kg $CO_2$ equivalent, 8.20 kg $CO_2$ equivalent, and 0.97 kg $CO_2$ equivalent for non-renewable $H_2$ I, non-renewable $H_2$ II, and renewable $H_2$ III. The GWP of phenolic oligomers from oil refinery is GWP of non-ylphenol (>1.58 kg $CO_2$ equivalent).
Figure 10B:
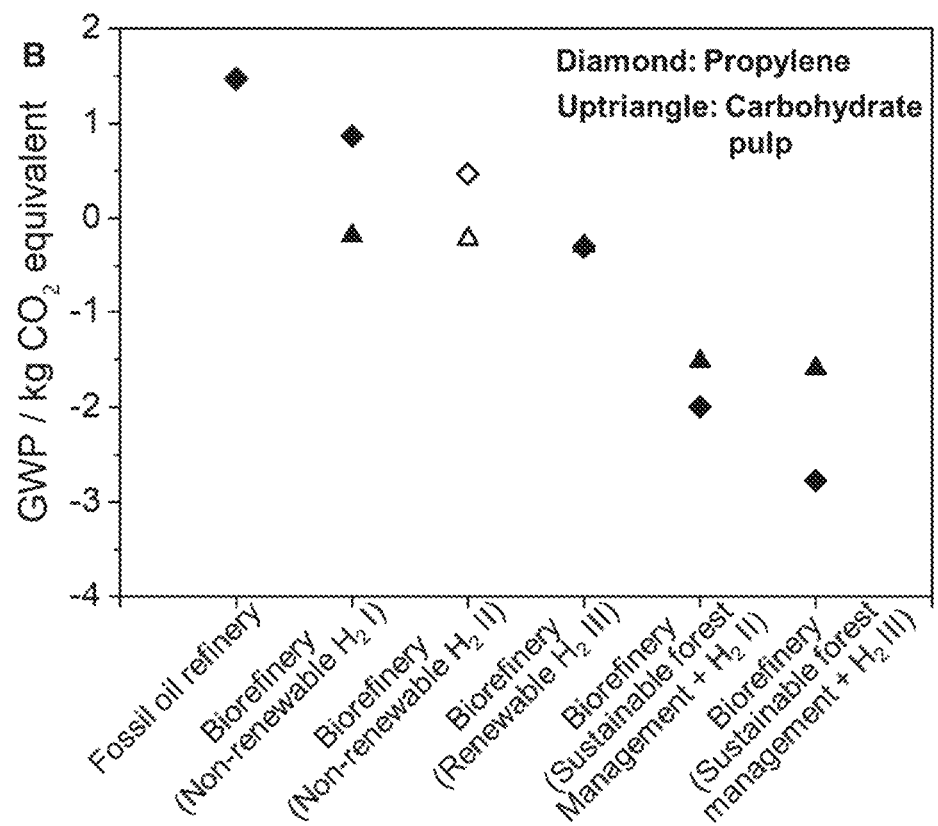

Because production of chemicals from biomass only makes sense if a lower $CO^2$ footprint is achieved, besides TEA, life-cycle assessment (LCA) was done. LCA of our proposed integrated biorefinery showed reduced global warming potentials (GWPs) for phenol (0.736 kg $CO_2$ equivalent) and propylene (0.469 kg $CO_2$ equivalent) compared to their fossil-based counterparts (1.73 kg and 1.47 kg $CO_2$ equivalent, respectively; open and red symbols in FIG. 10). Moreover, the GWP of the oligomers (proposed as substitute for para-nonylphenol with a GWP of >1.58 kg $CO_2$ equivalent) and the carbohydrate pulp were calculated to be −0.949 and −0.217 kg $CO_2$ equivalent, respectively (open symbols in FIG. 10). These latter negative values actually implicate a net consumption of $CO_2$, i.e., a net carbon capturing effect. Finally, to indicate opportunities to further improve overall sustainability, additional scenarios were analyzed as well, e.g., (i) the substitution of non-renewable $H_2$, which has a high $CO_2$ contribution, by renewable $H_2$, and (ii) inclusion of more sustainable forest management (FIG. 10). Such integrations reveal the possibility of $CO_2$ neutral lignocellulosic biorefineries with a total net consumption of $CO_2$ (i.e., negative GWP values) for each targeted product.

Figure 11:
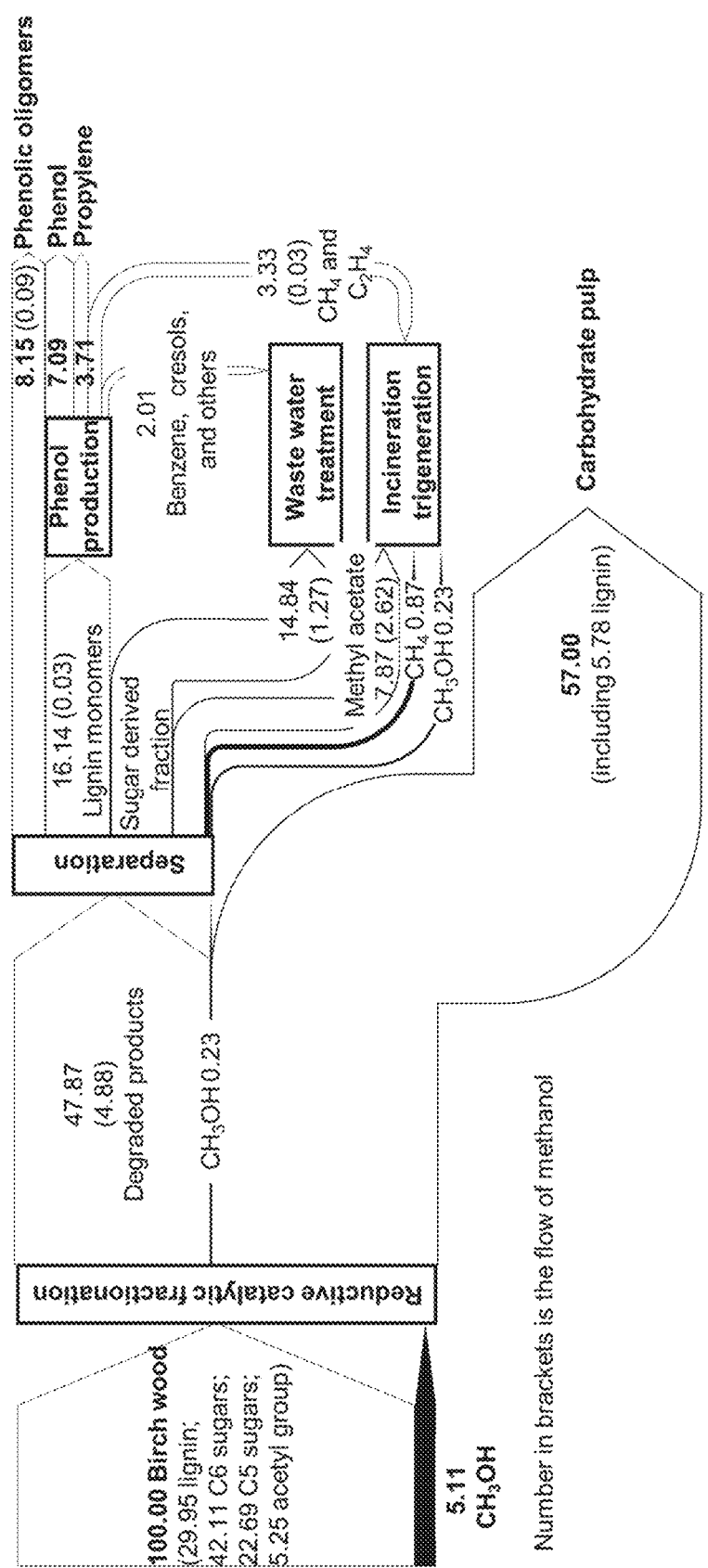
FIG. 11. Carbon flow of this biorefinery. Numbers in red represent carbon from methanol FIGS. 12A-12D. Dealkylation of 4-n-propylphenol over Z140-H.

Overall, according to the proposed holistic biorefinery, 78% of initial mass content (FIG. 9) of birch wood (76% carbon content, FIG. 11) can be economically and sustainably converted into high-value products (pulp, oligomers, phenol and propylene).

Particular and preferred aspects of this disclosure are set out in the accompanying independent and dependent claims. Features from the dependent claims may be combined with features of the independent claims and with features of other dependent claims as appropriate and not merely as explicitly set out in the claims.

Thus, the claims following the detailed description are hereby expressly incorporated into this detailed description, with each claim standing on its own as a separate embodiment of this invention.

General Experimental Procedure

I. Reductive Catalytic Fractionation of Lignocellulose:

For the production of the lignin-derived phenolic monomers, oligomers, and carbohydrate pulp, a 2 L stirred batch reactor (Parr Instruments Co.) was loaded with 150 g of wood chips (particle size: <10 mm), 800 mL of organic solvent and 15 g of catalyst. The reaction vessel was closed and flushed three times with N2 (8 bar) in order to remove the residual oxygen. High pressure $H_2$ was applied on the reaction mixture before heating, and the reactor is stirred at 720 rpm. The reaction was performed at 235° C. After several hours, the reaction was terminated by rapid cooling with compressed air flow and water. The reactor content was filtered in order to separate the solid fraction, containing the carbohydrate pulp and the catalyst, and the liquid fraction, containing the lignin oil and some soluble sugar products. To collect all liquid fraction, the solid residue was washed with EtOH. Afterwards, organic solvent used in the reaction and EtOH were removed from the liquid phase by rotary evaporation to yield a crude brownish colored lignin oil, containing some soluble sugar products next to phenolic monomers and oligomers.

A threefold liquid-liquid extraction with water and dichloromethane (DCM) at a mass ratio of 1/3/3 (crude lignin oil/DCM/water) was performed to separate the soluble sugar products from the lignin-derived products, prior to gas chromatographic analysis and lignin monomers separation (vide infra). Note that >99 wt. % of the lignin derived monomers in the lignin oil is present in the DCM phase, while >99 wt. % of sugar products is presented in water phase. Evaporation of DCM yielded the sugar-free lignin oil, consisting of phenolic monomers and oligomers. The weight of the sugar-free lignin oil was used to calculate the degree of delignification (on the basis of the Klason lignin weight) and to quantify the lignin products. The phenolic monomers were quantified using a Gas Chromatograph (GC, Agilent 6890) equipped with a HP5 column and a FID. 2-Isopropylphenol was used as the internal standard. The following parameters were used in the GC analysis: injection and detection temperature of 300° C., column temperature program: 50° C. (2 min), 15° C. min$^{-1}$ to 150° C., 10° C. min$^{-1}$ to 220° C. and 20° C. min$^{-1}$ to 290° C. (12 min).

II. Lignin Monomers Extraction

To isolate the lignin-derived phenolic monomers from the sugar-free lignin oil, liquid-liquid extraction was applied. After removal of the soluble sugars (RCF part), the purified lignin oil was subjected to a three or fourfold reflux extraction with alkane (at 80° C. of oil bath for 3 h), and the extract was distilled in vacuo to obtain a transparent yellowish oil. This oil presents the concentrated fraction of the phenolic monomers.

III. Demethoxylation or Demethylation/Dihydroxylation

In a typical experiment, certain amount of catalyst, pelletized to a 0.125-0.25 mm fraction, was loaded into the four quartz reactor tubes and held by two layers of quartz wool. The catalyst was diluted with quartz powder (0.125-0.25 mm) to reduce the local hot spots and to improve the temperature distribution, yielding a catalyst bed with a height of ca. 15 mm. Reactor temperature in axial direction of the oven at height of the catalyst bed is homogeneous. The gas phase substrate, $H_2$, and $N_2$ were mixed in a mixer before feed into the reactor. Typically, the molar composition of the gas mixture in the reactor before reaction is 0.02/0.4/0.58 (for substrate/$H_2$/$N_2$) or 0.2/0.98 (for substrate/$H_2$). The effluent gases were analyzed using an online GC (HP4890D) equipped with two parallel columns (HP1 column and Porapolt Q column), both connected with a FID. The products of demethoxylation or demethylation/dehydroxylation of phenolic monomers were collected and used to undergo catalytic dealkylation to form biophenol and biopropylene. The unit of WHSV is g $g_{eatal}^{-1}$ $h^{-1}$ (i.e., $h^{-1}$).

IV. Dealkylation

In a typical dealkylation experiment, 120 mg of zeolite catalyst, pelletized to a 0.125-0.25 mm fraction, was loaded into the four quartz reactor tubes (30 mg catalyst per tube) and held by two layers of quartz wool, yielding a catalyst bed of ca. 13 mm. Water was also fed into reactor. The gas substrate, water, and $N_2$ were mixed in a mixer before fed into the reactor. The molar composition of the gas-phase before reaction is 0.02/0.12/0.86 (alkylphenols/water/$N_2$). Dealkylation of 4-n-propylphenol in the presence of $H_2$ was also conducted (as test reaction) by replacing $N_{12}$ with $H_2$. The effluent gases were characterized by the above mentioned online GC equipped with two FIDs, a HP column and a Porapolt Q column. The unit of WHSV is g $g_{eatal}^{-1}$ $h^{-1}$ (i.e., $h^{-1}$).

Some embodiments of this disclosure are set forth in "claim" format directly below:

1. A method comprising the steps of: a) providing a mixture of compounds of formula (I):

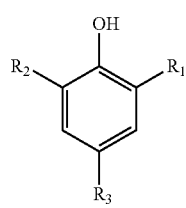

wherein: each occurrence of R1 and R2 is independently selected to be —O—$CH_3$ or —H; each occurrence of R3 is independently selected to be —H, or -methyl, or -ethyl, or -propyl, or -propylene, or -1-alkoxypropyl, or -3-hydroxypropyl; b) preparing a reaction mixture by contacting the mixture of compounds of step a) in gas phase, with a reaction mixture containing a metal-based catalyst, under a hydrogen containing gas atmosphere; wherein step b) is carried out at a temperature of at least 265° C. and a partial hydrogen pressure of at least 0.2 bar; c) obtaining from step b) products comprising a mixture of compounds of formula (Ia), as well as methane or methanol or both,

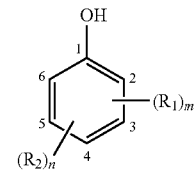

wherein: R1 is independently selected to be —CH3 or —H; R2 is independently selected to be —H, or -methyl, or -ethyl, or -propyl; m and n represent the position on the aromatic ring, with m being any one of the numbers 2-6 and with n being any one of the numbers 3-5, with m not being equal to n.

2. The method as in embodiment 1 here above in paragraph [0093], wherein the metal catalyst comprises metal attached on a support material.

3. The method as in any of the embodiments 1-2 (paragraphs [0093]-[0094]), wherein the metal catalyst comprises metal attached on a support material whereby the metal is nickel and the support is silica.

4. The method as in any of the embodiments 1-3 (paragraphs [0093]-[0094]-[0095]), wherein the metal catalyst is a promoter-modified nickel catalyst.

5. The method as in any of the 1-4 embodiments (paragraphs [0093]-[0094]-[0095]-[0096]), wherein in step b) a partial pressure of 0.2-10 bar $H_2$ is used.

6. The method as in any of the embodiments 1-5 (paragraphs [0093]-[0094]-[0095]-[0096]-[0097]), wherein in step b) a partial pressure of 0.2-1 bar $H_2$ is used.

7. The method as in any of the embodiments 1-6 (paragraphs [0093]-[0094]-[0095]-[0096]-[0097]-[0098]), wherein a complete removal of methoxy substituents is obtained with >70% molar yield to propyl phenols or ethyl phenols or a combination of both, based on a mixture of compounds with formula I.

8. The method as in any of the embodiments 1-7 (paragraphs [0093]-[0094]-[0095]-[0096]-[0097]-[0098]-[0099]), wherein the resulting products with formula Ia obtained in step c) in embodiment 1 are subjected to a dealkylation process comprising the steps of: d) providing the mixture of compounds of formula (Ia); e) preparing a reaction mixture by contacting the mixture of compounds of step d) in gas phase, with an acidic zeolite, and water and wherein step e) is carried out at a temperature of at least 260° C.; and f) obtaining from step e) products comprising a mixture of compounds of formula (Ib) as well as olefins comprising propylene or ethylene or a combination of both,

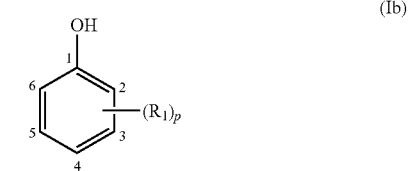

wherein: R1 is independently selected to be —CH3 or —H; p represents the position on the aromatic ring, with p being any one of the numbers 2-6.

9. The method as in any of the embodiments 1-8 (paragraphs [0093]-[0094]-[0095]-[0096]-[0097]-[0098]-[0099]-[0100]), wherein the acidic zeolite belongs to the pentasil family of zeolites.

10. The method as in any of the embodiments 1-9 (paragraphs [0093]-[0094]-[0095]-[0096]-[0097]-[0098]-[0099]-[0100]-[0101]), wherein the acidic zeolite is a ZSM-5 zeolite 11. The method as in any of the embodiments 1-10 (paragraphs [0093]-[0094]-[0095]-[0096]-[0097]-[0098]-[0099]-[0100]-[0101]-[0102]), wherein the acidic zeolite is a hierarchical version of a ZSM-5 zeolite with Si/Al ratio of 140.

12. The method as in any of the embodiments 1-11 (paragraphs [0093]-[0094]-[0095]-[0096]-[0097]-[0098]-[0099]-[0100]-[0101]-[0102]-[0103]), wherein the mixture of compounds with formula Ib and olefins are obtained in a molar yield of >40% based on the mixture of compounds with formula I.

13. The method as in any of the embodiments 1, 5, 6, (paragraphs [0093], [0097], [0098]) wherein the produced mixture of compounds with formula Ia is further converted to a mixture of compounds with formula Ic.

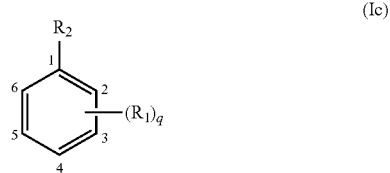

wherein: R1 is independently selected to be —CH3 or —H; R2 is independently selected to be -propyl or -ethyl; q represents the position on the aromatic ring, with q being any one of the numbers 2-6.

14. The method as in any of the embodiments 1, 5, 6, 13, (paragraphs [0093], [0097], [0098], [0105]) wherein the catalyst comprises a platinum group metal (PGM) selected of platinum or palladium, and whereby this metal is on a titanium oxide support.

15. The method as in any of the embodiments 1, 5, 6, 13, 14 (paragraphs [0093], [0097], [0098]), [0105], [0106]), wherein the catalyst is selected of a promoter-modified platinum catalyst or a promoter-modified palladium catalyst.

16. The method as in any of the embodiments 1, 5, 6, 13-15 (paragraphs [0093], [0097], [0098]), [0105], [0106], [0107]), wherein the catalyst achieves a constant conversion of the mixture of compounds with formula I for a time on stream of at least 5 hours, measured at a conversion level below full conversion.

17. The method as in any of the embodiments 1, 5, 6, 13-16 (paragraphs [0093], [0097], [0098]), [0105], [0106], [0107], [0108]), wherein a mixture of compounds with formula Ic is obtained in >60% molar yield based on a mixture of compounds with formula I.

18. The method as in any of the embodiments 1, 5, 6, 13-17 (paragraphs [0093], [0097], [0098]), [0105], [0106], [0107], [0108], [0109]), wherein n-propylbenzene is obtained in >40% molar yield based on a mixture of compounds with formula I.

19. The method according to anyone of embodiments 1-18 (paragraphs [0093]-[0110]; wherein the mixture of compounds of formula (I) are derived from lignocellulose.

20. The method as in any of the embodiments 1-19 (paragraphs [0093]-[0111]; wherein the mixture of compounds of formula (I) are derived from lignocellulose feedstock and are present in the lignin monomers enrich fraction obtained via a lignocellulose biorefinery process comprising the following steps: 1) reductive catalytic fractionation (biomass fractionation with lignin depolymerization) of lignocellulose, forming two fractions, a carbohydrate pulp and lignin oil, 2) separating the carbohydrate pulp and lignin oil fractions, 3) separating the monomer and oligomer fractions present in the lignin oil.

21. The method as in any of the embodiments 1-20 (paragraphs [0093]-[0112]), wherein the mixture of compounds of formula (I) are derived from lignocellulose feedstock, being present in the lignin monomers fraction obtained via a lignocellulose biorefinery process comprising the following steps: 1.a) subjecting a lignocellulose mass in contact with a metal catalyst, $H_2$ and solvent to reductive catalytic fractionation to produce a carbohydrate pulp and a liquid, b) solvent evaporation from the liquid to obtain lignin oil, hereby recycling the solvent for reuse in step a, and recycling $H_2$ and formed methane for reuse in step d. c) contacting the lignin oil to a two-step liquid extraction with first $H_2O$ and $CH_2Cl_2H_2O$ or ethylacetate to isolate 1) a sugar water stream, and subsequently an extraction of the sugar-free lignin oil with an alkane solvent, such as hexane, heptane or octane, whereby are separated 2) lignin oligomers and 3) lignin monomers.

22. The method as in any of the embodiments 1-12 (paragraphs [0093]-[0104]) and embodiments 19-21 (paragraphs [0111]-[0113]; wherein the lignin monomers fraction, together with an $H_2$-gas stream, such as the gas stream from reductive catalytic fractionation, containing amongst others methane impurities (from methane formation during RCF) are fed into the gas-phase fixed-bed setup, containing Ni catalyst to form alkylphenols by demethoxylation and/or cascade demethylation/dehydroxylation 2) this alkylphenolics crude, containing water (supporting stable catalysis), hydrogen and methane impurities is fed without intermediate purification to the second fixed-bed reactor for conversion to phenol and olefins over an acidic zeolite, 3) product separation is carried out in a gas-liquid separator, producing a liquor of phenol, and a gaseous mixture of water, olefins, $H_2$ and $CH_4$.

23. The method as in any of the embodiments 1-12 (paragraphs [0093]-[0104]) and embodiments 19-22 (paragraphs [0111]-[0114]); wherein >35% of the lignin present in the lignocellulose is converted into phenol, propylene, phenolic oligomers.

24. The method as in any of the embodiments 1-12 (paragraphs [0093]-[0104]) and embodiments 19-23 (paragraphs [0111]-[0115]); whereby to obtain highly pure phenol and propylene, impurities like cresol and benzene in the phenol fraction and $H_2/CH_4$ in gas fraction are removed by distillation.

25. The method as in any of the embodiments 1-12 (paragraphs [0093]-[0104]) and embodiments 19-24 (paragraphs [0111]-[0116]); to produce phenol, propylene, phenolic oligomers and a carbohydrate pulp from inplanta lignin with an overall carbon efficiency of >60%.

26. The method as in any of the embodiments 1-12 (paragraphs [0093]-[0104]) and embodiments 19-25 (paragraphs [0111]-[0117]); whereby >35% of the lignin is converted into >95% pure phenol and >95% propylene fraction, and lignin oligomers.

27. The method as in any of the embodiments 1-26 (paragraphs [0093]-[0118]); whereby the lignocellulose biorefinery process comprises lignocellulose fractionation with lignin depolymerization.

28. The method as in any of the embodiments 1-27 (paragraphs [0093]-[0119]); whereby the lignin oil formed is rich in extractable phenolic monomers.

29. The method as in any of the embodiments 1-28 (paragraphs [0093]-[0120]); wherein the lignocellulose mass comprises hardwood, softwood, herbaceous biomass, straw, bark, waste wood, flax shives, sugar cane bagasse, corn stover or crop residues.

30. The method as in any of the embodiments 1-29 (paragraphs [0093]-[0121]); whereby methyl acetate from the acetyl group of lignocellulose, separated in the solvent recovery distillation, together with excess $H_2$, $CH_4$, $C_2H_4$, and small amounts of solvent, are sent to the incineration/trigeneration to foresee heating, cooling and electricity.

31. The method as in any of the embodiments 1-30 (paragraphs [0093]-[0122]); whereby more than 2-fold and less than six-fold mass of n-hexane to lignin-oil extracts more than 70 wt. % of the phenolic monomers.

32. The method as in any of the embodiments 1-7 (paragraphs [0093]-[0099]), whereby the mixture of compounds of formula (I) is subjected to demethoxylation or cascade demethylation-dehydroxylation or both.

Examples

Example 1. Reductive catalytic fractionation of birch wood. This experiment was performed according to experimental procedure I. birch wood (150 g) was used as the feedstock, 5 wt % Ru/C as a catalyst, and methanol as the solvent. The reaction was conducted at 235° C. for 3 h under 30 bar of $H_2$ (room temperature). Conversion of lignin: 80.69%. Monomers yield (on the basis of Klason lignin): 4-propylguaiacol (9.71 wt %), isoeugenol (0.49 wt %), 4-(3-methoxypropyl)-guaiacol (<0.19 wt %), 4-n-prop-1-anolguaiacol (0.89 wt %), 4-ethylguaiacol (0.30 wt %), 4-propylsyringol (33.85 wt %), 4-prop-1-enylsyringol (0.32 wt %), 4-n-prop-1-anolsyringol (2.21 wt %), syringol (0.43 wt %), 4-methylsyringol (0.28 wt %), 4-ethylsryingol (1.03 wt %), 4-(3-methoxypropyl)-syringol (0.79 wt %), others (<0.02 wt %), total monomers (50.51 wt %). Oligomers (30.18 wt %).

Example 2. Reductive catalytic fractionation of pine wood. This experiment was performed according to experimental procedure I. pine wood (150 g) was used as the feedstock, 5 wt % Ru/C as a catalyst, and methanol as the solvent. The reaction was conducted at 235° C. for 3 h under 30 bar of $H_2$ (room temperature). Conversion of lignin: 37.30%. Monomers yield (on the basis of Klason lignin): 4-propylguaiacol (9.97 wt %), isoeugenol (0.83 wt %), 4-n-prop-1-anolguaiacol (1.96 wt %), 4-ethylguaiacol (0.21 wt %), 4-propylsyringol (0.02 wt %), 4-prop-1-enylsyringol (0.40 wt %), 4-n-prop-1-anolsyringol (0.01 1 wt %), 4-methylsyringol (0.02 wt %), 4-ethylsryingol (0.21 wt %), others (<0.42 wt %), total monomers (14.05 wt %). Oligomers (23.25 wt %).

Example 3. Monomers extraction. This experiment was performed according to experimental procedure II. n-Hexane was used as the solvent with a threefold reflux extraction at n-hexane/lignin=3:1 (mass ratio). The extract efficiency for the extractable monomers is 93.9%.

Example 4. Demethoxylation and demethylation/dihydroxylation. This experiment was performed according to experimental procedure III. 4-propylguaiacol was used as feedstock, 5 wt % Rh/$Al_2O_3$ as a catalyst. WHSV=4.5 $h^{-1}$. Reaction temperature: 285° C. 0.4 bar $H_2$ (1 bar of total pressure). The results were shown in FIG. 3A.

Example 5. Demethoxylation and demethylation/dihydroxylation. This experiment was performed according to experimental procedure III. 4-propylguaiacol was used as feedstock, 5 wt % Pt/$Al_2O_3$ as a catalyst. WHSV=4.5 $h^{-1}$. Reaction temperature: 285° C. 0.4 bar $H_2$ (1 bar of total pressure). The results were shown in FIG. 3A.

Example 6. Demethoxylation and demethylation/dihydroxylation. This experiment was performed according to experimental procedure III. 4-propylguaiacol was used as feedstock, 17 wt % Ni/$Al_2O_3$ as a catalyst. WHSV=4.5 $h^{-1}$. Reaction temperature: 285° C. 0.4 bar $H_2$ (1 bar of total pressure). The results were shown in FIG. 3A.

Example 7. Demethoxylation and demethylation/dihydroxylation. This experiment was performed according to experimental procedure III. 4-propylguaiacol was used as feedstock, 64 wt % Ni/$SiO_2$ as a catalyst. WHSV=4.5 $h^{-1}$. Reaction temperature: 285° C. 0.4 bar $H_2$ (1 bar of total pressure). The results were shown in FIG. 3A.

Example 8. Demethoxylation and demethylation/dihydroxylation. This experiment was performed according to experimental procedure III. 4-propylguaiacol was used as feedstock, 17 wt % Ni/$Al_2O_3$ as a catalyst. WHSV=2.7 $h^{-1}$. Reaction temperature: 285° C. 0.4 bar $H_2$ (1 bar of total pressure). The results were shown in FIG. 3A.

Example 9. Demethoxylation and demethylation/dihydroxylation. This experiment was performed according to experimental procedure III. 4-propylguaiacol was used as feedstock, 64 wt % Ni/$SiO_2$ as a catalyst. WHSV=9.0 $h^{-1}$. Reaction temperature: 285° C. 0.4 bar $H_2$ (1 bar of total pressure). The results were shown in FIG. 3A.

Example 10. Demethoxylation and demethylation/dihydroxylation. This experiment was performed according to experimental procedure III. 4-propylguaiacol was used as feedstock, 20 wt % Ni/$TiO_2$ as a catalyst. WHSV=2.7 $h^{-1}$. Reaction temperature: 285° C. 0.4 bar $H_2$ (1 bar of total pressure). The results were shown in FIG. 3B.

Example 11. Demethoxylation and demethylation/dihydroxylation. This experiment was performed according to experimental procedure III. 4-propylguaiacol was used as feedstock, 21 wt % Ni/$Al_2O_3$ as a catalyst. WHSV=4.5 $h^{-1}$. Reaction temperature: 285° C. 0.4 bar $H_2$ (1 bar of total pressure). The results were shown in FIG. 3B.

Example 12. Demethoxylation and demethylation/dihydroxylation. This experiment was performed according to experimental procedure III. 4-propylguaiacol was used as feedstock, 16 wt % Ni/$SiO_2$ as a catalyst. WHSV=4.5 $h^{-1}$. Reaction temperature: 285° C. 0.4 bar $H_2$ (1 bar of total pressure). The results were shown in FIG. 3B.

Example 13. Demethoxylation and demethylation/dihydroxylation. This experiment was performed according to experimental procedure III. 4-propylguaiacol was used as feedstock, 20 wt % Ni/$TiO_2$ as a catalyst. WHSV=4.5 $h^{-1}$. Reaction temperature: 285° C. 0.4 bar $H_2$ (1 bar of total pressure). The results were shown in FIG. 3B.

Example 14. Demethoxylation and demethylation/dihydroxylation. This experiment was performed according to experimental procedure III. 4-propylguaiacol was used as feedstock, 50 wt % Ni/Kieselguhr-$Cr_2O_3$ as a catalyst. WHSV=9.0 $h^{-1}$. Reaction temperature: 285° C. 0.4 bar $H_2$ (1 bar of total pressure). The results were shown in FIG. 3B.

Example 15. Demethoxylation and demethylation/dihydroxylation. This experiment was performed according to experimental procedure III. 4-propylguaiacol was used as feedstock, 65 wt % Ni/$SiO_2$—$Al_2O_3$ as a catalyst. WHSV=9.0 $h^{-1}$. Reaction temperature: 285° C. 0.4 bar $H_2$ (1 bar of total pressure). The results were shown in FIG. 3B.

Example 16. Demethoxylation and demethylation/dihydroxylation. This experiment was performed according to experimental procedure III. 4-propylguaiacol was used as feedstock, 55 wt % Ni/Kieselguhr as a catalyst. WHSV=9.0 h⁻¹. Reaction temperature: 285° C. 0.4 bar $H_2$ (1 bar of total pressure). The results were shown in FIG. 3B.

Example 17. Demethoxylation and demethylation/dihydroxylation. This experiment was performed according to experimental procedure III. 4-propylguaiacol was used as feedstock, 60 wt % Ni/Kieselguhr-$Al_2O_3$ as a catalyst. WHSV=9.0 h⁻¹. Reaction temperature: 285° C. 0.4 bar $H_2$ (1 bar of total pressure). The results were shown in FIG. 3B.

Example 18. Demethoxylation and demethylation/dihydroxylation. This experiment was performed according to experimental procedure III. 4-propylguaiacol was used as feedstock, 64 wt % Ni/$SiO_2$ as a catalyst. WHSV=6.0 h⁻¹. Reaction temperature: 285° C. 0.4 bar $H_2$ (1 bar of total pressure). The results were shown in FIG. 4C.

Example 19. Demethoxylation and demethylation/dihydroxylation. This experiment was performed according to experimental procedure III. 4-ethylguaiacol was used as feedstock, 64 wt % Ni/$SiO_2$ as a catalyst. WHSV=8.2 h⁻¹. Reaction temperature: 285° C. 0.4 bar $H_2$ (1 bar of total pressure). The results were shown in FIG. 4D.

Example 20. Demethoxylation and demethylation/dihydroxylation. This experiment was performed according to experimental procedure III. Isoeugenol was used as feedstock, 64 wt % Ni/$SiO_2$ as a catalyst. WHSV=4.4 h⁻¹. Reaction temperature: 285° C. 0.4 bar $H_2$ (1 bar of total pressure). The results were shown in FIG. 4D.

Example 21. Demethoxylation and demethylation/dihydroxylation. This experiment was performed according to experimental procedure III. 4-propylsyringol was used as feedstock, 64 wt % Ni/$SiO_2$ as a catalyst. WHSV=7.1 h⁻¹. Reaction temperature: 305° C. 0.4 bar $H_2$ (1 bar of total pressure). The results were shown in FIG. 4D.

Example 22. Demethoxylation and demethylation/dihydroxylation. This experiment was performed according to experimental procedure III. 4-propylsyringol was used as feedstock, 64 wt % Ni/$SiO_2$ as a catalyst. WHSV=5.3 h⁻¹. Reaction temperature: 305° C. 0.4 bar $H_2$ (1 bar of total pressure). The results were shown in FIG. 4D.

Example 23. Demethoxylation and demethylation/dihydroxylation. This experiment was performed according to experimental procedure III. Lignin monomers obtained reductive catalytic fractionation of pine wood (example 2) after extraction was used as feedstock, 64 wt % Ni/$SiO_2$ as a catalyst. WHSV=6.0 h⁻¹. Reaction temperature: 285° C. 0.4 bar $H_2$ (1 bar of total pressure). The results were shown in FIG. 4D.

Example 24. Demethoxylation and demethylation/dihydroxylation. This experiment was performed according to experimental procedure III. Lignin monomers obtained reductive catalytic fractionation of birch wood (example 1 and example 3) after extraction was used as feedstock, 64 wt % Ni/$SiO_2$ as a catalyst. WHSV=5.3 h⁻¹. Reaction temperature: 305° C. 0.4 bar $H_2$ (1 bar of total pressure). The results were shown in FIG. 4D.

Example 25. Dealkylation. This experiment was performed according to experimental procedure VI. 4-isopropyl-3-methylphenol was used as feedstock, ZSM-5 (parent microporous ZSM-5, Si/Al=140, code: Z140-P) as a catalyst. WHSV=4.1 h⁻¹. Reaction temperature: 200-500° C. 1 bar. molar ratio of water to 4-isopropyl-3-methylphenol is 6. The results were shown in FIG. 5E.

Example 26. Dealkylation. This experiment was performed according to experimental procedure VI. 4-isopropyl-3-methylphenol was used as feedstock, hierarchical ZSM-5 (obtained from post modification of Z140-P, code: Z140-H) as a catalyst. WHSV=4.1 h⁻¹. Reaction temperature: 200-500° C. 1 bar. molar ratio of water to 4-isopropyl-3-methylphenol is 6. The results were shown in FIG. 5E.

Example 27. Dealkylation. This experiment was performed according to experimental procedure VI. 4-isopropyl-3-methylphenol was used as feedstock, ZSM-5 (parent microporous ZSM-5, Si/Al=140, code: Z140-P) as a catalyst. WHSV=4.1 h⁻¹. Reaction temperature: 395° C. 1 bar. molar ratio of water to 4-isopropyl-3-methylphenol is 6. The results were shown in FIG. 5F.

Example 28. Dealkylation. This experiment was performed according to experimental procedure VI. 4-isopropyl-3-methylphenol was used as feedstock, hierarchical ZSM-5 (obtained from post modification of Z140-P, code: Z140-H) as a catalyst. WHSV=4.1 h⁻¹. Reaction temperature: 305° C. 1 bar. molar ratio of water to 4-isopropyl-3-methylphenol is 6. The results were shown in FIG. 5F.

Example 29. Dealkylation. This experiment was performed according to experimental procedure VI. 4-methylphenol was used as feedstock, hierarchical ZSM-5 (obtained from post modification of Z140-P, code:Z140-H) as a catalyst. WHSV=2.9 h⁻¹. Reaction temperature: 400-500° C. 1 bar. molar ratio of water to 4-methylphenol is 6. The results were shown in FIG. 7A.

Example 30. Dealkylation. This experiment was performed according to experimental procedure VI. 4-methylphenol was used as feedstock, hierarchical ZSM-5 (obtained from post modification of Z140-P, code:Z140-H) as a catalyst. WHSV=2.9 h⁻¹. Reaction temperature: 410° C. 1 bar. molar ratio of water to 4-methylphenol is 6. The results were shown in FIG. 7B.

Example 31. Dealkylation. This experiment was performed according to experimental procedure VI. 4-methylphenol was used as feedstock, ZSM-5 (parent microporous ZSM-5, Si/Al=40, code Z40-P) as a catalyst. WHSV=2.9 h⁻¹. Reaction temperature: 300-500° C. 1 bar. molar ratio of water to 4-methylphenol is 6. The results were shown in FIG. 7C.

Example 32. Dealkylation. This experiment was performed according to experimental procedure VI. 4-methylphenol was used as feedstock, USY (parent microporous USY, Si/Al=40, code: USY-40) as a catalyst. WHSV=2.9 h⁻¹. Reaction temperature: 300-500° C. 1 bar. molar ratio of water to 4-methylphenol is 6. The results were shown in FIG. 7E.

Example 33. Dealkylation. This experiment was performed according to experimental procedure VI. n-propylbenzene was used as feedstock, hierarchical ZSM-5 (obtained from post modification of Z140-P, code:Z140-H) as a catalyst. WHSV=3.2 h⁻¹. Reaction temperature: 300-500° C. 1 bar. No water. The results were shown in FIG. 6A.

Example 34. Dealkylation. This experiment was performed according to experimental procedure VI. n-propylbenzene was used as feedstock, hierarchical ZSM-5 (obtained from post modification of Z140-P, code:Z140-H) as a catalyst. WHSV=3.2 h⁻¹. Reaction temperature: 410° C. 1 bar. No water. The results were shown in FIG. 6D.

Example 35. Dealkylation. This experiment was performed according to experimental procedure VI. n-propylbenzene was used as feedstock, ZSM-5 (parent microporous ZSM-5, Si/Al=12, code: Z12-P) as a catalyst. WHSV=3.2 h⁻¹. Reaction temperature: 350° C. 1 bar. No water. The results were shown in FIG. 6E.

Example 36. Dealkylation. This experiment was performed according to experimental procedure VI. The products obtained from example 23 was used as feedstock, hierarchical ZSM-5 (obtained from post modification of Z140-P, code:Z140-H) as a catalyst. WHSV=3.7 h⁻¹. Reaction temperature: 200-500 C. 1 bar. molar ratio of water to alkylphenol is around 6. The results were shown in FIG. 5A.

Example 37. Dealkylation. This experiment was performed according to experimental procedure VI. The products obtained from example 18 was used as feedstock, hierarchical ZSM-5 (obtained from post modification of Z140-P, code:Z140-H) as a catalyst. WHSV=3.7 $h^{-1}$. Reaction temperature: 410° C. 1 bar. molar ratio of water to alkylphenol is around 6. The results were shown in FIG. 5B.

Example 38. Dealkylation. This experiment was performed according to experimental procedure VI. The products obtained from example 23 was used as feedstock, hierarchical ZSM-5 (obtained from post modification of Z140-P, code:Z140-H) as a catalyst. WHSV=3.7 $h^{-1}$. Reaction temperature: 410° C. 1 bar. molar ratio of water to alkylphenol is around 6. The results were shown in FIG. 5C.

Example 39. Dealkylation. This experiment was performed according to experimental procedure VI. The products obtained from example 24 was used as feedstock, hierarchical ZSM-5 (obtained from post modification of Z140-P, code:Z140-H) as a catalyst. WHSV=2.8 $h^{-1}$. Reaction temperature: 410° C. 1 bar. molar ratio of water to alkylphenol is around 6. The results were shown in FIG. 5D.

Figure 12A:
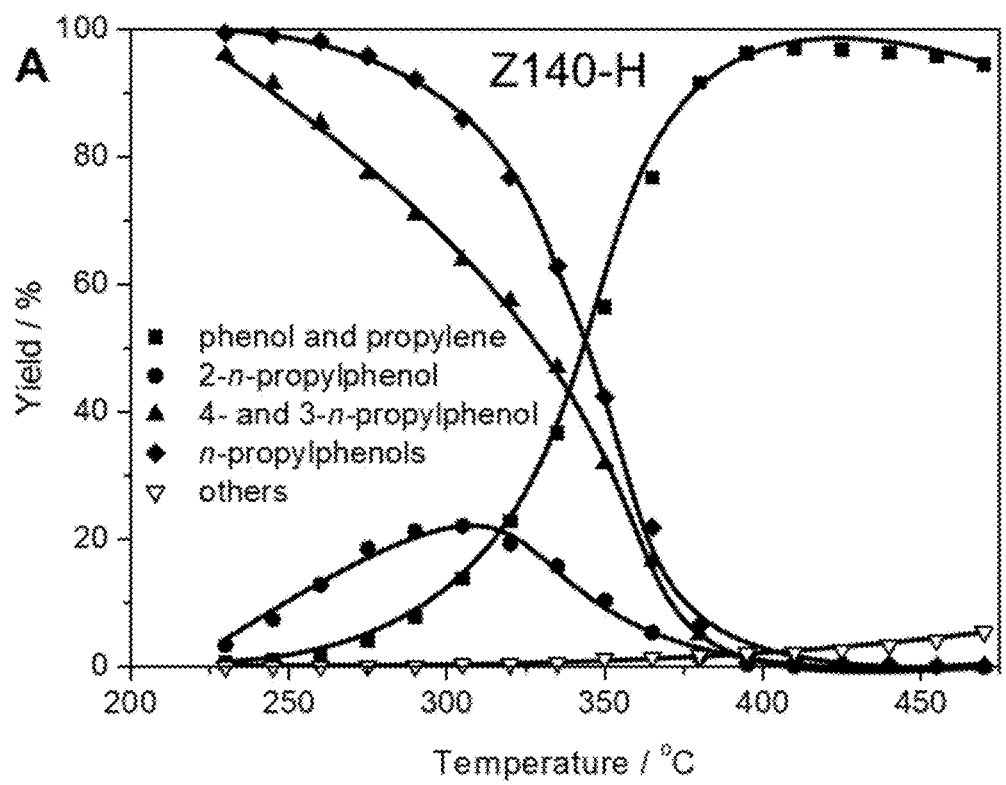
FIG. 12A: The products distribution as a function of temperature, ramping rate=1° C. $min^{-1}$.
Figure 12B:
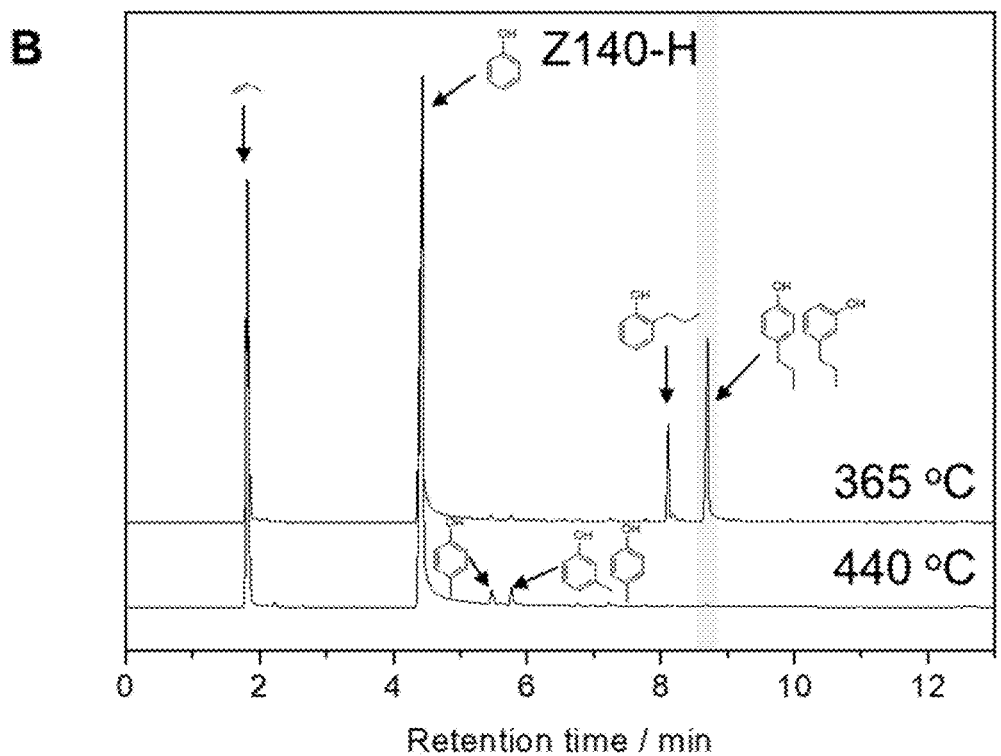
FIG. 12B: Gas chromatogram at low and high temperature (conversion)
Figure 12C:
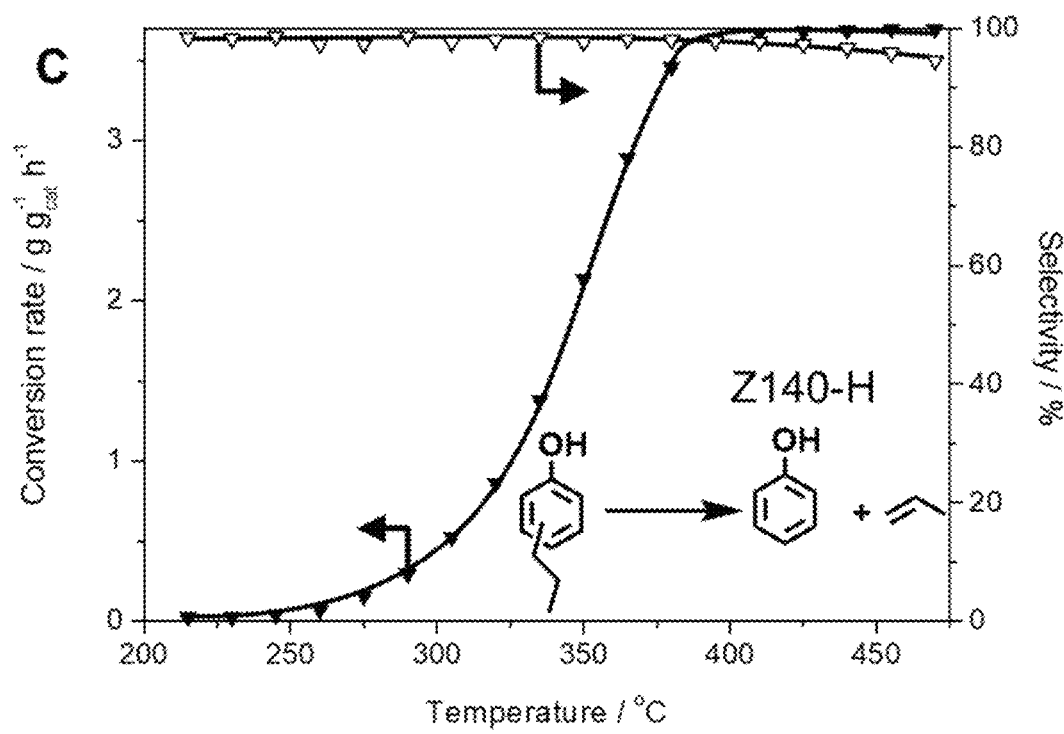
FIG. 12C: Conversion rate and selectivity to phenol and propylene as a function of temperature in the dealkylation of n-propylphenols over Z140-H.

Example 40. Dealkylation. This experiment was performed according to experimental procedure VI. 4-n-propylphenol was used as feedstock, hierarchical ZSM-5 (obtained from post modification of Z140-P, code:Z140-H) as a catalyst. WHSV=3.7 $h^{-1}$. Reaction temperature: 200-500° C. 1 bar. molar ratio of water to alkylphenol is 6. The results were shown in FIG. 12A.

Figure 12D:
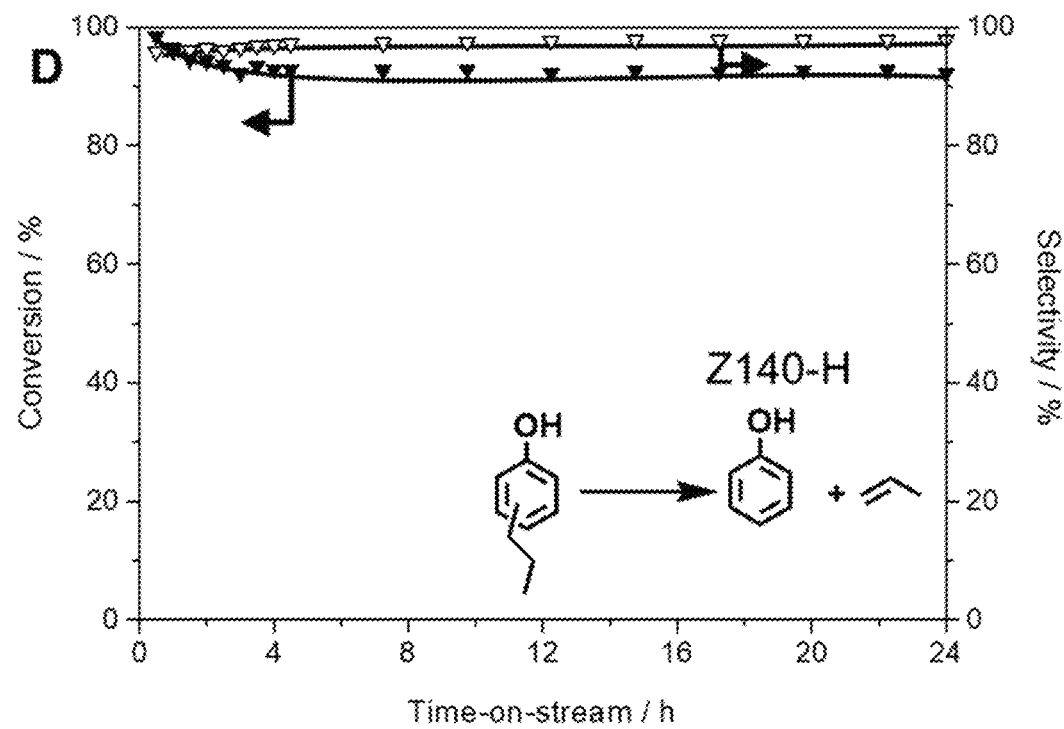
FIG. 12D: Stability of Z140-H for dealkylation of n-propylphenols (395° C.).

Example 41. Dealkylation. This experiment was performed according to experimental procedure VI. 4-n-propylphenol was used as feedstock, hierarchical ZSM-5 (obtained from post modification of Z140-P, code:Z140-H) as a catalyst. WHSV=3.7 $h^{-1}$. Reaction temperature: 395° C. 1 bar. molar ratio of water to alkylphenol is 6. The results were shown in FIG. 12D.

Figure 13A:
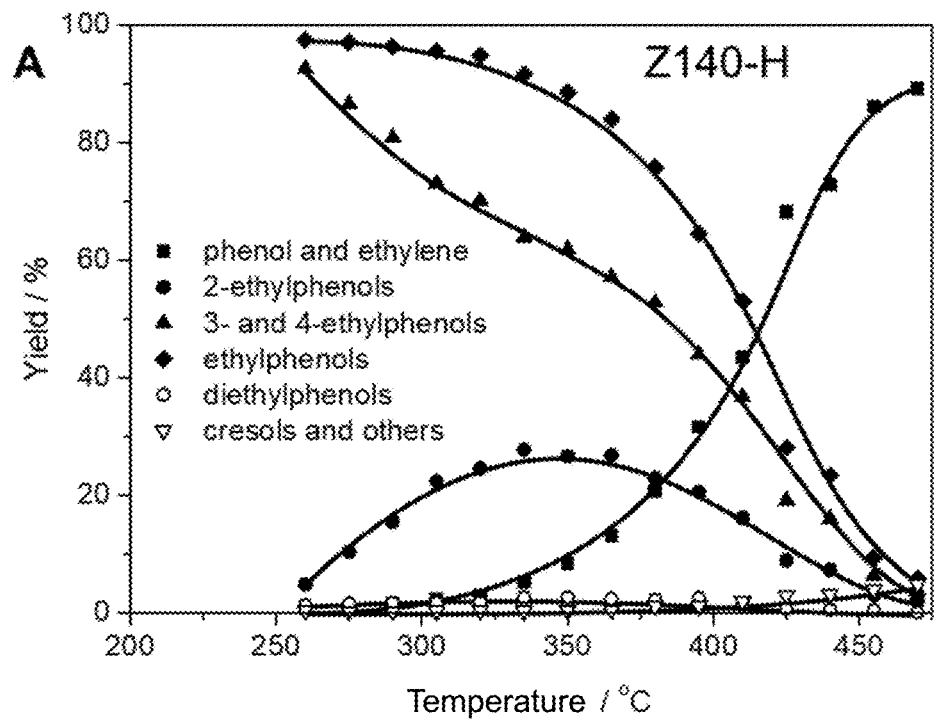
FIGS. 13A-13C. Dealkylation of 4-ethylphenol over Z140-H.
Figure 13B:
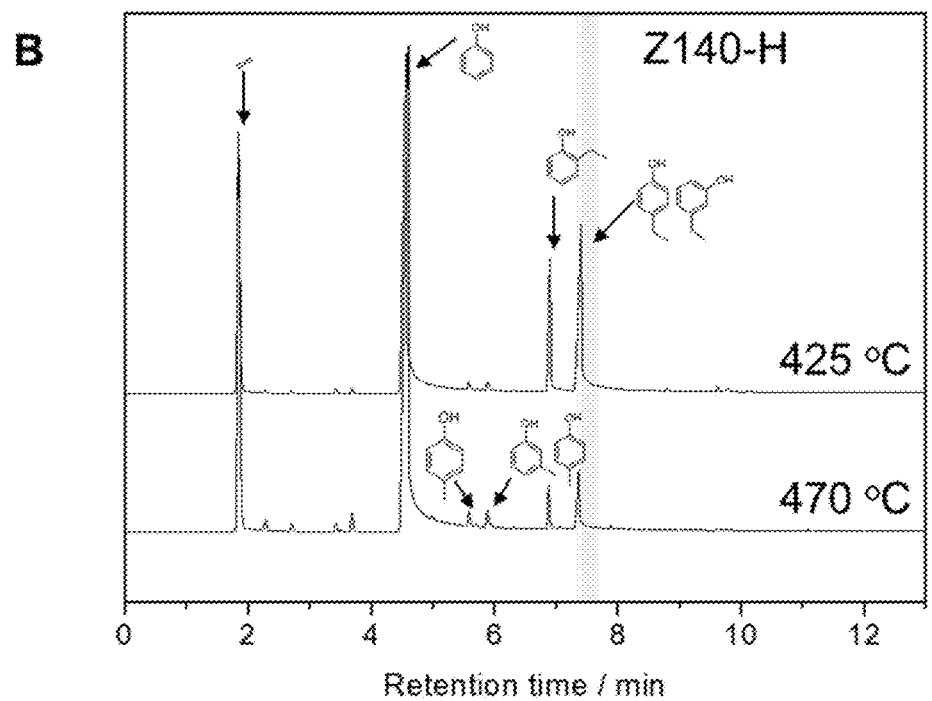

Example 42. Dealkylation. This experiment was performed according to experimental procedure VI. 4-ethylphenol was used as feedstock, hierarchical ZSM-5 (obtained from post modification of Z140-P, code:Z140-H) as a catalyst. WHSV=3.3 $h^{-1}$. Reaction temperature: 200-500° C. 1 bar. molar ratio of water to alkylphenol is 6. The results were shown in FIG. 13A.

Figure 13C:
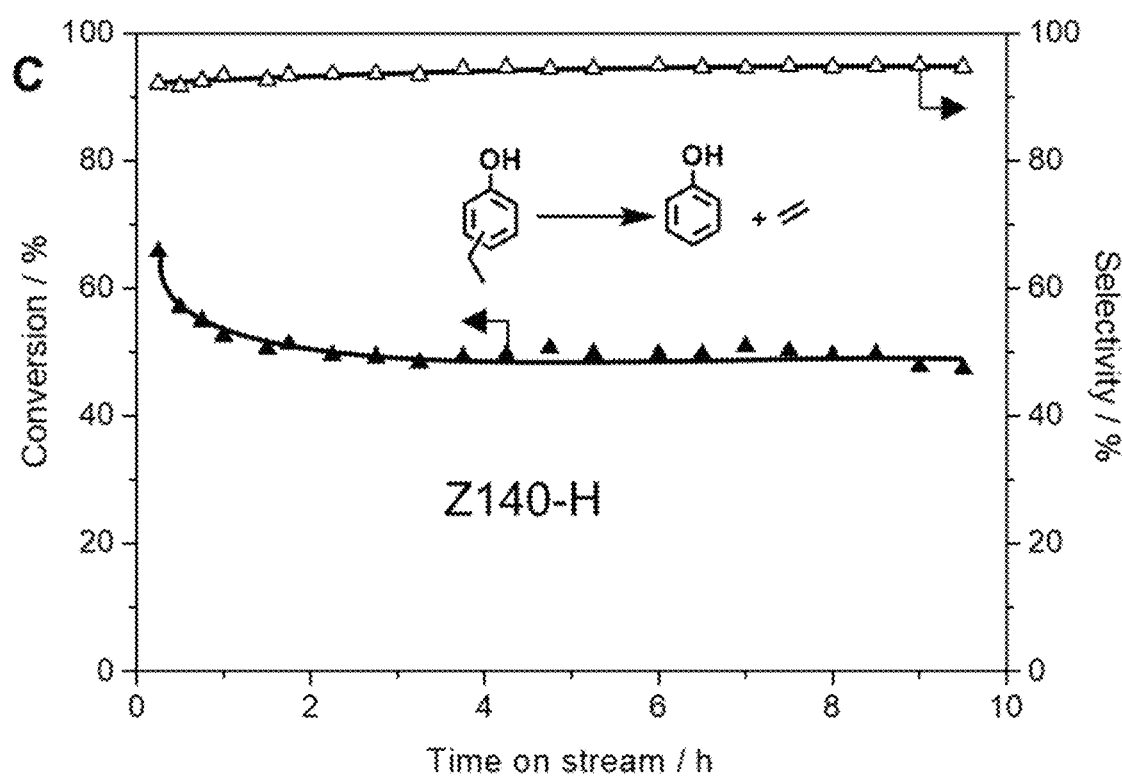

Example 43. Dealkylation. This experiment was performed according to experimental procedure VI. 4-ethylphenol was used as feedstock, hierarchical ZSM-5 (obtained from post modification of Z140-P, code:Z140-H) as a catalyst. WHSV=3.3 $h^{-1}$. Reaction temperature: 420° C. 1 bar. molar ratio of water to alkylphenol is 6. The results were shown in FIG. 13C.

Example 45. Demethoxylation and demethylation/dihydroxylation. This experiment was performed according to experimental procedure III. 4-propylguaiacol was used as feedstock, 5 wt % Pd/Al$_2$O$_3$ as a catalyst. WHSV=4.5 $h^{-1}$. Reaction temperature: 285° C. 0.4 bar H$_2$ (1 bar of total pressure). The results were shown in FIG. 3A.

Example 46. Demethoxylation and demethylation/dihydroxylation. This experiment was performed according to experimental procedure III. 4-propylguaiacol was used as feedstock, 64 wt % Ni/SiO$_2$ as a catalyst. WHSV=9.0 $h^{-1}$. Reaction temperature: 285° C. 0.98 bar H$_2$ (1 bar of total pressure). Conversion of 4-n-propylguaiacol=72.4%, selectivity to n-propylphenols=86.10%.

Example 47. Demethoxylation and demethylation/dihydroxylation. This experiment was performed according to experimental procedure III. 4-propylguaiacol was used as feedstock, 5 wt % Pt/TiO$_2$ as a catalyst. WHSV=4.5 $h^{-1}$. Reaction temperature: 325° C. 0.98 bar H$_2$ (1 bar of total pressure). Conversion of 4-n-propylguaiacol>99%, yield of n-propylbenzene=86.5%.

Example 48. Demethoxylation and demethylation/dihydroxylation. This experiment was performed according to experimental procedure III. 4-propylguaiacol was used as feedstock, 0.5 wt % Pt/TiO$_2$ as a catalyst. WHSV=4.5 $h^{-1}$. Reaction temperature: 325° C. 0.98 bar H$_2$ (1 bar of total pressure). Conversion of 4-n-propylguaiacol=81.3%, yield of n-propylphenols=52.6%.

Example 49. Demethoxylation and demethylation/dihydroxylation. This experiment was performed according to experimental procedure III. 4-propylguaiacol was used as feedstock, 10 wt % Pt/TiO$_2$ as a catalyst. WHSV=4.5 $h^{-1}$. Reaction temperature: 325° C. 0.98 bar H$_2$ (1 bar of total pressure). Conversion of 4-n-propylguaiacol>99%, yield of n-propylbenzene=85.6%.

Example 50. Demethoxylation and demethylation/dihydroxylation. This experiment was performed according to experimental procedure III. 4-propylguaiacol was used as feedstock, 5 wt % Pd/TiO$_2$ as a catalyst. WHSV=4.5 $h^{-1}$. Reaction temperature: 325° C. 0.98 bar H$_2$ (1 bar of total pressure). Conversion of 4-n-propylguaiacol>99%, yield of n-propylbenzene=73.3%.

Example 51. Demethoxylation and demethylation/dihydroxylation. This experiment was performed according to experimental procedure III. 4-propylguaiacol was used as feedstock, 5 wt % Ni/TiO$_2$ as a catalyst. WHSV=3 $h^{-1}$. Reaction temperature: 325° C. 0.98 bar H$_2$ (1 bar of total pressure). Conversion of 4-n-propylguaiacol>99%, yield of n-propylphenols=57.7%.

Example 52. Demethoxylation and demethylation/dihydroxylation. This experiment was performed according to experimental procedure III. 4-propylguaiacol was used as feedstock, 5 wt % Ru/TiO$_2$ as a catalyst. WHSV=2.25 $h^{-1}$. Reaction temperature: 325° C. 0.98 bar H$_2$ (1 bar of total pressure). Conversion of 4-n-propylguaiacol=97.9%, yield of n-propylphenols=66.2%.

Example 53. Demethoxylation and demethylation/dihydroxylation. This experiment was performed according to experimental procedure III. 4-propylguaiacol was used as feedstock, 5 wt % Pt/γ-Al$_2$O$_3$ as a catalyst. WHSV=3.0 $h^{-1}$. Reaction temperature: 325° C. 0.98 bar H$_2$ (1 bar of total pressure). Conversion of 4-n-propylguaiacol=88.4%, yield of n-propylphenols=52.5%.

Example 54. Demethoxylation and demethylation/dihydroxylation. This experiment was performed according to experimental procedure III. 4-propylguaiacol was used as feedstock, 5 wt % Pt/ZrO$_2$ as a catalyst. WHSV=2.25 $h^{-1}$. Reaction temperature: 325° C. 0.98 bar H$_2$ (1 bar of total pressure). Conversion of 4-n-propylguaiacol=70.7%, yield of n-propylphenols=43.4%.

Figure 14:
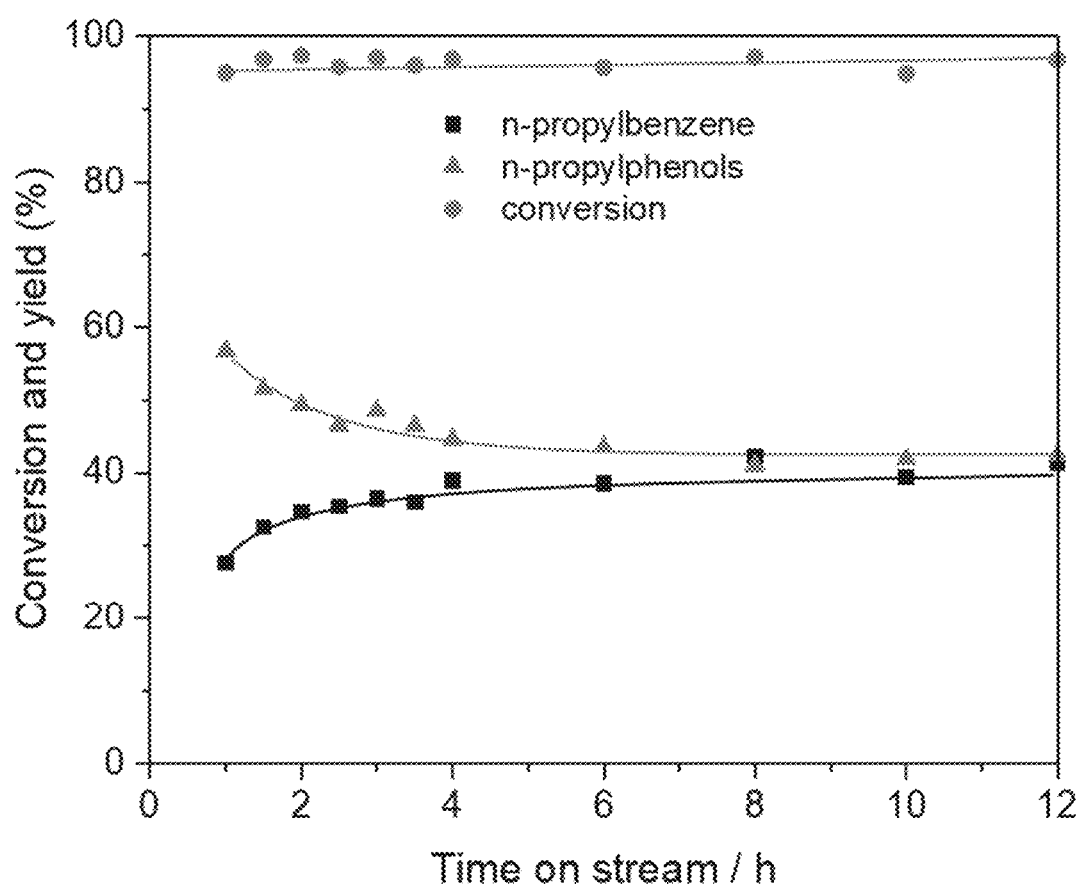
FIG. 14. The stability of 5 wt % Pt/TiO$_2$ in conversion of 4-propylguaiacol. WHSV=6.1 h$^{-1}$. Reaction temperature: 325° C. 0.98 bar H$_2$ (1 bar of total pressure).

Example 55. Demethoxylation and demethylation/dihydroxylation. This experiment was performed according to experimental procedure III. 4-propylguaiacol was used as feedstock, 5 wt % Pt/TiO$_2$ as a catalyst. WHSV=6.1 $h^{-1}$. Reaction temperature: 325° C. 0.98 bar H$_2$ (1 bar of total pressure). The stability of catalyst can be found in FIG. 14.

Figure 15:
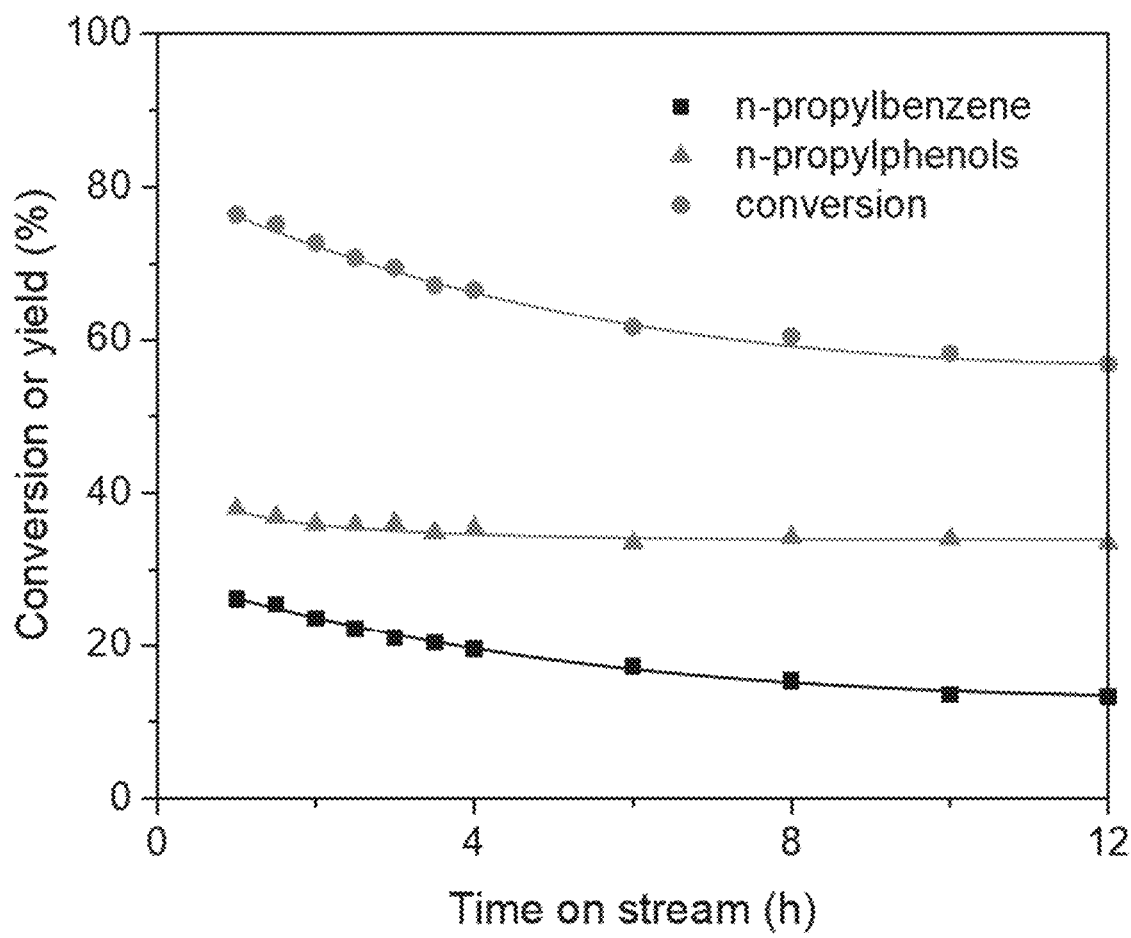
FIG. 15. The stability of 5 wt % Pd/TiO$_2$ in conversion of 4-propylguaiacol. WHSV=9.0 h$^{-1}$. Reaction temperature: 325° C. 0.98 bar H$_2$ (1 bar of total pressure).

Example 56. Demethoxylation and demethylation/dihydroxylation. This experiment was performed according to experimental procedure III. 4-propylguaiacol was used as feedstock, 5 wt % Pd/TiO$_2$ as a catalyst. WHSV=9.0 $h^{-1}$. Reaction temperature: 325° C. 0.98 bar H$_2$ (1 bar of total pressure). The stability of catalyst can be found in FIG. 15.

Figure 16:
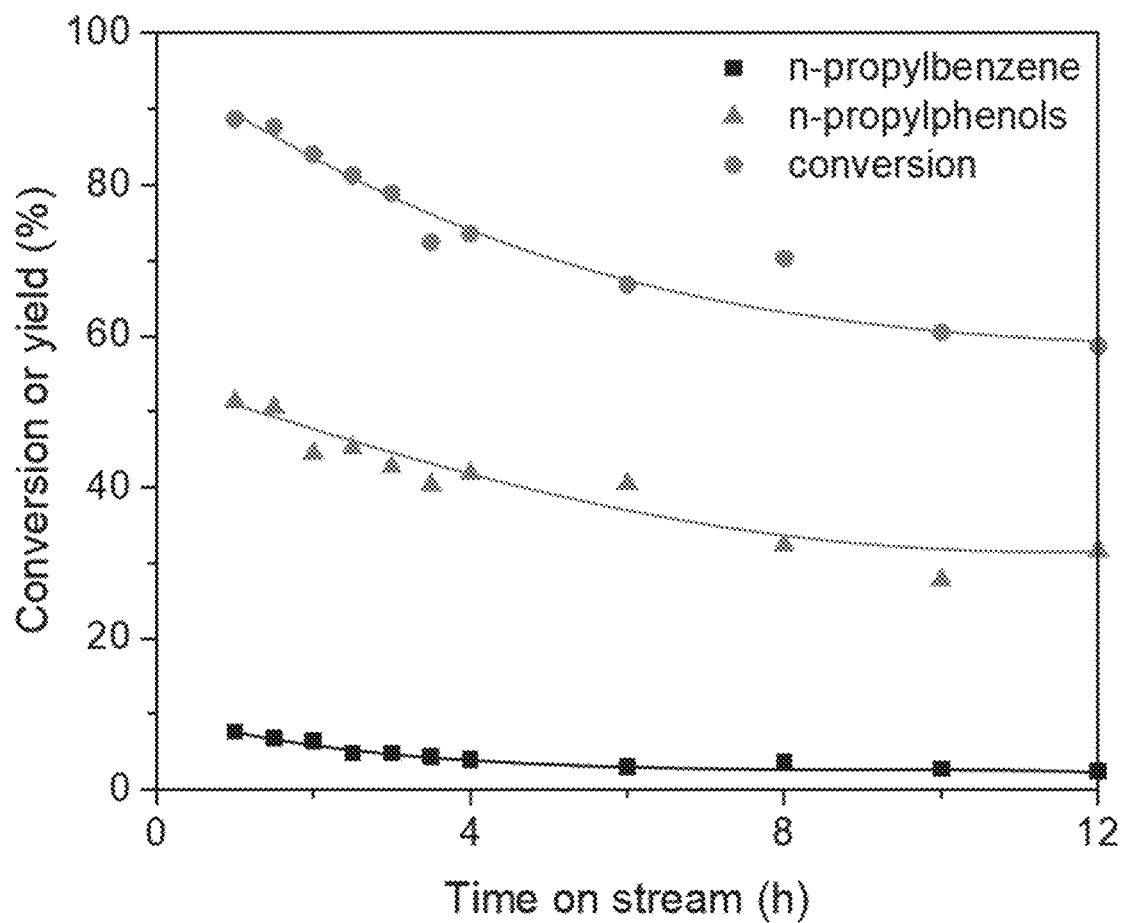
FIG. 16. The stability of 5 wt % Pt/γ-Al$_2$O$_3$ in conversion of 4-propylguaiacol. WHSV=6.1 h$^{-1}$. Reaction temperature: 325° C. 0.98 bar H$_2$ (1 bar of total pressure).

Example 57. Demethoxylation and demethylation/dihydroxylation. This experiment was performed according to experimental procedure III. 4-propylguaiacol was used as feedstock, 5 wt % Pt/γ-Al$_2$O$_3$ as a catalyst. WHSV=6.1 h$^{-1}$. Reaction temperature: 325° C. 0.98 bar H$_2$ (1 bar of total pressure). The stability of catalyst can be found in FIG. 16.

Example 58. Demethoxylation and demethylation/dihydroxylation. This experiment was performed according to experimental procedure III. 4-propylsyringol was used as feedstock, 5 wt % Pt/TiO$_2$ as a catalyst. WHSV=7.1 h$^{-1}$. Reaction temperature: 325° C. 0.98 bar H$_2$ (1 bar of total pressure). Conversion of 4-propylsyringol>99%, yield of n-propylphenols=75%.

Legend to the Tables

Table 1. One step conversion of lignin into phenol.

Table 2. Multiple-steps conversion of lignin into biophenol.

Table 3. Monomer yield and distribution obtained from RCF of birch wood and

Table 4: The composition of condensed hydroprocessing products.

References to this application

1. A. Kätelhön, R. Meys, S. Deutz, S. Suh and A. Bardow, Proceedings of the National Academy of Sciences, 2019, 116, 11187-11194.
2. International Energy Agency, IEA, The future of petrochemicals towards a more sustainable chemical industry. (IEA Publications France, 2018; OECD/IEA 2018 IEA Publications International Energy Agency
3. T. Werpy, G. Petersen, A. Aden, J. Bozell, J. Holladay, J. White, A. Manheim, D. Eliot, L. Lasure and S. Jones, Top value added chemicals from biomass. Volume 1—Results of screening for potential candidates from sugars and synthesis gas, Department of Energy Washington DC, 2004.
4. J. E. Holladay, J. F. White, J. J. Bozell and D. Johnson, *Top Value Added Chemicals from Biomass-Volume II, Results of Screening for Potential Candidates from Biorefinery Lignin*, Pacific Northwest National Lab. (PNNL), Richland, WA (United States); National Renewable Energy Laboratory (NREL), Golden, CO (United States), 2007.
5. D. M. Alonso, S. H. Hakim, S. Zhou, W. Won, O. Hosseinaei, J. Tao, V. Garcia-Negron, A. H. Motagamwala, M. A. Mellmer and K. Huang, *Science advances*, 2017, 3, e1603301.
6. A. J. Ragauskas, G. T. Beckham, M. J. Biddy, R. Chandra, F. Chen, M. F. Davis, B. H. Davison, R. A. Dixon, P. Gilna and M. Keller, *Science*, 2014, 344, 1246843.
7. C. Li, X. Zhao, A. Wang, G. W. Huber and T. Zhang, *Chemical reviews*, 2015, 115, 11559-11624.
8. Z. Sun, B. l. Fridrich, A. de Santi, S. Elangovan and K. Barta, *Chemical reviews*, 2018, 118, 614-678.
9. J. G. Linger, D. R. Vardon, M. T. Guarnieri, E. M. Karp, G. B. Hunsinger, M. A. Franden, C. W. Johnson, G. Chupka, T. J. Strathmann, P. T. Pienkos, G. T. Beckham, Lignin valorization through integrated biological funneling and chemical catalysis. *Proc. Natl. Acad. Sci. U.S.A.* 111, 12013-12018 (2014).
10. K. Byoungjin, H. Park). Na, and S. Y. Lee. *Biotechnology journal.* 2014, 9, 621-629.
11. W. Manfred, W. Markus and M. Kleine-Boymann, *Ullmann's Encyclopedia of Industrial Chemistry,* 2004.
12. R. J. Schmidt, *Applied Catalysis A: General,* 2005, 280, 89-103.
13. R. Bal, M. Tada, T. Sasaki and Y. Iwasawa, *Angewandte Chemie International Edition,* 2006, 45, 448-452.
14. W. Schutyser, T. Renders, S. Van den Bosch, S.-F. Koelewijn, G. Beckham and B. F. Sels, *Chemical society reviews,* 2018, 47, 852-908.
15. H. Chum, D. Johnson, S. Black, M. Ratcliff and D. Goheen, in *Advances in solar energy*, Springer, 1988, pp. 91-200.
16. D. T. Huibers, H. J. Parkhurst Jr, U.S. Pat. No. 4,420,644A (1983)
17. W. Lan, M. Talebi Amiri, C. M. Hunston and J. Luterbacher, *Angewandte Chemie International Edition,* 2018, 57, 1356-1360.
18. D. W. Goheen, in *Lignin Structure and Reactions*, AMERICAN CHEMICAL SOCIETY, 1966, vol. 59, ch. 14, pp. 205-225.
19. G. J. Snell, D. T. Huibers, U.S. Pat. No. 4,409,416A (1983)
20. G. J. Snell, D. T. Huibers, U.S. Pat. No. 4,409,416A (1983)
21. Z. Ma, A. K. Ghosh, J. Van Bokhoven, U.S. Patent US20170152200A1 (2017).
22. Y. Zhao, L. Deng, B. Liao, Y. Fu and Q.-X. Guo, Energy & Fuels, 2010, 24, 5735-5740.
23. A. Pattiya, J. O. Titiloye and A. V. Bridgwater, Journal of Analytical and Applied Pyrolysis, 2008, 81, 72-79.
24. H. S. Choi and D. Meier, Journal of analytical and applied pyrolysis, 2013, 100, 207-212.
25. Q. Bu, H. Lei, L. Wang, Y. Wei, L. Zhu, X. Zhang, Y. Liu, G. Yadavalli and J. Tang, *Bioresource technology,* 2014, 162, 142-147.
26. Z. Ma, E. Troussard and J. A. van Bokhoven, *Applied Catalysis A: General,* 2012, 423, 130-136.
27. J. Long, Q. Zhang, T. Wang, X. Zhang, Y. Xu and L. Ma, *Bioresource Technology,* 2014, 154, 10-17.
28. A. Toledano, L. Serrano and J. Labidi, *Journal of Chemical Technology & Biotechnology,* 2012, 87, 1593-1599.
29. M. M. Hepditch and R. W. Thring, *The canadian journal of chemical engineering,* 2000, 78, 226-231.
30. D. W. Goheen, Hydrogenation of lignin by noguchi process in Advances in Chemistry Series. (American Chemical Society, 1966), pp. 205-225.
31. O. Motoyoshi, M. Yoshio, K. Kan, U.S. Pat. No. 3,223,698A (1965).
32. O. Motoyoshi, M. Yoshio, K. Kan. U.S. Pat. No. 3,105,095A (1963).
33. D. Meier, J. Berns, C. Grünwald and O. Faix, *Journal of analytical and applied pyrolysis,* 1993, 25, 335-347.
34. M. A. Ratcliff, D. K. Johnson, F. L. Posey and H. L. Chum, *Applied Biochemistry and Biotechnology,* 1988, 17, 151-160.
35. A. Kloekhorst and H. J. Heeres, *ACS Sustainable Chemistry & Engineering,* 2015, 3, 1905-1914.
36. A. McVeigh, F. P. Bouxin, M. C. Jarvis and S. D. Jackson, *Catalysis Science & Technology,* 2016, 6, 4142-4150.
37. A. Oasmaa, R. Alén and D. Meier, Bioresource Technology, 1993, 45, 189-194.
38. D. Meier, R. Ante and O. Faix, Bioresource Technology, 1992, 40, 171-177.
39. K. H. Kim, B. A. Simmons and S. Singh, Green Chemistry, 2017, 19, 215-224.
40. P. T. Patil, U. Armbruster, M. Richter and A. Martin, Energy & Fuels, 2011, 25, 4713-4722
41. W. Xu, S. J. Miller, P. K. Agrawal and C. W. Jones, ChemSusChem, 2012, 5, 667-675.
42. J. O. Stru? ven and D. Meier, ACS Sustainable Chemistry & Engineering, 2016, 4, 3712-3721.

43. D. Meier, J. Berns, O. Faix, U. Balfanz and W. Baldauf, Biomass and Bioenergy, 1994, 7, 99-105.
44. A. Kloekhorst, J. Wildschut and H. J. Heeres, *Catalysis Science & Technology*, 2014, 4, 2367-2377.
45. S. Van den Bosch, W. Schutyser, R. Vanholme, T. Driessen, S.-F. Koelewijn, T. Renders, B. De Meester, W. Huijgen, W. Dehaen and C. Courtin, *Energy & Environmental Science*, 2015, 8, 1748-1763.
46. A. L. Jongerius, P. C. Bruijnincx and B. M. Weckhuysen, *Green chemistry*, 2013, 15, 3049-3056.
47. M. Wang, M. Liu, H. Li, Z. Zhao, X. Zhang and F. Wang, *ACS Catalysis*, 2018.
48. A. N. Wilson, A. Dutta, B. A. Black, C. Mukarakate, K. Magrini, J. A. Schaidle, W. E. Michener, G. T. Beckham and M. R. Nimlos, *Green Chemistry*, 2019, 21, 4217-4230.
49. T. Yoshikawa, T. Yagi, S. Shinohara, T. Fukunaga, Y. Nakasaka, T. Tago and T. Masuda, *Fuel processing technology*, 2013, 108, 69-75.
50. T. Yoshikawa, S. Shinohara, T. Yagi, N. Ryumon, Y. Nakasaka, T. Tago and T. Masuda, *Applied Catalysis B: Environmental*, 2014, 146, 289-297.
51. Z. Cao, J. Engelhardt, M. Dierks, M. T. Clough, G. H. Wang, E. Heracleous, Lappas, R. Rinaldi and F. Schüth, *Angewandte Chemie*, 2017, 129, 2374-2379.
52. P. de Wild, W. Huijgen, A. Kloekhorst, R. Chowdari and H. Heeres, Bioresource technology, 2017, 229, 160-168.
53. J. Gendler, D. Huibers and H. Parkhurst, in *Wood a Agricultural Residues*, Elsevier, 1983, pp. 391-400.
54. M. Saidi, F. Samimi, D. Karimipourfard, T. Nimmanwudipong, B. C. Gates and M. R. Rahimpour, *Energy & Environmental Science*, 2014, 7, 103-129.
55. E. Anderson, A. Crisci, K. Murugappan and Y. Romin-Leshkov, *ChemSusChem*, 2017, 10, 2226-2234.
56. S. Song, J. Zhang, G. Gözaydin and N. Yan, *Angewandte Chemie*, 2019, 131, 4988-4991.
57. X. Liu, C. Wang, Y. Zhang, Y. Qiao, Y. Pan and L. Ma, *ChemSusChem*, 2019.
58. L. Dong, Y. Xin, X. Liu, Y. Guo, C.-W. Pao, J.-L. Chen and Y. Wang, *Green Chemistry*, 2019, 21, 3081-3090.
59. A. Vuori and J.-s. Bredenberg, *Holzforschung-International Journal of the Biology, Chemistry, Physics and Technology of Wood*, 1984, 38, 253-262.
60. N. Joshi and A. Lawal, *Industrial & Engineering Chemistry Research*, 2013, 52, 4049-4058.
61. J. Zhang, L. Lombardo, G. Gozaydin, P. J. Dyson and N. Yan, *Chinese Journal of Catalysis*, 2018, 39, 1445-1452
62. D. Verboekend, Y. Liao, W. Schutyser and B. F. Sels, *Green Chemistry*, 2016, 18, 297-306.
63. T. Yamagishi, I. Tsutomu, E. Takahashi. U.S. Pat. No. 4,927,979A, 1990.
64. I. Kumaniaev, E. Subbotina, J. Sävmarker, M. Larhed, M. V. Galkin and J. S. Samec, *Green Chemistry*, 2017, 19, 5767-5771.
65. E. M. Anderson, M. L. Stone, R. Katahira, M. Reed, G. T. Beckham and Y. Román-Leshkov, *Joule*, 2017, 1, 613-622.
66. Q. Song, F. Wang, J. Cai, Y. Wang, J. Zhang, W. Yu and J. Xu, *Energy& Environmental Science*, 2013, 6, 994-1007.
67. R. Srivastava, M. Choi and R. Ryoo, Chemical Communications, 2006, 4489-4491
68. F. Imbert, M. Guisnet and S. Gnep, Jouranl of Catalysis, 2000, 195, 279-286.
69. H. Fiege, Ullmann's Encyclopedia of Industrial Chemistry, 2000.
70. U.S. Pat. No. 3,578,714A (1968).
71. H. Sixta, Handbook of pulp, Wiley-vch, 2006
72. E. Anderson, A. Crisci, K. Murugappan, Y. Román-?Leshkov. ChemSusChem, 2017, 10, 2226-2234
73. S. L Yohe, H. J. Choudhari, D. D. Mehta, P. J. Dietrich, M. D. Detwiler, C. M. Akatay, E. A. Stach, J. T. Miller, W. N. Delgass, R. Agrawal, F. H. Ribeiro. Journal of Catalysis, 2016, 344, 535-552
74. H. Choudhari, Thesis, 2015, Purdue university.

What is claimed is:

1. A method comprising the steps of:
a) providing a mixture of compounds obtained from catalytic fractionation of lignocellulose and/or lignin, the mixture of compounds comprising formula (I):

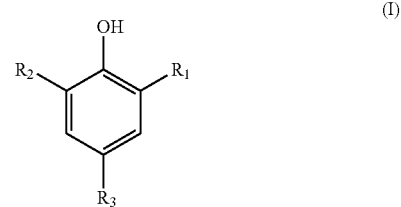

wherein:
each occurrence of $R_1$ and $R_2$ is independently selected to be —O—$CH_3$ or —H;
each occurrence of $R_3$ is independently selected to be —H, or -methyl, or -ethyl, or -propyl, or -propylene, or -1-alkoxypropyl, or -3-hydroxypropyl;
b) preparing a reaction mixture by contacting the mixture of compounds of step a) in gas phase, with a reaction mixture containing a metal-based catalyst, under a hydrogen containing gas atmosphere;
wherein step b) is carried out at a temperature of at least 265° C. and a partial hydrogen pressure of at least 0.2 bar; and
c) obtaining from step b) products comprising a mixture of compounds of formula (Ia), as well as methane or methanol or both

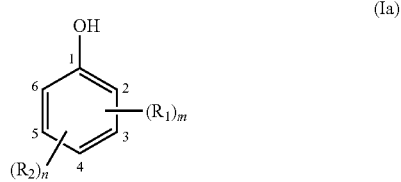

wherein:
$R_1$ is independently selected to be —$CH_3$ or —H;
$R_2$ is independently selected to be —H, or -methyl, or -ethyl, or -propyl; and
m and n represent the position on the aromatic ring, with m being any one of the numbers 2-6 and with n being any one of the numbers 3-5, with m not being equal to n.

2. The method according to claim 1, wherein the metal-based catalyst comprises metal attached to a support material.

3. The method according to claim 1, wherein the metal-based catalyst comprises metal attached to a support material and wherein the metal is nickel and the support is silica.

4. The method according to claim 1, wherein the metal-based catalyst is a promoter-modified nickel catalyst.

5. The method according to claim 1, wherein in step b) a partial pressure of 0.2-10 bar $H_2$ is used.

6. The method according to claim 1, wherein in step b) a partial pressure of 0.2-1 bar $H_2$ is used.

7. The method according to claim 1, wherein a complete removal of methoxy substituents is obtained with >70% molar yield to propyl phenols or ethyl phenols or a combination of both, based on a mixture of compounds with formula (I).

8. The method according to claim 1, further comprising subjecting the mixture of compounds of formula (Ia) obtained in step c) to a dealkylation process comprising the steps of:
  d) providing the mixture of compounds of formula (Ia);
  e) preparing a reaction mixture by contacting the mixture of compounds of step d) in gas phase, with an acidic zeolite, and water and wherein step e) is carried out at a temperature of at least 260° C.; and
  f) obtaining from step e) products comprising a mixture of compounds of formula (Ib) as well as olefins comprising propylene or ethylene or a combination of both,

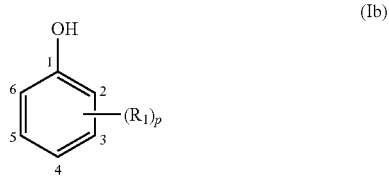

(Ib)

wherein:
  $R_1$ is independently selected from —$CH_3$ or —H; and
  p represents the position on the aromatic ring, with p being any one of the numbers 2-6.

9. The method according to claim 8, wherein the acidic zeolite belongs to the pentasil family of zeolites.

10. The method according to claim 8, wherein the acidic zeolite is a ZSM-5 zeolite.

11. The method according to claim 8, wherein the acidic zeolite is a hierarchical version of a ZSM-5 zeolite with Si/Al ratio of 140.

12. The method according to claim 8, wherein a partial pressure of 0.2-1 bar $H_2$ in step b) is used and wherein the metal-based catalyst comprises metal attached on a support material wherein the metal is nickel and the support is silica.

13. The method according to claim 8, wherein the mixture of compounds with formula (Ib) and olefins are obtained in a molar yield of >40% based on the mixture of compounds with formula (I).

14. The method according to claim 1, further comprising converting the produced mixture of compounds with formula (Ia) into a mixture of compounds with formula (Ic):

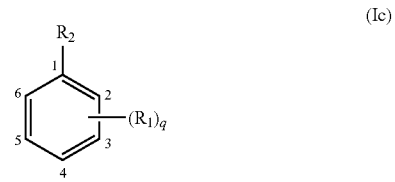

(Ic)

wherein:
  $R_1$ is independently selected to be —$CH_3$ or —H;
  $R_2$ is independently selected to be -propyl or -ethyl; and
  q represents the position on the aromatic ring, with q being any one of the numbers 2-6.

15. The method according to claim 14, wherein the metal-based catalyst comprises a platinum group metal (PGM) selected from the group consisting of platinum and palladium, and wherein this metal is on a titanium oxide support.

16. The method according to claim 14, wherein the metal-based catalyst is selected from the group consisting of a promoter-modified platinum catalyst and a promoter-modified palladium catalyst.

17. The method according to claim 14, wherein the metal-based catalyst achieves a constant conversion of the mixture of compounds with formula al for a time on stream of at least 5 hours, measured at a conversion level below full conversion.

18. The method according to claim 14, wherein a mixture of compounds with formula (Ic) is obtained in >60% molar yield based on a mixture of compounds with formula (I).

19. The method according to claim 14, wherein n-propylbenzene is obtained in >40% molar yield based on a mixture of compounds with formula (I).

20. The method according to claim 14, wherein a partial pressure of 0.2-1 bar $H_2$ in step b) is used.

* * * * *